United States Patent
Landry et al.

(10) Patent No.: US 8,815,883 B2
(45) Date of Patent: Aug. 26, 2014

(54) COMPOUNDS AND METHODS FOR INHIBITING SEROTONIN SYNTHESIS

(75) Inventors: Donald Landry, New York, NY (US); Shi-Xian Deng, White Plains, NY (US)

(73) Assignee: The Trustees of Columbia Unviersity in the City of New York, New York, NY (US)

(*) Notice: Subject to any disclaimer, the term of this patent is extended or adjusted under 35 U.S.C. 154(b) by 12 days.

(21) Appl. No.: 13/504,693

(22) PCT Filed: Nov. 2, 2010

(86) PCT No.: PCT/US2010/055125
§ 371 (c)(1),
(2), (4) Date: Nov. 12, 2012

(87) PCT Pub. No.: WO2011/053977
PCT Pub. Date: May 5, 2011

(65) Prior Publication Data
US 2013/0053343 A1  Feb. 28, 2013

Related U.S. Application Data

(60) Provisional application No. 61/257,099, filed on Nov. 2, 2009.

(51) Int. Cl.
| | | |
|---|---|---|
| A01N 43/54 | (2006.01) | |
| A61K 31/505 | (2006.01) | |
| A61K 31/506 | (2006.01) | |
| C07D 239/34 | (2006.01) | |
| C07D 239/47 | (2006.01) | |
| C07D 239/52 | (2006.01) | |
| C07D 239/56 | (2006.01) | |

(52) U.S. Cl.
CPC ............ A61K 31/506 (2013.01); A61K 31/505 (2013.01); C07D 239/34 (2013.01); C07D 239/47 (2013.01); C07D 239/52 (2013.01); C07D 239/56 (2013.01)
USPC ........... 514/272; 514/269; 544/319; 544/321; 544/312

(58) Field of Classification Search
CPC .. C07D 239/34; C07D 239/47; C07D 239/52; C07D 239/56; A61K 31/506; A61K 31/505
USPC ................ 544/312, 319, 321; 514/269, 272
See application file for complete search history.

(56) References Cited

U.S. PATENT DOCUMENTS

| | | | |
|---|---|---|---|
| 5,403,824 A | 4/1995 | D'Souza et al. | |
| 7,198,914 B2 | 4/2007 | Maruyama et al. | |
| 8,093,291 B2* | 1/2012 | Brown et al. | 514/529 |
| 2005/0203130 A1 | 9/2005 | Buntinx | |
| 2006/0135415 A1 | 6/2006 | Jameson et al. | |
| 2007/0191370 A1 | 8/2007 | Devasagayaraj et al. | |
| 2008/0153852 A1 | 6/2008 | Devasagayaraj et al. | |
| 2009/0005381 A1 | 1/2009 | Brown et al. | |
| 2009/0029993 A1 | 1/2009 | Liu et al. | |
| 2011/0152220 A1* | 6/2011 | Karsenty et al. | 514/108 |

FOREIGN PATENT DOCUMENTS

| | | |
|---|---|---|
| WO | 2007/089335 A2 | 8/2007 |
| WO | WO 2007089335 A2 * | 8/2007 |
| WO | 2008/073933 A2 | 6/2008 |
| WO | 2009/002964 A1 | 12/2008 |
| WO | 2009/002970 A1 | 12/2008 |
| WO | 2009/009561 A1 | 1/2009 |
| WO | 2009/014972 A1 | 1/2009 |
| WO | 2009/029499 A1 | 3/2009 |
| WO | 2009/045900 A2 | 4/2009 |
| WO | 2009/123978 A1 | 10/2009 |
| WO | 2010/056992 A1 | 5/2010 |
| WO | WO 2010062829 A1 * | 6/2010 |

OTHER PUBLICATIONS

Q. Liu et al., Journal of Pharmacology and Experimental Therapeutics (2008), 325(1), 47-55.*
Z-C Shi et al., Journal of Medicinal Chemistry (2008), 51(13),3684-3687.*
G. Cianchetta et al., Current Chemical Genomics (2010), 4, 19-26.*
1. Côté, F. et al., "Disruption of the Nonneuronal tph1 Gene Demonstrates the Importance of Peripheral Serotonin in Cardiac Function", Proc. Natl. Acad. Sci. USA (2003), vol. 100:23, pp. 13525-13530.
Gershon, M.D. et al., "The Serotonin Signaling System: From Basic Understanding to Drug Development for Functional GI Disorders", Gastroenterology (2007), vol. 132:, pp. 397-414.
Gershon, M.D. et al., "5-HT Receptor Subtypes Outside the Central Nervous System. Roles in the Physiology of the Gut", Neuropsychopharmacology (1990), vol. 3:5-6, pp. 385-395.

(Continued)

*Primary Examiner* — Deepak Rao
*Assistant Examiner* — Alexander R Pagano
(74) *Attorney, Agent, or Firm* — Kenyon & Kenyon LLP

(57) ABSTRACT

Compounds having the structures below that are TPH1 inhibitors are provided: The compounds are useful of, e.g., to increase bone mass. In preferred embodiments, the patient is known to have, or to be at risk for, a low bone mass disease such as osteoporosis.

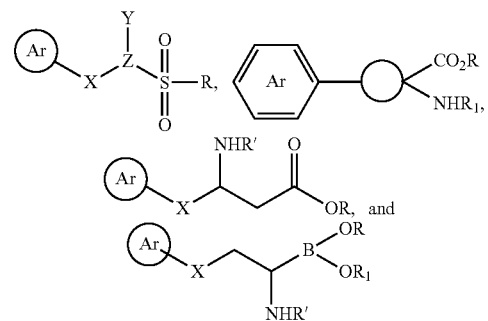

1 Claim, 11 Drawing Sheets

(56) References Cited

OTHER PUBLICATIONS

Gong, Y. et al., "LDL Receptor-Related Protein 5 (LRP5) Affects Bone Accrual and Eye Development", Cell (2001), vol. 107:4, pp. 513-523.

Liu, Q. et al., "Discovery and Characterization of Novel Tryptophan Hydroxylase Inhibits That Selectively Inhibit Serotonin Synthesis in the Gastrointestinal Tract", J. Pharma and Expri. Thera. (2008), vol. 325:1, pp. 47-55.

Noda, M. et al., "Multiple Signal Transduction Pathways Mediated by 5-HT Receptors", Mol. Neurobiol. (2004), vol. 29:1, pp. 31-39.

Walther, D.J. et al., "Synthesis of Serotonin by a Second Tryptophan Hydroxylase Isoform", Science (2003), vol. 299:5603, p. 76.

Warden, S.J. et al., "Inhibition of the Serotonin (5-Hydroxytryptamine) Transporter Reduces Bone Accrual During Growth", Endocrinology (2005), vol. 146:2, pp. 685-693.

Westbroek, I. et al. "Expression of Serotonin Receptors in Bone", J. Biol. Chem. (2001), vol. 276:31, pp. 28961-28968.

\* cited by examiner

WT　　　　　　　　　Lrp5 Act Duo

COMPOUNDS AND METHODS FOR INHIBITING SEROTONIN SYNTHESIS

CROSS REFERENCE TO RELATED APPLICATIONS

This application is the national phase application of International Application Number PCT/US2010/055125, filed Nov. 2, 2010, which claims the benefit of priority to U.S. Application No. 61/257,099, filed Nov. 2, 2009, and is incorporated herein by reference in its entirety.

FIELD OF THE INVENTION

The invention is in the field of prevention and therapy of diseases or disorders mediated by peripheral serotonin, e.g., diseases associated with lower than normal bone mass such as osteoporosis.

BACKGROUND OF THE INVENTION

Bone remodeling, the mechanism whereby vertebrates renew bone tissues throughout adulthood, comprises two phases: resorption of preexisting mineralized bone matrix by a specialized cell type, the osteoclast, followed by de novo bone formation by another specialized cell type, the osteoblast. Genetic and molecular studies have shown that local effectors (cytokines and growth factors) and systemic effectors (hormones and neuromediators) modulate both phases of bone remodeling.

One of the most intensively studied genes regulating bone remodeling is LDL-receptor related protein 5 (LRP5). Loss-of-function mutations in LRP5 result in osteoporosis pseudoglioma (OPPG), a disease characterized by severe bone loss due to a decrease in bone formation and by the persistence of embryonic vascularization of the eyes, causing blindness. By contrast, gain-of-function mutations in LRP5 cause another bone disease, high bone mass syndrome. The involvement of Lrp5 in two human diseases of opposite nature underscores the importance of the pathways controlled by this gene in the regulation of bone formation. However, the mechanism by which LRP5 affects bone development is not known.

Mice genetically deficient for the TPH1 gene ("knockout mice") have been reported. In one case, the mice reportedly expressed normal amounts of serotonin in classical serotonergic brain regions, but largely lacked serotonin in the periphery. In another, the knockout mice exhibited abnormal cardiac activity, which was attributed to a lack of peripheral serotonin (Côté et al., 2003, Proc. Natl. Acad. Sci. USA 100:13525-13530).

International Patent Application No. PCT/US2009/038817, published as WO 2009/123978, the disclosure of which is incorporated herein in its entirety, is directed to methods of diagnosing, preventing, and treating bone mass diseases using therapeutic agents for lowering or increasing serum serotonin levels. International Patent Application No. PCT/US2009/064383, published as WO 2010/056992, the disclosure of which is incorporated herein in its entirety, is also directed to methods of diagnosing, preventing, and treating bone mass diseases using therapeutic agents for lowering or increasing serum serotonin levels.

SUMMARY OF THE INVENTION

The present invention provides compounds that are inhibitors of tryptophan hydroxylase 1 (TPH1), the enzyme responsible for the first step of serotonin synthesis in enterochromaffin cells of the duodenum, as well as pharmaceutical compositions comprising the compounds. The compounds and pharmaceutical compositions comprising the compounds are useful for the treatment and/or prevention of conditions where it is beneficial to inhibit TPH1 and thus lower serum serotonin levels.

It has been discovered that elevated levels of serum serotonin due to overexpression of TPH1 causes decreased bone mass in LRP5 loss of function mutants. Thus, certain embodiments of the invention are directed to methods for treating or preventing low bone mass diseases such as osteoporosis and osteoporosis pseudoglioma (OPPG) by administering compounds that inhibit serotonin synthesis or inhibit TPH1, the enzyme necessary for serotonin synthesis in duodenum. In certain embodiments, the methods may also include administering antagonists of the serotonin receptor HT1B, a receptor mediating the effect of serotonin on osteoblasts.

The compounds disclosed herein that are inhibitors of TPH1 are useful for treating diseases or disorders mediated by peripheral serotonin. In certain embodiments, the compounds disclosed herein that are inhibitors of TPH1 may be used to affect gastrointestinal motility and gastric emptying, e.g., by slowing gastrointestinal motility and gastric emptying. In certain embodiments, the compounds disclosed herein that are inhibitors of TPH1 may be useful in the treatment or prevention of chemotherapy-induced emesis or irritable bowel syndrome.

Certain other embodiments of the invention are directed to pharmaceutical compositions for increasing bone mass that include compounds disclosed herein that decrease serum serotonin levels, optionally together with one or more serotonin receptor antagonists, for use in treating or preventing low bone mass diseases. In some embodiments, the present invention includes a pharmaceutical composition for treating or preventing anxiety or depression where the pharmaceutical composition includes both a selective serotonin reuptake inhibitor (SSRI) and a compound disclosed herein that reduces the level of serum serotonin, in order to prevent patients treated with serotonin reuptake inhibitors from developing osteoporosis or to treat osteoporosis in patients taking SSRIs.

In other embodiments, the present invention provides methods of treating patients for anxiety or depression where an SSRI and a compound disclosed herein that reduces the level of serum serotonin are administered to a patient via separate pharmaceutical compositions.

U.S. Provisional Patent Application Ser. No. 60/976,403, filed Sep. 28, 2007, and International Patent Application PCT/US08/77870, filed Sep. 26, 2008 and published Apr. 9, 2009 as WO 2009/045900, incorporated by reference herein in their entireties, disclose that brain-derived serotonin (hereafter abbreviated BDS) has the opposite effect as peripheral serotonin. Elevated BDS increases bone mass by acting through HT2C receptors on target neurons in the hypothalamus. Thus, some embodiments of the present invention include administering a combination of therapeutic agents that includes one or more compounds disclosed herein that decrease peripheral serotonin and one or more agents that increase BDS. BDS can be increased by increasing the activity of tryptophan hydroxylase 2 (TPH2), the enzyme responsible for the first step of serotonin synthesis in neurons of the brain stem, and by administering agonists of the HT2C serotonin receptor in the brain.

Other methods disclosed herein include steps relating to identifying or diagnosing a person at risk of developing a low bone mass disease such as osteoporosis by determining if the serum level of serotonin in the periphery is abnormally high (about 25% or more) compared to normal individuals, taking into account the age, gender, or other factors that affect serum serotonin levels. Such a person at risk may be treated with one or more compounds disclosed herein that decrease serum serotonin to prevent the low bone mass disease from developing or from progressing. Those of skill in the art will understand that serum serotonin levels may vary among individuals depending on certain factors and will be able to take those factors into account to determine whether a person has abnormally high serum serotonin levels. One range which those skilled in the art may consider to be normal serum serotonin levels is 101-283 ng/ml (nanograms per milliliter).

Since elevated serum serotonin may not be the only cause of diseases associated with low bone mass, methods other than those measuring serum serotonin levels may also be used to determine if a person having or suspected of having a low bone mass disease such as osteoporosis should be treated with drugs that decrease serum serotonin.

The present invention provides a method of lowering serum serotonin levels in a patient known or suspected to be in need of lowering of serum serotonin levels comprising administering to the patient known or suspected to be in need of lowering of serum serotonin levels a TPH1 inhibitor disclosed herein, optionally with a serotonin receptor antagonist.

The present invention also provides a method of treating or preventing a low bone mass disease in a patient known or suspected to be in need of such treatment or prevention comprising administering to the patient known or suspected to be in need of such treatment or prevention a therapeutically effective amount of one or more compounds disclosed herein that lower the level of serum serotonin.

In preferred embodiments, the compounds disclosed herein that are TPH1 inhibitors do not cross the blood brain barrier. In other embodiments, compounds disclosed herein that are TPH1 inhibitors do not significantly inhibit TPH2.

In certain embodiments, the compound of the present invention is a TPH1 inhibitor that is a sulfonic acid or a sulfonamide selected from the following or from pharmaceutically acceptable salts or solvates thereof:

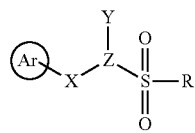
(a)

where Ar is a structure comprising 1-4 optionally substituted linked cycloalkyl, aryl, or heterocycle rings; R is hydroxyl, $NH_2$, or $OR_1$; $R_1$ is hydrogen or lower alkyl; X is —$CH_2$— or N; Y is hydrogen or $NH_2$; and Z is either (a) CH or (b) Z and Y are not present, i.e., X is directly bound to S. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

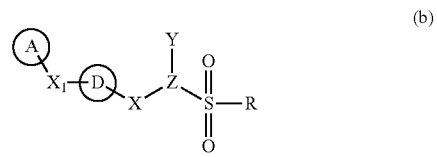
(b)

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; R is hydroxyl, $NH_2$, or $OR_1$; $R_1$ is hydrogen or lower alkyl; X is —$CH_2$— or N; Y is hydrogen or $NH_2$; Z is either (a) CH or (b) Z and Y are not present, i.e., X is directly bound to S; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; and each $R_5$ is independently hydrogen or optionally substituted alkyl or aryl. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

In some compounds, R is hydroxyl or $NH_2$, X is —$CH_2$—, Y is $NH_2$, Z is CH, $X_1$ is —C($R_3R_4$)O—, $R_3$ is hydrogen, and $R_4$ is substituted alkyl, preferably trifluoromethyl.

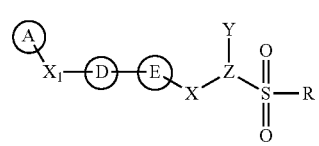
(c)

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; R is hydroxyl, $NH_2$, or $OR_1$; $R_1$ is hydrogen or lower alkyl; X is —$CH_2$— or N; Y is hydrogen or $NH_2$; Z is either (a) CH or (b) Z and Y are not present, i.e., X is directly bound to S; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; and each $R_5$ is independently hydrogen or optionally substituted alkyl or aryl. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

In some compounds, R is hydroxyl or $NH_2$, X is —$CH_2$—, Y is $NH_2$, Z is CH, $X_1$ is —$C(R_3R_4)O$—, $R_3$ is hydrogen, and $R_4$ is substituted alkyl, preferably trifluoromethyl.

In some compounds, A is fluoro-substituted biphenyl, R is hydroxyl or $NH_2$, X is —$CH_2$—, Y is $NH_2$, and Z is CH. In some of these compounds, R is hydroxyl, $X_1$ is —$C(R_3R_4)O$—, $R_3$ is hydrogen, and $R_4$ is substituted alkyl. In some of these compounds, A is 3'-fluorobiphenyl. In some of these compounds, $R_4$ is halo-substituted methyl. In some of these compounds, D is substituted pyrimidinyl and E is phenyl. In some of these compounds, D is 2-substituted pyrimidinyl. In some of these compounds, D is 2-amino pyrimidinyl.

In some compounds, A is fluoro-substituted biphenyl, R is hydroxyl or $NH_2$, X is —$CH_2$—, Y is $NH_2$, and Z is CH. In some of these compounds, R is $NH_2$, $X_1$ is —$C(R_3R_4)O$—, $R_3$ is hydrogen, and $R_4$ is substituted alkyl. In some of these compounds, A is 3'-fluorobiphenyl. In some of these compounds, $R_4$ is halo-substituted methyl. In some of these compounds, D is substituted pyrimidinyl and E is phenyl. In some of these compounds, D is 2-substituted pyrimidinyl. In some of these compounds, D is 2-amino pyrimidinyl.

In some compounds, A is fluoro-substituted biphenyl, R is hydroxyl or $NH_2$, X is N, and Z and Y are not present. In some of these compounds, R is $NH_2$, $X_1$ is —$C(R_3R_4)O$—, $R_3$ is hydrogen, and $R_4$ is substituted alkyl. In some of these compounds, A is 3'-fluorobiphenyl. In some of these compounds, $R_4$ is halo-substituted methyl. In some of these compounds, D is substituted pyrimidinyl and E is phenyl. In some of these compounds, D is 2-substituted pyrimidinyl. In some of these compounds, D is 2-amino pyrimidinyl.

In some compounds, A is optionally substituted biphenyl, $X_1$ is —$C(R_3R_4)O$, $R_3$ is hydrogen, $R_4$ is optionally substituted lower alkyl, D is optionally substituted pyrimidinyl, E is phenyl, X is —$CH_2$—, Y is $NH_2$, and Z is CH. In some of these compounds, R is hydroxyl. In some of these compounds, A is 2'-, 3'-, 4'-, 5', or 6'-halo-substituted biphenyl, $X_1$ is —$C(R_3R_4)O$—, $R_3$ is hydrogen, $R_4$ is halo-substituted methyl or ethyl, D is 2-substituted pyrimidinyl, and E is phenyl. In some of these compounds, A is 2'-, 3'-, 4'-, 5', or 6'-fluoro-substituted biphenyl, $X_1$ is —$C(R_3R_4)O$—, $R_3$ is hydrogen, $R_4$ is fluoro-substituted methyl, and D is 2-amino substituted pyrimidinyl.

In some compounds, A is optionally substituted biphenyl, $X_1$ is —$C(R_3R_4)O$, $R_3$ is hydrogen, $R_4$ is optionally substituted lower alkyl, D is optionally substituted pyrimidinyl, E is phenyl, X is —$CH_2$—, Y is $NH_2$, and Z is CH. In some of these compounds, R is $NH_2$. In some of these compounds, A is 2'-, 3'-, 4'-, 5', or 6'-halo-substituted biphenyl, $X_1$ is —$C(R_3R_4)O$—, $R_3$ is hydrogen, $R_4$ is halo-substituted methyl or ethyl, D is 2-substituted pyrimidinyl, and E is phenyl. In some of these compounds, A is 2'-, 3'-, 4'-, 5', or 6'-fluoro-substituted biphenyl, $X_1$ is —$C(R_3R_4)O$—, $R_3$ is hydrogen, $R_4$ is fluoro-substituted methyl, and D is 2-amino substituted pyrimidinyl.

In some compounds, A is optionally substituted biphenyl, $X_1$ is —$C(R_3R_4)O$, $R_3$ is hydrogen, $R_4$ is optionally substituted lower alkyl, D is optionally substituted pyrimidinyl, E is phenyl, R is hydroxyl or $NH_2$, X is N, and Z and Y are not present. In some of these compounds, R is $NH_2$. In some of these compounds, A is 2'-, 3'-, 4'-, 5', or 6'-halo-substituted biphenyl, $X_1$ is —$C(R_3R_4)O$—, $R_3$ is hydrogen, $R_4$ is halo-substituted methyl or ethyl, D is 2-substituted pyrimidinyl, and E is phenyl. In some of these compounds, A is 2'-, 3'-, 4'-, 5', or 6'-fluoro-substituted biphenyl, $X_1$ is —$C(R_3R_4)O$—, $R_3$ is hydrogen, $R_4$ is fluoro-substituted methyl, and D is 2-amino substituted pyrimidinyl.

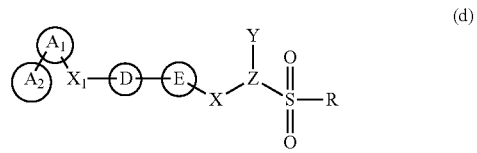

(d)

where each of $A_1$ and $A_2$ is independently a monocyclic optionally substituted cycloalkyl, aryl, or heterocycle; $X_1$ is a bond (i.e., $A_1$ is directly bound to D), —O—, —S—, —C(O)—, —$C(R_4)$=, =$C(R_4)$—, —$C(R_3R_4)$—, —$C(R_4)$=$C(R_4)$—, —$N(R_5)$—, —$N(R_5)C(O)N(R_5)$—, —$C(R_3R_4)N(R_5)$—, —$N(R_5)C(R_3R_4)$—, —$ONC(R_3)$—, —$C(R_3)NO$—, —$C(R_3R_4)O$—, —$OC(R_3R_4)$—, —$S(O_2)$—, —$S(O_2)N(R_5)$—, —$N(R_5)S(O_2)$—, —$C(R_3R_4)S(O_2)$—, or —$S(O_2)C(R_3R_4)$—; D is optionally substituted aryl or heterocycle; E is optionally substituted aryl or heterocycle; R is hydroxyl, $NH_2$, or $OR_1$; $R_1$ is hydrogen or lower alkyl; X is —$CH_2$— or N; Y is hydrogen or $NH_2$; Z is either (a) CH or (b) Z and Y are not present, i.e., X is directly bound to S; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; and each $R_5$ is independently hydrogen or optionally substituted alkyl or aryl. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

Compounds encompassed by the formula immediately above include those wherein $A_1$ and/or $A_2$ is optionally substituted cycloalkyl (e.g., 6-membered and 5-membered). In some, $A_1$ and/or $A_2$ is optionally substituted aryl (e.g., phenyl or naphthyl). In others, $A_1$ and/or $A_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

Particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

Particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

In some compounds, R is hydroxyl or $NH_2$, X is —$CH_2$—, Y is $NH_2$, Z is CH, $X_1$ is —$C(R_3R_4)O$—, $R_3$ is hydrogen, and $R_4$ is substituted alkyl, preferably trifluoromethyl.

In some compounds, $X_1$ is a bond or S. In others, $X_1$ is —$C(R_4)$=, =$C(R_4)$—, —$C(R_3R_4)$—, —$C(R_4)$=$C(R_4)$—, or —C≡C—, and, for example, $R_4$ is independently hydrogen or optionally substituted alkyl. In some of these compounds, X is —$CH_2$—, Y is $NH_2$, and Z is CH. In some of these compounds, R is hydroxyl.

In some compounds, $X_1$ is a bond or S. In others, $X_1$ is —$C(R_4)$=, =$C(R_4)$—, —$C(R_3R_4)$—, —$C(R_4)$=$C(R_4)$—, or —C≡C—, and, for example, $R_4$ is independently hydrogen or optionally substituted alkyl. In some of these compounds, X is —$CH_2$—, Y is $NH_2$, and Z is CH. In some of these compounds, R is $NH_2$.

In some compounds, $X_1$ is a bond or S. In others, $X_1$ is —$C(R_4)$=, =$C(R_4)$—, —$C(R_3R_4)$—, —$C(R_4)$=$C(R_4)$—, or —C≡C—, and, for example, $R_4$ is independently hydrogen or optionally substituted alkyl. In some of these compounds, R is hydroxyl or $NH_2$, X is N, and Z and Y are not present. In some of these compounds, R is $NH_2$.

In some compounds, $X_1$ is —O—, —$C(R_3R_4)O$—, or —$OC(R_3R_4)$—, and, for example, $R_3$ is hydrogen or optionally substituted alkyl, and $R_4$ is hydrogen or optionally substituted alkyl. In some of these compounds, $R_3$ is hydrogen and $R_4$ is trifluoromethyl. In some of these compounds, X is —$CH_2$—, Y is $NH_2$, and Z is CH. In some of these compounds, R is hydroxyl.

In some compounds, $X_1$ is —O—, —$C(R_3R_4)O$—, or —$OC(R_3R_4)$—, and, for example, $R_3$ is hydrogen or optionally substituted alkyl, and $R_4$ is hydrogen or optionally substituted alkyl. In some of these compounds, $R_3$ is hydrogen and $R_4$ is trifluoromethyl. In some of these compounds, X is —$CH_2$—, Y is $NH_2$, and Z is CH. In some of these compounds, R is $NH_2$.

In some compounds, $X_1$ is —O—, —$C(R_3R_4)O$—, or —$OC(R_3R_4)$—, and, for example, $R_3$ is hydrogen or optionally substituted alkyl, and $R_4$ is hydrogen or optionally substituted alkyl. In some of these compounds, $R_3$ is hydrogen and $R_4$ is trifluoromethyl. In some of these compounds, R is hydroxyl or $NH_2$, X is N, and Z and Y are not present. In some of these compounds, R is $NH_2$.

In some compounds, $X_1$ is —$S(O_2)$—, —$S(O_2)N(R_5)$—, —$N(R_5)S(O_2)$—, —$C(R_3R_4)S(O_2)$—, or —$S(O_2)C(R_3R_4)$—, and, for example, $R_3$ is hydrogen or optionally substituted alkyl, $R_4$ is hydrogen or optionally substituted alkyl, and $R_5$ is hydrogen or optionally substituted alkyl. In some of these compounds, X is —$CH_2$—, Y is $NH_2$, and Z is CH. In some of these compounds, R is hydroxyl.

In some compounds, $X_1$ is —$S(O_2)$—, —$S(O_2)N(R_5)$—, —$N(R_5)S(O_2)$—, —$C(R_3R_4)S(O_2)$—, or —$S(O_2)C(R_3R_4)$—, and, for example, $R_3$ is hydrogen or optionally substituted alkyl, $R_4$ is hydrogen or optionally substituted alkyl, and $R_5$ is hydrogen or optionally substituted alkyl. In some of these compounds, X is —$CH_2$—, Y is $NH_2$, and Z is CH. In some of these compounds, R is $NH_2$.

In some compounds, $X_1$ is —$S(O_2)$—, —$S(O_2)N(R_5)$—, —$N(R_5)S(O_2)$—, —$C(R_3R_4)S(O_2)$—, or —$S(O_2)C(R_3R_4)$—, and, for example, $R_3$ is hydrogen or optionally substituted alkyl, $R_4$ is hydrogen or optionally substituted alkyl, and $R_5$ is hydrogen or optionally substituted alkyl. In some of these compounds, R is hydroxyl or $NH_2$, X is N, and Z and Y are not present. In some of these compounds, R is $NH_2$.

In some compounds, $X_1$ is —$N(R_5)$—, —$N(R_5)C(O)N(R_5)$—, —$C(R_3R_4)N(R_5)$—, or —$N(R_5)C(R_3R_4)$—, and, for example, $R_3$ is hydrogen or optionally substituted alkyl, $R_4$ is hydrogen or optionally substituted alkyl, and each $R_5$ is independently hydrogen or optionally substituted alkyl. In some of these compounds, X is —$CH_2$—, Y is $NH_2$, and Z is CH. In some of these compounds, R is hydroxyl.

In some compounds, $X_1$ is —$N(R_5)$—, —$N(R_5)C(O)N(R_5)$—, —$C(R_3R_4)N(R_5)$—, or —$N(R_5)C(R_3R_4)$—, and, for example, $R_3$ is hydrogen or optionally substituted alkyl, $R_4$ is hydrogen or optionally substituted alkyl, and each $R_5$ is independently hydrogen or optionally substituted alkyl. In some of these compounds, X is —$CH_2$—, Y is $NH_2$, and Z is CH. In some of these compounds, R is $NH_2$.

In some compounds, $X_1$ is —$N(R_5)$—, —$N(R_5)C(O)N(R_5)$—, —$C(R_3R_4)N(R_5)$—, or —$N(R_5)C(R_3R_4)$—, and, for example, $R_3$ is hydrogen or optionally substituted alkyl, $R_4$ is hydrogen or optionally substituted alkyl, and each $R_5$ is independently hydrogen or optionally substituted alkyl. In some of these compounds, R is hydroxyl or $NH_2$, X is N, and Z and Y are not present. In some of these compounds, R is $NH_2$.

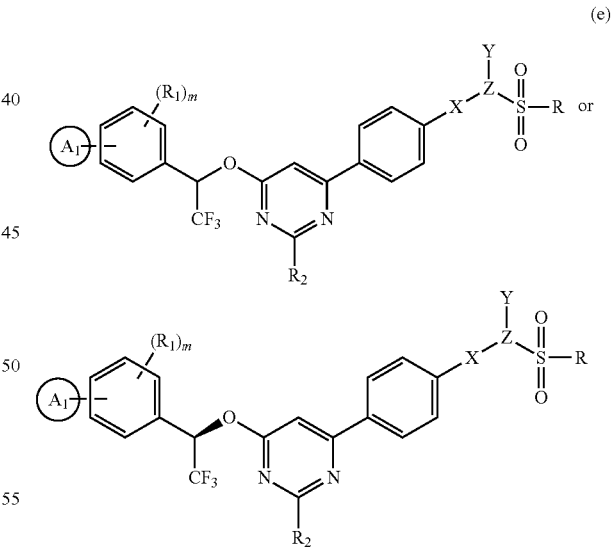

(e)

where $A_1$ is optionally substituted heterocycle; R is hydroxyl, $NH_2$, or $OR_3$; $R_3$ is hydrogen or lower alkyl; X is —$CH_2$— or N; Y is hydrogen or $NH_2$; Z is either (a) CH or (b) Z and Y are not present, i.e., X is directly bound to S; each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

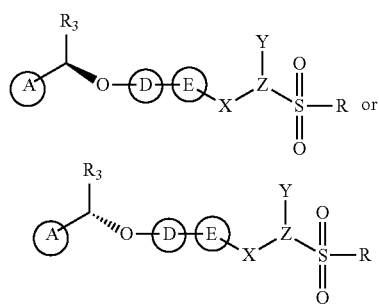

(f)

where A is optionally substituted cycloalkyl, aryl, or heterocycle; D is optionally substituted aryl or heterocycle; E is optionally substituted aryl or heterocycle; R is hydroxyl, $NH_2$, or $OR_2$; $R_2$ is hydrogen or lower alkyl; X is —$CH_2$— or N; Y is hydrogen or $NH_2$; Z is either (a) CH or (b) Z and Y are not present, i.e., X is directly bound to S; and $R_3$ is trifluoromethyl. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

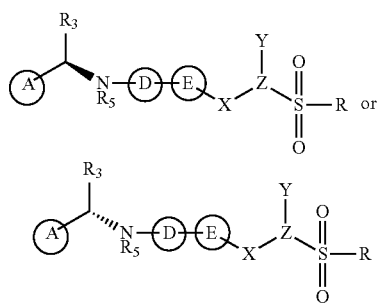

(g)

where A is optionally substituted cycloalkyl, aryl, or heterocycle; D is optionally substituted aryl or heterocycle; E is optionally substituted aryl or heterocycle; R is hydroxyl, $NH_2$, or $OR_1$; $R_1$ is hydrogen or lower alkyl; X is —$CH_2$— or N; Y is hydrogen or $NH_2$; Z is either (a) CH or (b) Z and Y are not present, i.e., X is directly bound to S; $R_3$ is hydrogen; and $R_5$ is hydrogen or optionally substituted alkyl or aryl. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

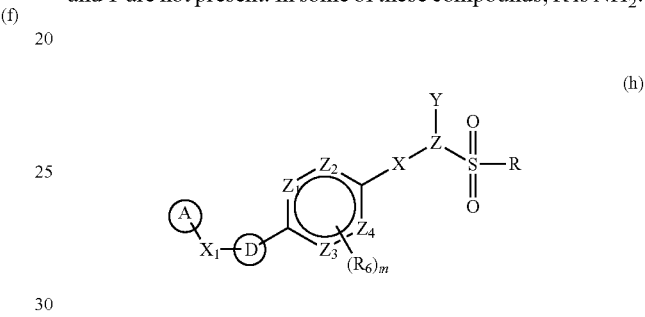

(h)

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; each of $Z_1$, $Z_2$, $Z_3$, and $Z_4$ is independently N or $CR_6$; R is hydroxyl, $NH_2$, or $OR_1$; $R_1$ is hydrogen or lower alkyl; X is —$CH_2$— or N; Y is hydrogen or $NH_2$; Z is either (a) CH or (b) Z and Y are not present, i.e., X is directly bound to S; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; and m is 1-4. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

(i)

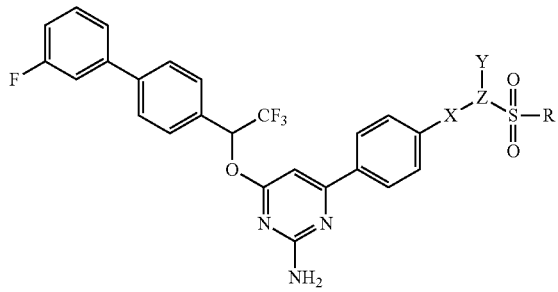

where R is hydroxyl, $NH_2$, or $OR_2$; $R_2$ is hydrogen or lower alkyl; X is —$CH_2$— or N; Y is hydrogen or $NH_2$; and Z is either (a) CH or (b) Z and Y are not present, i.e., X is directly bound to S. Where Z is CH and Y is $NH_2$, the carbon atom of Z is an asymmetric carbon that may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydroxyl or $NH_2$, X is —$CH_2$—, Y is $NH_2$, and Z is CH. In some of these compounds, R is hydroxyl. In others of these compounds, R is $NH_2$.

In some compounds, R is hydroxyl or $NH_2$, X is N, and Z and Y are not present. In some of these compounds, R is $NH_2$.

(j)

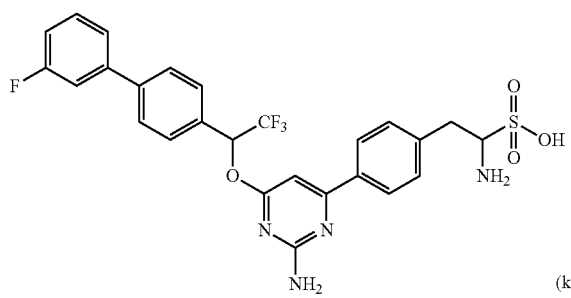

(k)

(l)

In certain embodiments, the compound of the present invention is a TPH1 inhibitor that is an α-amino carboxylic acid or an α-amino carboxylic acid ester having a 3, 4, or 5-membered ring selected from the following or from pharmaceutically acceptable salts or solvates thereof:

(m)

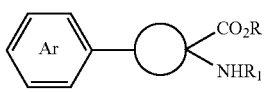

where Ar is a structure comprising 1-4 optionally substituted linked cycloalkyl, aryl, or heterocycle rings; ○ represents a 3, 4, or 5-membered optionally substituted cycloalkyl or a 4 or 5-membered optionally substituted heterocycle; R is hydrogen or lower alkyl; and $R_1$ is hydrogen or lower alkyl. Where the carbon that bears the $CO_2R$ and $NHR_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form. In some compounds, Ar comprises 1 ring; in some compounds, Ar comprises 2 rings; in some compounds, Ar comprises 3 rings; in some compounds, Ar comprises 4 rings.

(n)

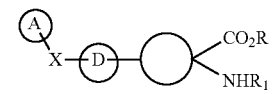

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; R is hydrogen or lower alkyl; $R_1$ is hydrogen or lower alkyl; each $R_3$ is independently hydrogen, alkoxy, amino, cyano, halogen, hydroxyl, or optionally substituted alkyl; each $R_4$ independently is hydrogen, alkoxy, amino, cyano, halogen, hydroxyl, or optionally substituted alkyl or aryl; each $R_5$ is independently hydrogen or optionally substituted alkyl or aryl; and ○ represents a 3, 4, or 5-membered optionally substituted cycloalkyl or a 4 or 5-membered optionally substituted heterocycle. Where the carbon that bears the $CO_2R$ and $NHR_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, ○ is cyclopropyl, cyclobutyl, or cyclopentyl. In some of these compounds, ○ is cyclopropyl.

In some compounds, R is methyl, ethyl, or isopropyl.

In some compounds, ○ is cyclopropyl, R is methyl, and $R_1$ is hydrogen.

In some compounds, ○ is cyclopropyl, cyclobutyl, or cyclopentyl, R is methyl, $R_1$ is hydrogen, X is —C($R_3R_4$)

O—, $R_3$ is hydrogen, and $R_4$ is substituted alkyl, preferably trifluoromethyl.

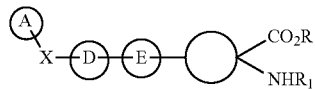
(o)

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; R is hydrogen or lower alkyl; $R_1$ is hydrogen or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and ◯ represents a 3, 4, or 5-membered optionally substituted cycloalkyl or a 4 or 5-membered optionally substituted heterocycle. Where the carbon that bears the $CO_2R$ and $NHR_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, ◯ is cyclopropyl, cyclobutyl, or cyclopentyl. In some of these compounds, ◯ is cyclopropyl.

In some compounds, R is methyl, ethyl, or isopropyl.

In some compounds, ◯ is cyclopropyl, R is methyl, and $R_1$ is hydrogen.

In some compounds, A is fluoro-substituted biphenyl, ◯ is cyclopropyl, R is hydrogen or methyl, $R_1$ is hydrogen, X is —C($R_3R_4$)O—, $R_3$ is hydrogen, and $R_4$ is substituted alkyl. In some of these compounds, A is 3'-fluorobiphenyl. In some of these compounds, $R_4$ is halo-substituted methyl. In some of these compounds, D is substituted pyrimidinyl and E is phenyl. In some of these compounds, D is 2-substituted pyrimidinyl. In some of these compounds, D is 2-amino pyrimidinyl.

In some compounds, A is optionally substituted biphenyl, X is —C($R_3R_4$)O—, $R_3$ is hydrogen, $R_4$ is optionally substituted lower alkyl, D is optionally substituted pyrimidinyl, E is phenyl, ◯ is cyclopropyl or cyclobutyl, R is hydrogen or methyl, and $R_1$ is hydrogen. In some of these compounds, ◯ is cyclopropyl. In some of these compounds, A is 2'-, 3'-, 4'-, 5', or 6'-halo-substituted biphenyl, X is —C($R_3R_4$)O—, $R_3$ is hydrogen, $R_4$ is halo-substituted methyl or ethyl, D is 2-substituted pyrimidinyl, and E is phenyl. In some of these compounds, A is 2'-, 3'-, 4'-, 5', or 6'-fluoro-substituted biphenyl, X is —C($R_3R_4$)O—, $R_3$ is hydrogen, $R_4$ is fluoro-substituted methyl, and D is 2-amino substituted pyrimidinyl.

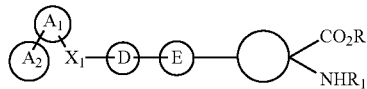
(p)

where each of $A_1$ and $A_2$ is independently a monocyclic optionally substituted cycloalkyl, aryl, or heterocycle; $X_1$ is a bond (i.e., $A_1$ is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; R is hydrogen or lower alkyl; $R_1$ is hydrogen or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and ◯ represents a 3, 4, or 5-membered optionally substituted cycloalkyl or a 4 or 5-membered optionally substituted heterocycle. Where the carbon that bears the $CO_2R$ and $NHR_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

Compounds encompassed by the formula immediately above include those wherein $A_1$ and/or $A_2$ is optionally substituted cycloalkyl (e.g., 6-membered and 5-membered). In some, $A_1$ and/or $A_2$ is optionally substituted aryl (e.g., phenyl or naphthyl). In others, $A_1$ and/or $A_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

Particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

Particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

In some compounds, ◯ is cyclopropyl, cyclobutyl, or cyclopentyl. In some of these compounds, ◯ is cyclopropyl.

In some compounds, R is methyl, ethyl, or isopropyl.

In some compounds, ◯ is cyclopropyl, R is methyl, and $R_1$ is hydrogen.

In some compounds, $X_1$ is a bond or S. In others, $X_1$ is —C($R_4$)=, =C($R_4$)—, —C($R_3R_4$)—, —C($R_4$)=C($R_4$)—, or —C≡C—, and, for example, $R_4$ is independently hydrogen or optionally substituted alkyl. In some of these compounds, ◯ is cyclopropyl, R is methyl, and $R_1$ is hydrogen.

In some compounds, $X_1$ is —O—, —C($R_3R_4$)O—, or —OC($R_3R_4$)—, and, for example, $R_3$ is hydrogen or optionally substituted alkyl and $R_4$ is hydrogen or optionally substituted alkyl. In some of these compounds, $R_3$ is hydrogen and $R_4$ is trifluoromethyl. In some of these compounds, ○ is cyclopropyl, R is methyl, and $R_1$ is hydrogen.

In some compounds, $X_1$ is —S($O_2$)—, —S($O_2$)N($R_5$)—, —N($R_5$)S($O_2$)—, —C($R_3R_4$)S($O_2$)—, or —S($O_2$)C($R_3R_4$)—, and, for example, $R_3$ is hydrogen or optionally substituted alkyl, $R_4$ is hydrogen or optionally substituted alkyl, and $R_5$ is hydrogen or optionally substituted alkyl. In some of these compounds, ○ is cyclopropyl, R is methyl, and $R_1$ is hydrogen.

In some compounds, $X_1$ is —N($R_5$)—, —N($R_5$)C(O)N($R_5$)—, —C($R_3R_4$)N($R_5$)—, or —N($R_5$)C($R_3R_4$)—, and, for example, $R_3$ is hydrogen or optionally substituted alkyl, $R_4$ is hydrogen or optionally substituted alkyl, and each $R_5$ is independently hydrogen or optionally substituted alkyl. In some of these compounds, ○ is cyclopropyl, R is methyl, and $R_1$ is hydrogen.

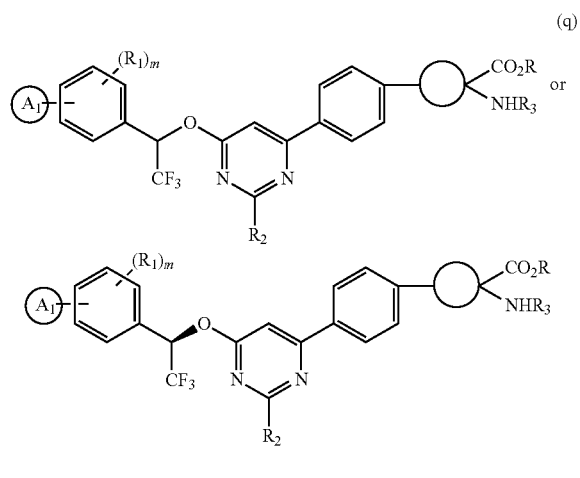

(q)

where $A_1$ is optionally substituted heterocycle; R is hydrogen or lower alkyl; each $R_1$ is independently halogen, hydrogen, C(O)$R_A$, O$R_A$, N$R_BR_C$, S($O_2$)$R_A$, or optionally substituted alkyl, alkyl-aryl or alkyl-heterocycle; $R_2$ is halogen, hydrogen, C(O)$R_A$, O$R_A$, N$R_BR_C$, S($O_2$)$R_A$, or optionally substituted alkyl, alkyl-aryl or alkyl-heterocycle; $R_3$ is hydrogen or lower alkyl; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; ○ represents a 3, 4, or 5-membered optionally substituted cycloalkyl or a 4 or 5-membered optionally substituted heterocycle; and m is 1-4. Where the carbon that bears the $CO_2R$ and $NHR_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, ○ is cyclopropyl, cyclobutyl, or cyclopentyl. In some of these compounds, ○ is cyclopropyl.

In some compounds, R is methyl, ethyl, or isopropyl.

In some compounds, ○ is cyclopropyl, R is methyl, and $R_1$ is hydrogen.

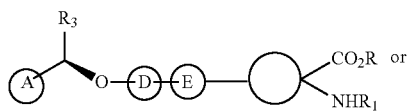

(r)

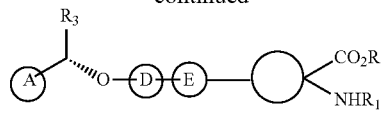

where A is optionally substituted cycloalkyl, aryl, or heterocycle; D is optionally substituted aryl or heterocycle; E is optionally substituted aryl or heterocycle; R is hydrogen or lower alkyl; $R_1$ is hydrogen or lower alkyl; $R_3$ is trifluoromethyl; and ○ represents a 3, 4, or 5-membered optionally substituted cycloalkyl or a 4 or 5-membered optionally substituted heterocycle. Where the carbon that bears the $CO_2R$ and $NHR_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, ○ is cyclopropyl, cyclobutyl, or cyclopentyl. In some of these compounds, ○ is cyclopropyl.

In some compounds, R is methyl, ethyl, or isopropyl.

In some compounds, ○ is cyclopropyl, R is methyl, and $R_1$ is hydrogen.

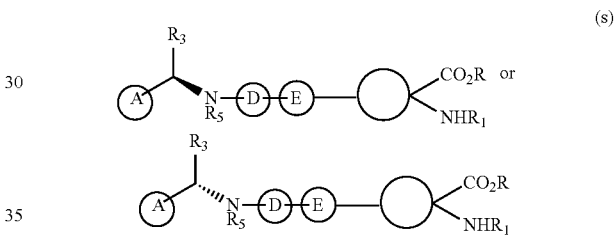

(s)

where A is optionally substituted cycloalkyl, aryl, or heterocycle; D is optionally substituted aryl or heterocycle; E is optionally substituted aryl or heterocycle; R is hydrogen or lower alkyl; $R_1$ is hydrogen or lower alkyl; ○ represents a 3, 4, or 5-membered optionally substituted cycloalkyl or a 4 or 5-membered optionally substituted heterocycle; $R_3$ is hydrogen; and $R_5$ is hydrogen or optionally substituted alkyl or aryl. Where the carbon that bears the $CO_2R$ and $NHR_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, ○ is cyclopropyl, cyclobutyl, or cyclopentyl. In some of these compounds, ○ is cyclopropyl.

In some compounds, R is methyl, ethyl, or isopropyl.

In some compounds, ○ is cyclopropyl, R is methyl, and $R_1$ is hydrogen.

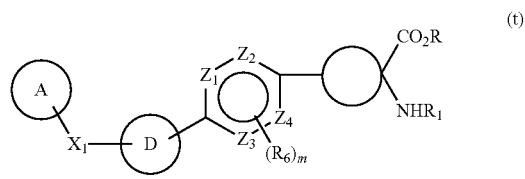

(t)

where A is optionally substituted cycloalkyl, aryl, or heterocycle; $X_1$ is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N (R$_5$)—, —C(R$_3$R$_4$)N(R$_5$)—, —N(R$_5$)C(R$_3$R$_4$)—, —ONC (R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$) S(O$_2$)—, or —S(O$_2$)C(R$_3$R$_4$)—; D is optionally substituted aryl or heterocycle; each of Z$_1$, Z$_2$, Z$_3$, and Z$_4$ is independently N or CR$_6$; R is hydrogen or lower alkyl; R$_1$ is hydrogen or lower alkyl; ○ represents a 3, 4, or 5-membered optionally substituted cycloalkyl or a 4 or 5-membered optionally substituted heterocycle; each R$_3$ is independently hydrogen, alkoxy, amino, cyano, halogen, hydroxyl, or optionally substituted alkyl; each R$_4$ is independently hydrogen, alkoxy, amino, cyano, halogen, hydroxyl, or optionally substituted alkyl or aryl; each R$_5$ is independently hydrogen or optionally substituted alkyl or aryl; each R$_6$ is independently hydrogen, cyano, halogen, OR$_7$, NR$_8$R$_9$, amino, hydroxyl, or optionally substituted alkyl, alkyl-aryl or alkyl-heterocycle; each R$_7$ is independently hydrogen or optionally substituted alkyl, alkyl-aryl or alkyl-heterocycle; each R$_8$ is independently hydrogen or optionally substituted alkyl, alkyl-aryl or alkyl-heterocycle; each R$_9$ is independently hydrogen or optionally substituted alkyl, alkyl-aryl or alkyl-heterocycle; and m is 1-4.

In some compounds, ○ is cyclopropyl, cyclobutyl, or cyclopentyl. In some of these compounds, ○ is cyclopropyl.

In some compounds, R is methyl, ethyl, or isopropyl.

In some compounds, ○ is cyclopropyl, R is methyl, and R$_1$ is hydrogen.

(u)

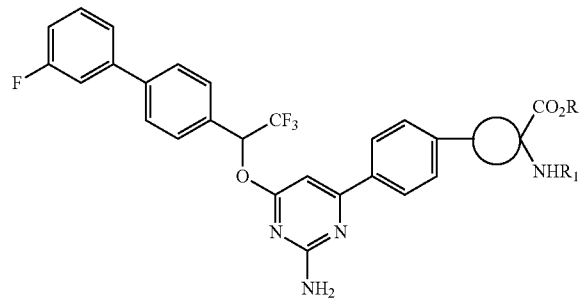

where ○ represents a 3, 4, or 5-membered optionally substituted cycloalkyl or a 4 or 5-membered optionally substituted heterocycle; R is hydrogen or lower alkyl; and R$_1$ is hydrogen or lower alkyl. Where the carbon that bears the CO$_2$R and NHR$_1$ groups is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, ○ is cyclopropyl, cyclobutyl, or cyclopentyl. In some of these compounds, R is hydrogen, methyl, ethyl, or isopropyl, and R$_1$ is hydrogen. In some of these compounds, ○ is cyclopropyl, and R is hydrogen or methyl. In some of these compounds, R is hydrogen.

(v)

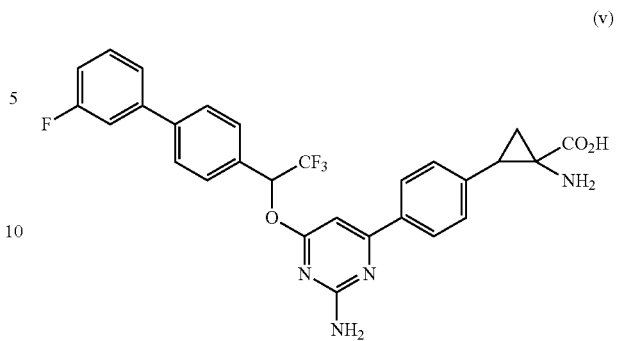

In certain embodiments, the compound of the present invention is a TPH1 inhibitor having a 6, 7, or 8-membered heterocycle linked to an acidic functional group selected from the following or from pharmaceutically acceptable salts or solvates thereof:

(w)

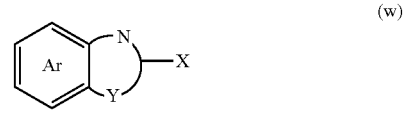

where Ar is a structure comprising 1-4 optionally substituted linked cycloalkyl, aryl, or heterocycle rings; X is CO$_2$R, SO$_3$R, BOROR$_1$, or COCO$_2$R; Y is —CH$_2$—, N, S, or O; R is hydrogen or lower alkyl; R$_1$ is hydrogen or lower alkyl; and N and Y form part of a 6, 7, or 8-membered heterocycle fused to Ar. In some compounds, Ar comprises 1 ring; in some compounds, Ar comprises 2 rings; in some compounds, Ar comprises 3 rings; in some compounds, Ar comprises 4 rings. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, X is CO$_2$R, Y is O, R is hydrogen or methyl, and N and Y form part of a 7-membered ring where N is linked to the carbon bearing X and Y is separated from the carbon bearing X by a methylene. In some of these compounds, R is hydrogen.

In some compounds, X is SO$_3$R, Y is O, R is hydrogen or methyl, and N and Y form part of a 7-membered ring where N is linked to the carbon bearing X and Y is separated from the carbon bearing X by a methylene. In some of these compounds, R is hydrogen.

(x)

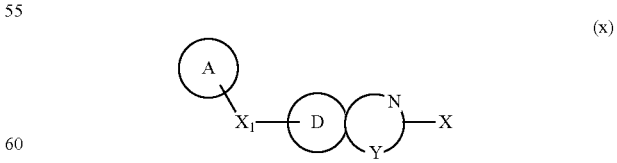

where A is optionally substituted cycloalkyl, aryl, or heterocycle; X$_1$ is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N (R$_5$)—, —C(R$_3$R$_4$)N(R$_5$)—, —N(R$_5$)C(R$_3$R$_4$)—, —ONC (R₃)—, —C(R₃)NO—, —C(R₃R₄)O—, —OC(R₃R₄)—, —S(O₂)—, —S(O₂)N(R₅)—, —N(R₅)S(O₂)—, —C(R₃R₄)S(O₂)—, or —S(O₂)C(R₃R₄)—; D is optionally substituted aryl or heterocycle; X is CO₂R, SO₃R, BOROR₁, or COCO₂R; Y is —CH₂—, N, S, or O; R is hydrogen or lower alkyl; R₁ is hydrogen or lower alkyl; N and Y form part of a 6, 7, or 8-membered heterocycle fused to D; each R₃ is independently hydrogen, alkoxy, amino, cyano, halogen, hydroxyl, or optionally substituted alkyl; each R₄ is independently hydrogen, alkoxy, amino, cyano, halogen, hydroxyl, or optionally substituted alkyl or aryl; each R₅ is independently hydrogen or optionally substituted alkyl or aryl. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, X is CO₂R, Y is O, R is hydrogen or methyl, and N and Y form part of a 7-membered ring where N is linked to the carbon bearing X and Y is separated from the carbon bearing X by a methylene. In some of these compounds, R is hydrogen. In some of these compounds, X₁ is —C(R₃R₄)O—, R₃ is hydrogen, and R₄ is substituted alkyl, preferably trifluoromethyl.

In some compounds, X is SO₃R, Y is O, R is hydrogen or methyl, and N and Y form part of a 7-membered ring where N is linked to the carbon bearing X and Y is separated from the carbon bearing X by a methylene. In some of these compounds, R is hydrogen. In some of these compounds, X₁ is —C(R₃R₄)O—, R₃ is hydrogen, and R₄ is substituted alkyl, preferably trifluoromethyl.

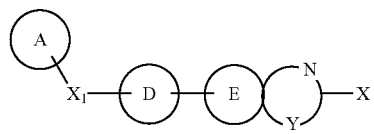

(y)

where A is optionally substituted cycloalkyl, aryl, or heterocycle; X₁ is a bond (i.e., A is directly bound to D), —O—, —S—, —C(O)—, —C(R₄)=, =C(R₄)—, —C(R₃R₄)—, —C(R₄)=C(R₄)—, —C≡C—, —N(R₅)—, —N(R₅)C(O)N(R₅)—, —C(R₃R₄)N(R₅)—, —N(R₅)C(R₃R₄)—, —ONC(R₃)—, —C(R₃)NO—, —C(R₃R₄)O—, —OC(R₃R₄)—, —S(O₂)—, —S(O₂)N(R₅)—, —N(R₅)S(O₂)—, —C(R₃R₄)S(O₂)—, or —S(O₂)C(R₃R₄)—; D is optionally substituted aryl or heterocycle; E is optionally substituted aryl or heterocycle; X is CO₂R, SO₃R, BOROR₁, or COCO₂R; Y is —CH₂—, N, S, or O; R is hydrogen or lower alkyl; R₁ is hydrogen or lower alkyl; N and Y form part of a 6, 7, or 8-membered heterocycle fused to D; each R₃ is independently hydrogen, alkoxy, amino, cyano, halogen, hydroxyl, or optionally substituted alkyl; each R₄ is independently hydrogen, alkoxy, amino, cyano, halogen, hydroxyl, or optionally substituted alkyl or aryl; and each R₅ is independently hydrogen or optionally substituted alkyl or aryl. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, X is CO₂R, Y is O, R is hydrogen or methyl, and N and Y form part of a 7-membered ring where N is linked to the carbon bearing X and Y is separated from the carbon bearing X by a methylene. In some of these compounds, R is hydrogen. In some of these compounds, X₁ is —C(R₃R₄)O—, R₃ is hydrogen, and R₄ is substituted alkyl, preferably trifluoromethyl.

In some compounds, X is SO₃R, Y is O, R is hydrogen or methyl, and N and Y form part of a 7-membered ring where N is linked to the carbon bearing X and Y is separated from the carbon bearing X by a methylene. In some of these compounds, R is hydrogen. In some of these compounds, X₁ is —C(R₃R₄)O—, R₃ is hydrogen, and R₄ is substituted alkyl, preferably trifluoromethyl.

In some compounds, A is fluoro-substituted biphenyl, X is CO₂R or SO₃R, Y is O, R is hydrogen or methyl, N and Y form part of a 7-membered ring where N is linked to the carbon bearing X and Y is separated from the carbon bearing X by a methylene, X₁ is —C(R₃R₄)O—, R₃ is hydrogen, and R₄ is substituted alkyl. In some of these compounds, A is 3'-fluorobiphenyl, X is absent, and R is hydrogen. In some of these compounds, R₄ is halo-substituted methyl. In some of these compounds, D is substituted pyrimidinyl and E is phenyl. In some of these compounds, D is 2-substituted pyrimidinyl. In some of these compounds, D is 2-amino pyrimidinyl. In some of these compounds, X is CO₂R and R is hydrogen.

In some compounds, A is optionally substituted biphenyl, X₁ is —C(R₃R₄)O—, R₃ is hydrogen, R₄ is optionally substituted lower alkyl, D is optionally substituted pyrimidinyl, E is phenyl, X is SO₃R, Y is O, R is hydrogen or methyl, and N and Y form part of a 7-membered ring where N is linked to the carbon bearing X and Y is separated from the carbon bearing X by a methylene. In some of these compounds, X is absent. In some of these compounds, A is 2'-, 3'-, 4'-, 5', or 6'-halo-substituted biphenyl, R₄ is halo-substituted methyl or ethyl, and D is 2-substituted pyrimidinyl. In some of these compounds, A is 2'-, 3'-, 4'-, 5', or 6'-fluoro-substituted biphenyl, R₄ is fluoro-substituted methyl, and D is 2-amino substituted pyrimidinyl. In some of these compounds, R is hydrogen.

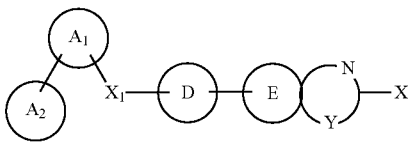

(z)

where each of A₁ and A₂ is independently a monocyclic optionally substituted cycloalkyl, aryl, or heterocycle; X₁ is a bond (i.e., A₁ is directly bound to D), —O—, —S—, —C(O)—, —C(R₄)=, =C(R₄)—, —C(R₃R₄)—, —C(R₄)=C(R₄)—, —C≡C—, —N(R₅)—, —N(R₅)C(O)N(R₅)—, —C(R₃R₄)N(R₅)—, —N(R₅)C(R₃R₄)—, —ONC(R₃)—, —C(R₃)NO—, —C(R₃R₄)O—, —OC(R₃R₄)—, —S(O₂)—, —S(O₂)N(R₅)—, —N(R₅)S(O₂)—, —C(R₃R₄)S(O₂)—, or —S(O₂)C(R₃R₄)—; D is optionally substituted aryl or heterocycle; E is optionally substituted aryl or heterocycle; X is CO₂R, SO₃R, BOROR₁, or COCO₂R; Y is —CH₂—, N, S, or O; R is hydrogen or lower alkyl; R₁ is hydrogen or lower alkyl; N and Y form part of a 6, 7, or 8-membered heterocycle fused to D; each R₃ is independently hydrogen, alkoxy, amino, cyano, halogen, hydroxyl, or optionally substituted alkyl; each R₄ is independently hydrogen, alkoxy, amino, cyano, halogen, hydroxyl, or optionally substituted alkyl or aryl; and each R₅ is independently hydrogen or optionally substituted alkyl or aryl. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

Compounds encompassed by the formula immediately above include those wherein $A_1$ and/or $A_2$ is optionally substituted cycloalkyl (e.g., 6-membered and 5-membered). In some, $A_1$ and/or $A_2$ is optionally substituted aryl (e.g., phenyl or naphthyl). In others, $A_1$ and/or $A_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

Particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

Particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

In some compounds, X is $CO_2R$, Y is O, R is hydrogen or methyl, and N and Y form part of a 7-membered ring where N is linked to the carbon bearing X and Y is separated from the carbon bearing X by a methylene. In some of these compounds, R is hydrogen. In some of these compounds, $X_1$ is —$C(R_3R_4)O$—, $R_3$ is hydrogen, and $R_4$ is substituted alkyl, preferably trifluoromethyl.

In some compounds, X is $SO_3R$, Y is O, R is hydrogen or methyl, and N and Y form part of a 7-membered ring where N is linked to the carbon bearing X and Y is separated from the carbon bearing X by a methylene. In some of these compounds, R is hydrogen. In some of these compounds, $X_1$ is —$C(R_3R_4)O$—, $R_3$ is hydrogen, and $R_4$ is substituted alkyl, preferably trifluoromethyl.

In some compounds, $X_1$ is a bond or S. In others, $X_1$ is —$C(R_4)$=, =$C(R_4)$—, —$C(R_3R_4)$—, —$C(R_4)$=$C(R_4)$—, or —C≡C—, and, for example, $R_4$ is independently hydrogen or optionally substituted alkyl. In some of these compounds, X is $CO_2R$, R is hydrogen or methyl, and N and Y form part of a 7-membered ring where N is linked to the carbon bearing X and Y is separated from the carbon bearing X by a methylene. In some of these compounds, R is hydrogen.

In some compounds, $X_1$ is a bond or S. In others, $X_1$ is —$C(R_4)$=, =$C(R_4)$—, —$C(R_3R_4)$—, —$C(R_4)$=$C(R_4)$—, or —C≡C—, and, for example, $R_4$ is independently hydrogen or optionally substituted alkyl. In some of these compounds, X is $SO_3R$, R is hydrogen or methyl, and N and Y form part of a 7-membered ring where N is linked to the carbon bearing X and Y is separated from the carbon bearing X by a methylene. In some of these compounds, R is hydrogen.

In some compounds, $X_1$ is —O—, —$C(R_3R_4)O$—, or —$OC(R_3R_4)$—, and, for example, $R_3$ is hydrogen or optionally substituted alkyl, and $R_4$ is hydrogen or optionally substituted alkyl. In some of these compounds, $R_3$ is hydrogen and $R_4$ is trifluoromethyl. In some of these compounds, X is $CO_2R$, R is hydrogen or methyl, and N and Y form part of a 7-membered ring where N is linked to the carbon bearing X and Y is separated from the carbon bearing X by a methylene. In some of these compounds, R is hydrogen.

In some compounds, $X_1$ is —O—, —$C(R_3R_4)O$—, or —$OC(R_3R_4)$—, and, for example, $R_3$ is hydrogen or optionally substituted alkyl, and $R_4$ is hydrogen or optionally substituted alkyl. In some of these compounds, $R_3$ is hydrogen and $R_4$ is trifluoromethyl. In some of these compounds, X is $SO_3R$, R is hydrogen or methyl, and N and Y form part of a 7-membered ring where N is linked to the carbon bearing X and Y is separated from the carbon bearing X by a methylene. In some of these compounds, R is hydrogen.

In some compounds, $X_1$ is —$S(O_2)$—, —$S(O_2)N(R_5)$—, —$N(R_5)S(O_2)$—, —$C(R_3R_4)S(O_2)$—, or —$S(O_2)C(R_3R_4)$—, and, for example, $R_3$ is hydrogen or optionally substituted alkyl, $R_4$ is hydrogen or optionally substituted alkyl, and $R_5$ is hydrogen or optionally substituted alkyl. In some of these compounds, X is $CO_2R$, R is hydrogen or methyl, and N and Y form part of a 7-membered ring where N is linked to the carbon bearing X and Y is separated from the carbon bearing X by a methylene. In some of these compounds, R is hydrogen.

In some compounds, $X_1$ is —$S(O_2)$—, —$S(O_2)N(R_5)$—, —$N(R_5)S(O_2)$—, —$C(R_3R_4)S(O_2)$—, or —$S(O_2)C(R_3R_4)$—, and, for example, $R_3$ is hydrogen or optionally substituted alkyl, $R_4$ is hydrogen or optionally substituted alkyl, and $R_5$ is hydrogen or optionally substituted alkyl. In some of these compounds, X is $SO_3R$, R is hydrogen or methyl, and N and Y form part of a 7-membered ring where N is linked to the carbon bearing X and Y is separated from the carbon bearing X by a methylene. In some of these compounds, R is hydrogen.

In some compounds, $X_1$ is —$N(R_5)$—, —$N(R_5)C(O)N(R_5)$—, —$C(R_3R_4)N(R_5)$—, or —$N(R_5)C(R_3R_4)$—, and, for example, $R_3$ is hydrogen or optionally substituted alkyl, $R_4$ is hydrogen or optionally substituted alkyl, and each $R_5$ is independently hydrogen or optionally substituted alkyl. In some of these compounds, X is $CO_2R$, R is hydrogen or methyl, and N and Y form part of a 7-membered ring where N is linked to the carbon bearing X and Y is separated from the carbon bearing X by a methylene. In some of these compounds, R is hydrogen.

In some compounds, $X_1$ is —$N(R_5)$—, —$N(R_5)C(O)N(R_5)$—, —$C(R_3R_4)N(R_5)$—, or —$N(R_5)C(R_3R_4)$—, and, for example, $R_3$ is hydrogen or optionally substituted alkyl, $R_4$ is hydrogen or optionally substituted alkyl, and each $R_5$ is independently hydrogen or optionally substituted alkyl. In some of these compounds, X is $SO_3R$, R is hydrogen or methyl, and N and Y form part of a 7-membered ring where N is linked to the carbon bearing X and Y is separated from the carbon bearing X by a methylene. In some of these compounds, R is hydrogen.

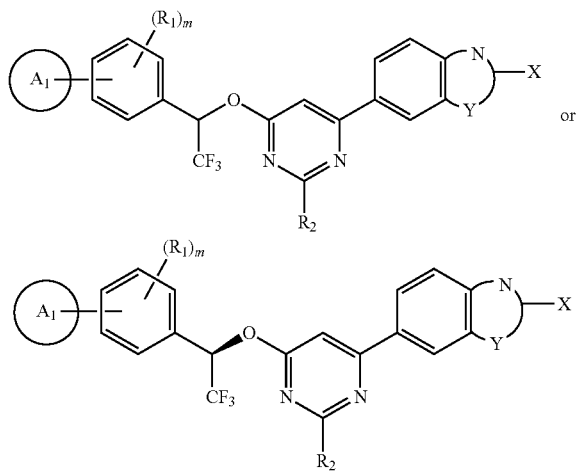

(aa)

(bb)

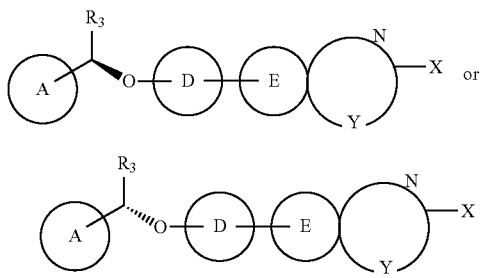

where $A_1$ is optionally substituted heterocycle; X is $CO_2R$ or $SO_3R$, Y is O, R is hydrogen or methyl, N and Y form part of a 7-membered ring where N is linked to the carbon bearing X and Y is separated from the carbon bearing X by a methylene, each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4. In some of these compounds, R is hydrogen. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

where A is optionally substituted cycloalkyl, aryl, or heterocycle; D is optionally substituted aryl or heterocycle; E is optionally substituted aryl or heterocycle; X is $CO_2R$ or $SO_3R$; Y is O; R is hydrogen or lower alkyl; N and Y form part of a 7-membered ring where N is linked to the carbon bearing X and Y is separated from the carbon bearing X by a methylene; $R_3$ is trifluoromethyl; and X is —$CH_2$—, N, S, O, or is absent. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydrogen.

In some compounds, R is methyl, ethyl, or isopropyl. In some of these compounds, R is methyl.

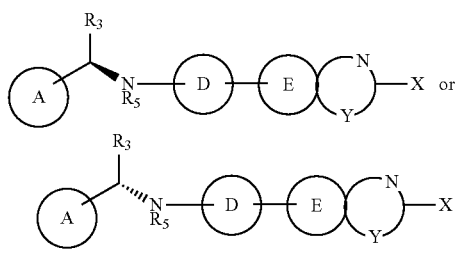

where A is optionally substituted cycloalkyl, aryl, or heterocycle; D is optionally substituted aryl or heterocycle; E is optionally substituted aryl or heterocycle; X is $CO_2R$ or $SO_3R$; Y is O; R is hydrogen or lower alkyl; N and Y form part of a 7-membered ring where N is linked to the carbon bearing X and Y is separated from the carbon bearing X by a methylene; $R_3$ is hydrogen; and $R_5$ is hydrogen or optionally substituted alkyl or aryl. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, R is hydrogen.

In some compounds, R is methyl, ethyl, or isopropyl. In some of these compounds, R is methyl.

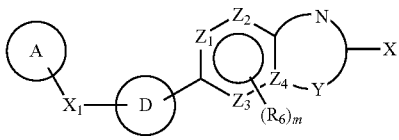

where A is optionally substituted cycloalkyl, aryl, or heterocycle; $X_1$ is a bond (i.e., A is directly bound to D), —O—, —S—, —C(O)—, —$C(R_4)$=, =$C(R_4)$—, —$C(R_3R_4)$—, —$C(R_4)$=$C(R_4)$—, —C≡C—, —$N(R_5)$—, —$N(R_5)C(O)N(R_5)$—, —$C(R_3R_4)N(R_5)$—, —$N(R_5)C(R_3R_4)$—, —ONC($R_3$)—, —$C(R_3)NO$—, —$C(R_3R_4)O$—, —$OC(R_3R_4)$—, —$S(O_2)$—, —$S(O_2)N(R_5)$—, —$N(R_5)S(O_2)$—, —$C(R_3R_4)S(O_2)$—, or —$S(O_2)C(R_3R_4)$—; D is optionally substituted aryl or heterocycle; each of $Z_1$, $Z_2$, $Z_3$, and $Z_4$ is independently N or $CR_6$; X is $CO_2R$, $SO_3R$, $BOROR_1$, or $COCO_2R$; Y is —$CH_2$—, N, S, or O; R is hydrogen or lower alkyl; $R_1$ is hydrogen or lower alkyl; N and Y form part of a 6, 7, or 8-membered heterocycle fused to D; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; and m is 1-4. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In some compounds, X is $CO_2R$ or $SO_3R$, Y is O, and R is hydrogen.

In some compounds, X is $CO_2R$ or $SO_3R$, Y is O, and R is methyl, ethyl, or isopropyl. In some of these compounds, R is methyl.

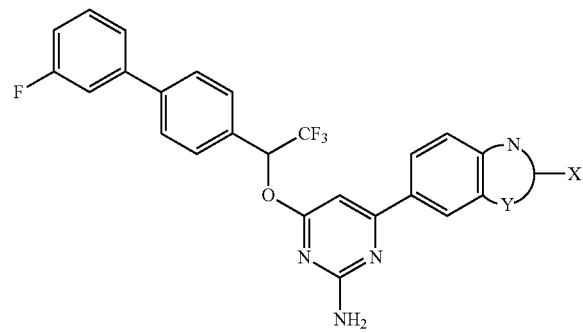

(ee)

where X is $CO_2R$, $SO_3R$, $BOROR_1$, or $COCO_2R$; Y is —$CH_2$—, N, S, or O; R is hydrogen or lower alkyl; $R_1$ is hydrogen or lower alkyl; and N and Y form part of a 6, 7, or 8-membered heterocycle fused as shown to the indicated phenyl. In some of these compounds, X is $CO_2R$ or $SO_3R$, Y is O, and R is hydrogen or lower alkyl. In some of these compounds, R is hydrogen. Where a carbon attached to X is an asymmetric carbon, it may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

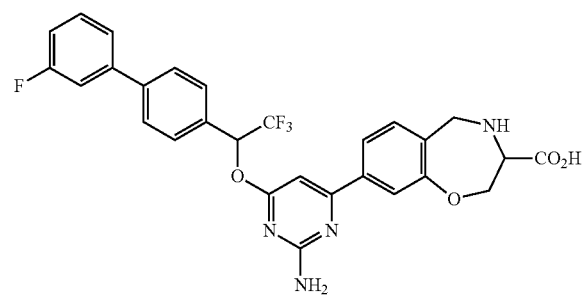

(ff)

The carbon attached to $CO_2H$ is an asymmetric carbon and may be present as the R or S enantiomer, or in a mixture of the R and S enantiomers, including a mixture that is approximately 50% R and 50% S. In particular embodiments, the asymmetric carbon is present in essentially pure (i.e., about 100%) R or in essentially pure (i.e., about 100%) S form.

In certain embodiments, the compound of the present invention is a TPH1 inhibitor that is a β-amino carboxylic acid or a β-amino carboxylic acid ester selected from the following or from pharmaceutically acceptable salts or solvates thereof

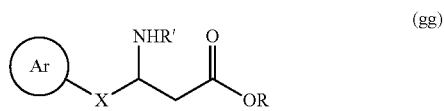

(gg)

where Ar is a structure comprising 1-4 optionally substituted linked cycloalkyl, aryl, or heterocycle rings; X is —$CH_2$—, N, S, O, or is absent; R is hydrogen or lower alkyl; and R' is hydrogen or lower alkyl. In some compounds, Ar comprises 1 ring; in some compounds, Ar comprises 2 rings; in some compounds, Ar comprises 3 rings; in some compounds, Ar comprises 4 rings. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

In some compounds, X is —$CH_2$— or is absent. In some compounds, X is absent.

In some compounds, R is methyl, ethyl, or isopropyl.

In some compounds, X is absent, R is hydrogen or methyl, and R' is hydrogen. In some of these compounds, R is hydrogen.

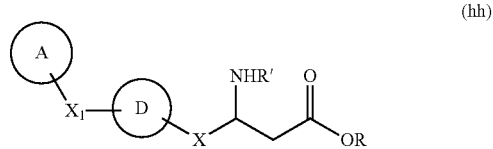

(hh)

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; R is hydrogen or lower alkyl; R' is hydrogen or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and X is —$CH_2$—, N, S, O, or is absent. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

In some compounds, X is —CH₂— or is absent. In some compounds, X is absent.

In some compounds, R is methyl, ethyl, or isopropyl.

In some compounds, X is absent, R is hydrogen or methyl, and R' is hydrogen. In some of these compounds, R is hydrogen.

In some compounds, X is absent, R is hydrogen or methyl, R' is hydrogen, $X_1$ is —C($R_3R_4$)O—, $R_3$ is hydrogen, and $R_4$ is substituted alkyl, preferably trifluoromethyl. In some of these compounds, R is hydrogen.

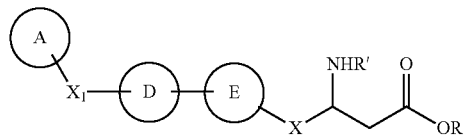

(ii)

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; R is hydrogen or lower alkyl; R' is hydrogen or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and X is —CH₂—, N, S, O, or is absent. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

In some compounds, X is —CH₂— or is absent. In some compounds, X is absent.

In some compounds, R is methyl, ethyl, or isopropyl. In some compounds, R is methyl.

In some compounds, X is absent, R is methyl, and R' is hydrogen.

In some compounds, A is fluoro-substituted biphenyl, X is —CH₂— or is absent, R is hydrogen or methyl, R' is hydrogen, $X_1$ is —C($R_3R_4$)O—, $R_3$ is hydrogen, and $R_4$ is substituted alkyl. In some of these compounds, A is 3'-fluorobiphenyl, X is absent, and R is hydrogen. In some of these compounds, $R_4$ is halo-substituted methyl. In some of these compounds, D is substituted pyrimidinyl and E is phenyl. In some of these compounds, D is 2-substituted pyrimidinyl. In some of these compounds, D is 2-amino pyrimidinyl.

In some compounds, A is optionally substituted biphenyl, X is —C($R_3R_4$)O—, $R_3$ is hydrogen, $R_4$ is optionally substituted lower alkyl, D is optionally substituted pyrimidinyl, E is phenyl, X is —CH₂— or is absent, R is hydrogen or methyl, and R' is hydrogen. In some of these compounds, X is absent. In some of these compounds, A is 2'-, 3'-, 4'-, 5', or 6'-halo-substituted biphenyl, $R_4$ is halo-substituted methyl or ethyl, and D is 2-substituted pyrimidinyl. In some of these compounds, A is 2'-, 3'-, 4'-, 5', or 6'-fluoro-substituted biphenyl, $R_4$ is fluoro-substituted methyl, and D is 2-amino substituted pyrimidinyl.

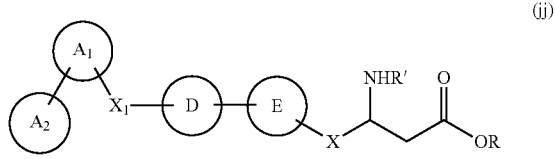

(jj)

where each of $A_1$ and $A_2$ is independently a monocyclic optionally substituted cycloalkyl, aryl, or heterocycle; $X_1$ is a bond (i.e., $A_1$ is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; R is H or lower alkyl; R' is H or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and X is —CH₂—, N, S, O, or is absent. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

Compounds encompassed by the formula immediately above include those wherein $A_1$ and/or $A_2$ is optionally substituted cycloalkyl (e.g., 6-membered and 5-membered). In some, $A_1$ and/or $A_2$ is optionally substituted aryl (e.g., phenyl or naphthyl). In others, $A_1$ and/or $A_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

Particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

Particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

In some compounds, X is —CH$_2$— or is absent. In some compounds, X is absent.

In some compounds, R is methyl, ethyl, or isopropyl. In some compounds, R is methyl.

In some compounds, X is absent, R is methyl, and R' is hydrogen.

In some compounds, $X_1$ is a bond or S. In others, $X_1$ is —C(R$_4$)=, =C(R$_4$)—, —C(R$_3$R$_4$)—, —C(R$_4$)=C(R$_4$)—, or —C≡C—, and, for example, R$_4$ is independently hydrogen or optionally substituted alkyl. In some of these compounds, X is absent, R is methyl, and R' is hydrogen.

In some compounds, $X_1$ is —O—, —C(R$_3$R$_4$)O—, or —OC(R$_3$R$_4$)—, and, for example, R$_3$ is hydrogen or optionally substituted alkyl, and R$_4$ is hydrogen or optionally substituted alkyl. In some of these compounds, R$_3$ is hydrogen and R$_4$ is trifluoromethyl. In some of these compounds, X is absent, R is methyl, and R' is hydrogen.

In some compounds, $X_1$ is —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—, and, for example, R$_3$ is hydrogen or optionally substituted alkyl, R$_4$ is hydrogen or optionally substituted alkyl, and R$_5$ is hydrogen or optionally substituted alkyl. In some of these compounds, X is absent, R is methyl, and R' is hydrogen.

In some compounds, $X_1$ is —N(R$_5$)—, —N(R$_5$)C(O)N(R$_5$)—, —C(R$_3$R$_4$)N(R$_5$)—, or —N(R$_5$)C(R$_3$R$_4$)—, and, for example, R$_3$ is hydrogen or optionally substituted alkyl, R$_4$ is hydrogen or optionally substituted alkyl, and each R$_5$ is independently hydrogen or optionally substituted alkyl. In some of these compounds, X is absent, R is methyl, and R' is hydrogen.

(kk)

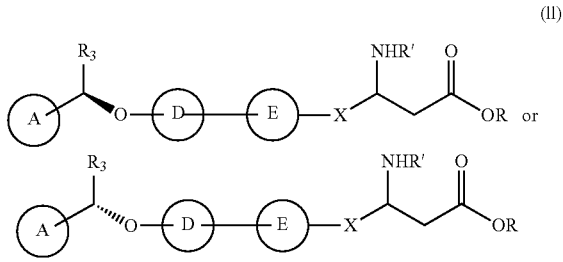

or

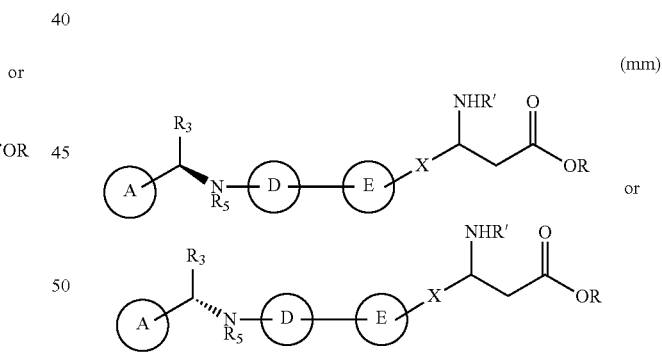

where A$_1$ is optionally substituted heterocycle; R is hydrogen or lower alkyl; R' is hydrogen or lower alkyl; each R$_1$ is independently halogen, hydrogen, C(O)R$_A$, OR$_A$, NR$_B$R$_C$, S(O$_2$)R$_A$, or optionally substituted alkyl, alkyl-aryl or alkyl-heterocycle; R$_2$ is halogen, hydrogen, C(O)R$_A$, OR$_A$, NR$_B$R$_C$, S(O$_2$)R$_A$, or optionally substituted alkyl, alkyl-aryl or alkyl-heterocycle; each R$_A$ is independently hydrogen or optionally substituted alkyl, alkyl-aryl or alkyl-heterocycle; each R$_B$ is independently hydrogen or optionally substituted alkyl, alkyl-aryl or alkyl-heterocycle; each R$_R$ is independently hydrogen or optionally substituted alkyl, alkyl-aryl or alkyl-heterocycle; X is —CH$_2$—, N, S, O, or is absent; and m is 1-4. The carbon attached to the NHR' group may be present as the R or S enantiomer, or in a mixture of the R and S enantiomers, including a mixture that is approximately 50% R and 50% S.

In particular compounds, the carbon attached to the NHR' group is present in essentially pure (i.e., about 100%) R or in essentially pure (i.e., about 100%) S form.

In some compounds, X is —CH$_2$— or is absent. In some compounds, X is absent.

In some compounds, R is methyl, ethyl, or isopropyl. In some compounds, R is methyl.

In some compounds, X is absent, R is methyl, and R' is hydrogen.

(ll)

where A is optionally substituted cycloalkyl, aryl, or heterocycle; D is optionally substituted aryl or heterocycle; E is optionally substituted aryl or heterocycle; R is hydrogen or lower alkyl; R' is hydrogen or lower alkyl; R$_3$ is trifluoromethyl; and X is —CH$_2$—, N, S, O, or is absent. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

In some compounds, X is —CH$_2$— or is absent. In some compounds, X is absent.

In some compounds, R is methyl, ethyl, or isopropyl.

In some compounds, X is absent, R is hydrogen or methyl, and R' is hydrogen. In some of these compounds, R is hydrogen.

(mm)

where A is optionally substituted cycloalkyl, aryl, or heterocycle; D is optionally substituted aryl or heterocycle; E is optionally substituted aryl or heterocycle; R is hydrogen or lower alkyl; R' is hydrogen or lower alkyl; X is —CH$_2$—, N, S, O, or is absent; R$_3$ is hydrogen; and R$_5$ is hydrogen or optionally substituted alkyl or aryl. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

In some compounds, X is —CH$_2$— or is absent. In some compounds, X is absent.

In some compounds, R is methyl, ethyl, or isopropyl.

In some compounds, X is absent, R is hydrogen or methyl, and R' is hydrogen. In some of these compounds, R is hydrogen.

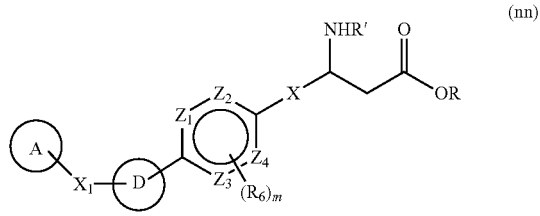

(nn)

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; each of $Z_1$, $Z_2$, $Z_3$, and $Z_4$ is independently N or $CR_6$; R is hydrogen or lower alkyl; R' is hydrogen or lower alkyl; X is —$CH_2$—, N, S, O, or is absent; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; and m is 1-4. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

In some compounds, X is —$CH_2$— or is absent. In some compounds, X is absent.

In some compounds, R is methyl, ethyl, or isopropyl.

In some compounds, X is absent, R is hydrogen or methyl, and R' is hydrogen. In some of these compounds, R is hydrogen.

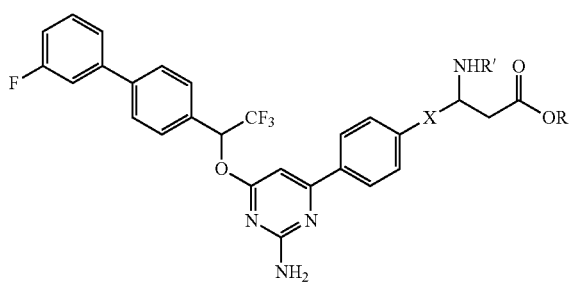

(oo)

where X is —$CH_2$—, N, S, O, or is absent; R is hydrogen or lower alkyl; and R' is hydrogen or lower alkyl. In some of these compounds, X is absent, R is lower alkyl; and R' is hydrogen. In some of these compounds, R is methyl, ethyl, or isopropyl. In some of these compounds, R is methyl. The carbon attached to the NHR' group may be present as the R or S enantiomer, or in a mixture of the R and S enantiomers, including a mixture that is approximately 50% R and 50% S. In particular compounds, the carbon attached to the NHR' group is present in essentially pure (i.e., about 100%) R or in essentially pure (i.e., about 100%) S form.

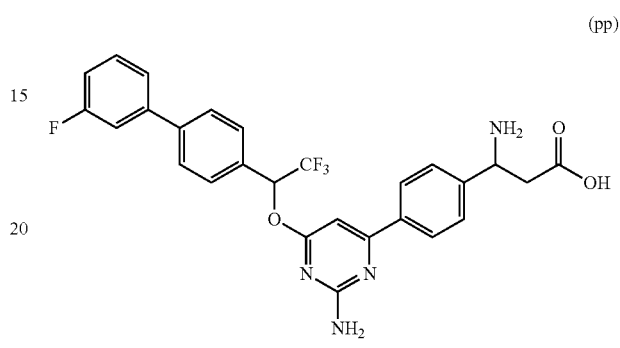

(pp)

The carbon to which the β-amino group is attached may be present as the R or S enantiomer, or in a mixture of the R and S enantiomers, including a mixture that is approximately 50% R and 50% S. In particular compounds, the carbon to which the β-amino group is attached is present in essentially pure (i.e., about 100%) R or in essentially pure (i.e., about 100%) S form.

In certain embodiments, the compound of the present invention is a TPH1 inhibitor that is a boronic acid or a boronic acid ester selected from the following or from pharmaceutically acceptable salts or solvates thereof

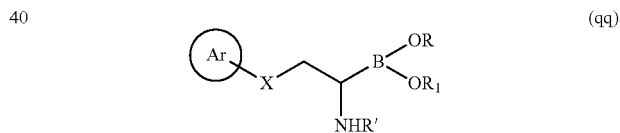

(qq)

where Ar is a structure comprising 1-4 optionally substituted linked cycloalkyl, aryl, or heterocycle rings; X is —$CH_2$—, N, S, O, or is absent; R is hydrogen or lower alkyl; R' is hydrogen or lower alkyl; $R_1$ is hydrogen or lower alkyl. In some compounds, Ar comprises 1 ring; in some compounds, Ar comprises 2 rings; in some compounds, Ar comprises 3 rings; in some compounds, Ar comprises 4 rings. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

In some compounds, X is O or N. In some compounds, X is O.

In some compounds, R is methyl, ethyl, or isopropyl, and $R_1$ is hydrogen.

In some compounds, X is O, R is hydrogen or methyl, $R_1$ is hydrogen, and R' is hydrogen. In some of these compounds, R is hydrogen.

(rr)

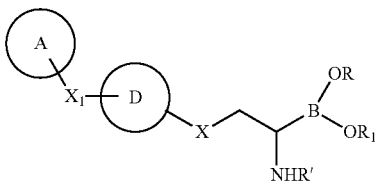

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; R is hydrogen or lower alkyl; R' is hydrogen or lower alkyl; $R_1$ is hydrogen or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and X is —$CH_2$—, N, S, O, or is absent. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

In some compounds, X is O or N. In some compounds, X is O.

In some compounds, R is methyl, ethyl, or isopropyl, and $R_1$ is hydrogen.

In some compounds, X is O, R is hydrogen or methyl, $R_1$ is hydrogen, and R' is hydrogen. In some of these compounds, R is hydrogen.

In some compounds, X is O, R is hydrogen or methyl, R' is hydrogen, $X_1$ is —C($R_3R_4$)O—, $R_3$ is hydrogen, and $R_4$ is substituted alkyl, preferably trifluoromethyl. In some of these compounds, R is hydrogen.

(ss)

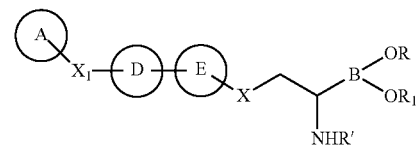

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; R is hydrogen or lower alkyl; R' is hydrogen or lower alkyl; $R_1$ is hydrogen or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and X is —$CH_2$—, N, S, O, or is absent. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

In some compounds, X is O or N. In some compounds, X is O.

In some compounds, R is methyl, ethyl, or isopropyl. In some compounds, R is methyl.

In some compounds, X is O, R is hydrogen or methyl, R' is hydrogen, and $R_1$ is hydrogen. In some of these compounds, R is hydrogen.

In some compounds, A is fluoro-substituted biphenyl, X is O or N, R is hydrogen or methyl, R' is hydrogen, $R_1$ is hydrogen, $X_1$ is —C($R_3R_4$)O—, $R_3$ is hydrogen, and $R_4$ is substituted alkyl. In some of these compounds, A is 3'-fluorobiphenyl, X is O, and R is hydrogen. In some of these compounds, $R_4$ is halo-substituted methyl. In some of these compounds, D is substituted pyrimidinyl and E is phenyl. In some of these compounds, D is 2-substituted pyrimidinyl. In some of these compounds, D is 2-amino pyrimidinyl.

In some compounds, A is optionally substituted biphenyl, X is —C($R_3R_4$)O—, $R_3$ is hydrogen, $R_4$ is optionally substituted lower alkyl, D is optionally substituted pyrimidinyl, E is phenyl, X is O or N, R is hydrogen or methyl, R' is hydrogen, and $R_1$ is hydrogen. In some of these compounds, X is O. In some of these compounds, A is 2'-, 3'-, 4'-, 5', or 6'-halo-substituted biphenyl, $R_4$ is halo-substituted methyl or ethyl, and D is 2-substituted pyrimidinyl. In some of these compounds, A is 2'-, 3'-, 4'-, 5', or 6'-fluoro-substituted biphenyl, $R_4$ is trifluoro-substituted methyl, and D is 2-amino substituted pyrimidinyl.

(tt)

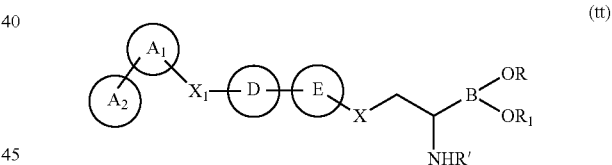

where each of $A_1$ and $A_2$ is independently a monocyclic optionally substituted cycloalkyl, aryl, or heterocycle; $X_1$ is a bond (i.e., $A_1$ is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; R is H or lower alkyl; $R_1$ is H or lower alkyl; R' is H or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and X is —$CH_2$—, N, S, O, or is absent. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

Compounds encompassed by the formula immediately above include those wherein $A_1$ and/or $A_2$ is optionally substituted cycloalkyl (e.g., 6-membered and 5-membered). In some, $A_1$ and/or $A_2$ is optionally substituted aryl (e.g., phenyl or naphthyl). In others, $A_1$ and/or $A_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

Particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

Particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

In some compounds, X is O or N. In some of these compounds, X is O.

In some compounds, R is methyl, ethyl, or isopropyl. In some of these compounds, R is methyl.

In some compounds, X is O, R is hydrogen or methyl, R' is hydrogen, and $R_1$ is hydrogen. In some of these compounds, R is hydrogen.

In some compounds, $X_1$ is a bond or S. In others, $X_1$ is —C($R_4$)=, =C($R_4$)—, —C($R_3R_4$)—, —C($R_4$)=C($R_4$)—, or —C≡C—, and, for example, $R_4$ is independently hydrogen or optionally substituted alkyl. In some of these compounds, X is O, R is hydrogen or methyl, R' is hydrogen, and $R_1$ is hydrogen. In some of these compounds, R is hydrogen.

In some compounds, $X_1$ is —O—, —C($R_3R_4$)O—, or —OC($R_3R_4$)—, and, for example, $R_3$ is hydrogen or optionally substituted alkyl, and $R_4$ is hydrogen or optionally substituted alkyl. In some of these compounds, $R_3$ is hydrogen and $R_4$ is trifluoromethyl. In some of these compounds, X is O, R is hydrogen or methyl, R' is hydrogen, and $R_1$ is hydrogen. In some of these compounds, R is hydrogen.

In some compounds, $X_1$ is —S($O_2$)—, —S($O_2$)N($R_5$)—, —N($R_5$)S($O_2$)—, —C($R_3R_4$)S($O_2$)—, or —S($O_2$)C($R_3R_4$)—, and, for example, $R_3$ is hydrogen or optionally substituted alkyl, $R_4$ is hydrogen or optionally substituted alkyl, and $R_5$ is hydrogen or optionally substituted alkyl. In some of these compounds, X is O, R is hydrogen or methyl, R' is hydrogen, and $R_1$ is hydrogen. In some of these compounds, R is hydrogen.

In some compounds, $X_1$ is —N($R_5$)—, —N($R_5$)C(O)N($R_5$)—, —C($R_3R_4$)N($R_5$)—, or —N($R_5$)C($R_3R_4$)—, and, for example, $R_3$ is hydrogen or optionally substituted alkyl, $R_4$ is hydrogen or optionally substituted alkyl, and each $R_5$ is independently hydrogen or optionally substituted alkyl. In some of these compounds, X is O, R is hydrogen or methyl, R' is hydrogen, and $R_1$ is hydrogen. In some of these compounds, R is hydrogen.

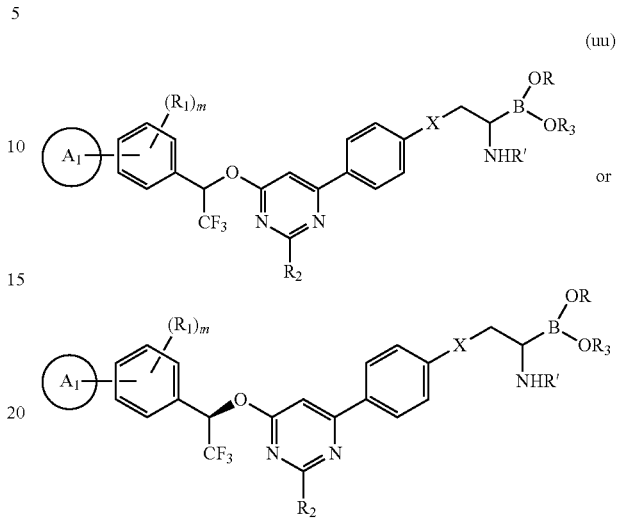

(uu)

where $A_1$ is optionally substituted heterocycle; R is hydrogen or lower alkyl; R' is hydrogen or lower alkyl; each $R_1$ is independently halogen, hydrogen, C(O)$R_A$, O$R_A$, N$R_BR_C$, S($O_2$)$R_A$, or optionally substituted alkyl, alkyl-aryl or alkyl-heterocycle; $R_2$ is halogen, hydrogen, C(O)$R_A$, O$R_A$, N$R_BR_C$, S($O_2$)$R_A$, or optionally substituted alkyl, alkyl-aryl or alkyl-heterocycle; $R_3$ is hydrogen or lower alkyl; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; X is —$CH_2$—N, S, O, or is absent; and m is 1-4. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

In some compounds, X is O or N. In some compounds, X is O.

In some compounds, R is methyl, ethyl, or isopropyl. In some compounds, R is methyl.

In some compounds, X is O, R is hydrogen or methyl, R' is hydrogen, and $R_3$ is hydrogen. In some of these compounds, R is hydrogen.

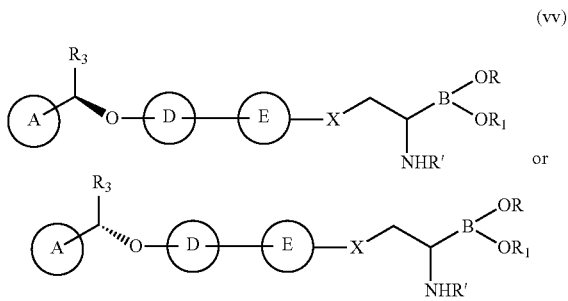

(vv)

wherein A is optionally substituted cycloalkyl, aryl, or heterocycle; D is optionally substituted aryl or heterocycle; E is optionally substituted aryl or heterocycle; R is hydrogen or lower alkyl; R' is hydrogen or lower alkyl; $R_1$ is hydrogen or lower alkyl; $R_3$ is trifluoromethyl; and X is —$CH_2$—N, S, O, or is absent. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

In some compounds, X is O or N. In some compounds, X is O.

In some compounds, R is methyl, ethyl, or isopropyl, and $R_1$ is hydrogen.

In some compounds, X is O, R is hydrogen or methyl, $R_1$ is hydrogen, and R' is hydrogen. In some of these compounds, R is hydrogen.

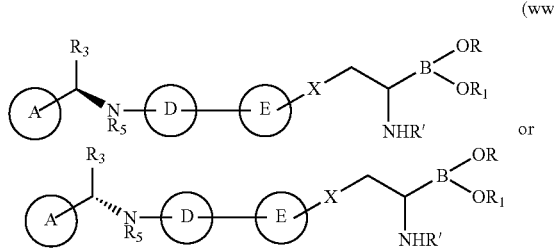

(ww)

or where A is optionally substituted cycloalkyl, aryl, or heterocycle; D is optionally substituted aryl or heterocycle; E is optionally substituted aryl or heterocycle; R is hydrogen or lower alkyl; R' is hydrogen or lower alkyl; $R_1$ is hydrogen or lower alkyl; X is —$CH_2$—N, S, O, or is absent; $R_3$ is hydrogen; and $R_5$ is hydrogen or optionally substituted alkyl or aryl. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

In some compounds, X is O or N. In some these compounds, X is O.

In some compounds, R is methyl, ethyl, or isopropyl, and $R_1$ is hydrogen.

In some compounds, X is O, R is hydrogen or methyl, $R_1$ is hydrogen, and R' is hydrogen. In some of these compounds, R is hydrogen.

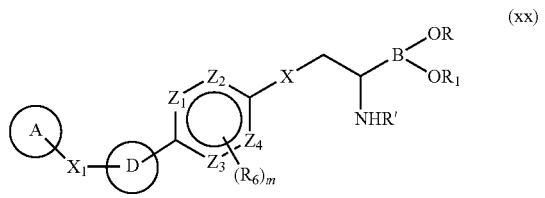

(xx)

where A is optionally substituted cycloalkyl, aryl, or heterocycle; $X_1$ is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; each of $Z_1$, $Z_2$, $Z_3$, and $Z_4$ is independently N or C$R_6$; R is hydrogen or lower alkyl; R' is hydrogen or lower alkyl; $R_1$ is hydrogen or lower alkyl; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; X is —$CH_2$—N, S, O, or is absent; and m is 1-4.

In some compounds, X is O or N. In some of these compounds, X is O.

In some compounds, R is methyl, ethyl, or isopropyl, and $R_1$ is hydrogen.

In some compounds, X is O, R is hydrogen or methyl, $R_1$ is hydrogen, and R' is hydrogen. In some of these compounds, R is hydrogen.

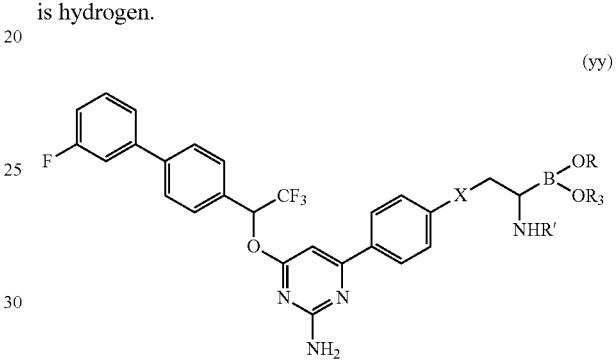

(yy)

where X is —$CH_2$—, N, S, O, or is absent; R is hydrogen or lower alkyl; R' is hydrogen or lower alkyl; and $R_3$ is hydrogen or lower alkyl. In some of these compounds, X is O or N, R is hydrogen, R' is hydrogen, and $R_3$ is lower alkyl. In some of these compounds, $R_3$ is methyl, ethyl, or isopropyl. In some of these compounds, $R_3$ is methyl. The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

In one of these compounds, X is O, R is hydrogen, R' is hydrogen, and $R_3$ is methyl.

In one of these compounds, X is O, R is hydrogen, R' is hydrogen, and $R_3$ is ethyl.

In one of these compounds, X is O, R is hydrogen, R' is hydrogen, and $R_3$ is isopropyl.

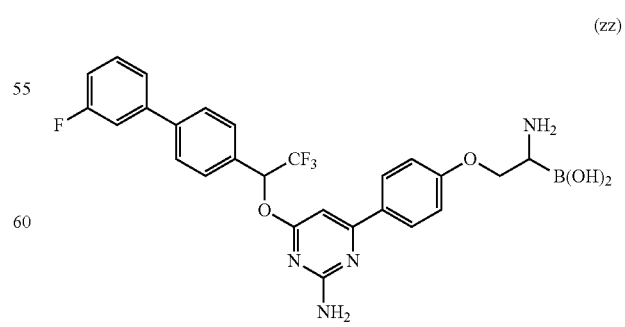

(zz)

The carbon attached to the boron may be present as the R or S enantiomer, or in a mixture of the R and S enantiomers, including a mixture that is approximately 50% R and 50% S. In particular compounds, the carbon attached to the boron is present in essentially pure (i.e., about 100%) R or in essentially pure (i.e., about 100%) S form.

The present invention provides pharmaceutical compositions comprising a therapeutically effective amount of a TPH1 inhibitor disclosed herein and at least one pharmaceutically acceptable excipient. In certain embodiments, the TPH1 inhibitor may be in the form of a salt with a physiologically acceptable acid or base.

The present invention also provides methods where a patient is administered both a TPH1 inhibitor and a serotonin receptor antagonist. The TPH1 inhibitor and the serotonin receptor antagonist may be administered together in a single pharmaceutical composition or in separate pharmaceutical compositions.

In certain embodiments, the serotonin receptor antagonist is an HT1B, HT2A, or HT2B serotonin receptor antagonist, and, most preferably, an HT1B serotonin receptor antagonist. In certain embodiments, the serotonin receptor antagonist is an HT1B serotonin receptor antagonist listed in Table 2.

In certain embodiments, the low bone mass disease is osteoporosis, osteoporosis pseudoglioma syndrome (OPPG), osteopenia, osteomalacia, renal osteodystrophy, faulty bone formation or resorption, Paget's disease, fractures and broken bones, or bone metastasis. Preferably, the low bone mass disease is osteoporosis.

In other embodiments, the patient is being treated with an SSRI, a bisphosphonate, or a beta blocker in addition to a compound disclosed herein that lowers the level of serum serotonin. In some embodiments, the methods of the present invention also comprise administering an SSRI, a bisphosphonate, or a beta blocker in addition to a compound disclosed herein that lowers the level of serum serotonin.

In certain embodiments, the patient is being treated with an agent that increases the level of serum serotonin (e.g., an SSRI) where the agent is administered for a purpose unrelated to treatment of a bone mass disease (e.g., to treat depression). In some embodiments, the patient has a condition associated with an increased level of serum serotonin.

In certain embodiments, the patient's level of serum serotonin is measured prior to administering a compound disclosed herein that lowers the level of serum serotonin. In other embodiments, the patient's level of serum serotonin is measured after administering a compound disclosed herein that lowers the level of serum serotonin. In some embodiments, the patient's level of serum serotonin is measured before and after administering a compound disclosed herein that lowers the level of serum serotonin.

In certain embodiments, a compound disclosed herein that lowers the level of serum serotonin is repeatedly administered to the patient and the patient's level of serum serotonin is repeatedly measured until the patient's level of serum serotonin is reduced to a desired level, e.g., by at least about 10% compared to the level measured prior to the first administration of the compound disclosed herein that lowers the level of serum serotonin.

In certain embodiments, the patient has been identified as having a serum serotonin level that is more than 10%, 25%, 35%, 50%, 75%, 100%, or 200% higher than the normal level of serum serotonin.

In certain embodiments, the patient is administered an agent that increases brain derived serotonin in addition to a compound disclosed herein that lowers the level of serum serotonin. In preferred embodiments, the agent that increases brain derived serotonin is an agent that increases TPH2 activity.

In certain embodiments, the patient's level of serum serotonin is lowered by at least about 10%, at least about 20%, at least about 30%, at least about 40%, at least about 50%, at least about 60%, at least about 70%, at least about 80%, or at least about 90% compared to the level before administering the compound disclosed herein that lowers the level of serum serotonin.

In certain embodiments, the compound disclosed herein that lowers the level of serum serotonin is administered in an amount of from about 1 mg/day to about 2 g/day.

The present invention provides a pharmaceutical composition comprising an amount of a compound disclosed herein that lowers the level of serum serotonin in a patient to whom the composition is administered by at least about 10%, at least about 20%, at least about 30%, at least about 40%, at least about 50%, at least about 60%, at least about 70%, at least about 80%, or at least about 90%.

In some embodiments, the pharmaceutical composition comprises a compound disclosed herein that lowers the level of serum serotonin and an agent that raises the level of brain-derived serotonin.

In some embodiments, the pharmaceutical composition comprises a compound disclosed herein that lowers the level of serum serotonin and an SSRI, a bisphosphonate, or a beta blocker. In certain embodiments, the pharmaceutical composition also comprises a serotonin receptor antagonist that is an HT1B, HT2A or HT2B serotonin receptor antagonist, preferably an HT1B serotonin receptor antagonist.

In certain embodiments, the pharmaceutical composition comprises both a compound disclosed herein and a serotonin receptor antagonist.

The present invention also provides a method for identifying a patient at risk of developing a disease associated with low bone mass and treating that patient, comprising:

a) determining the level of serum serotonin in a biological sample taken from the patient and in a biological sample taken from the from a normal subject;

b) concluding that the patient is at risk of developing the disease if the level of serum serotonin in the sample from the patient is elevated by at least about 25% above the serum serotonin level in the sample from the normal subject; and c) administering to the patient a therapeutically effective amount of a compound disclosed herein;

whereby the patient's serum serotonin level is lowered.

DETAILED DESCRIPTION OF THE INVENTION

Figure 1:
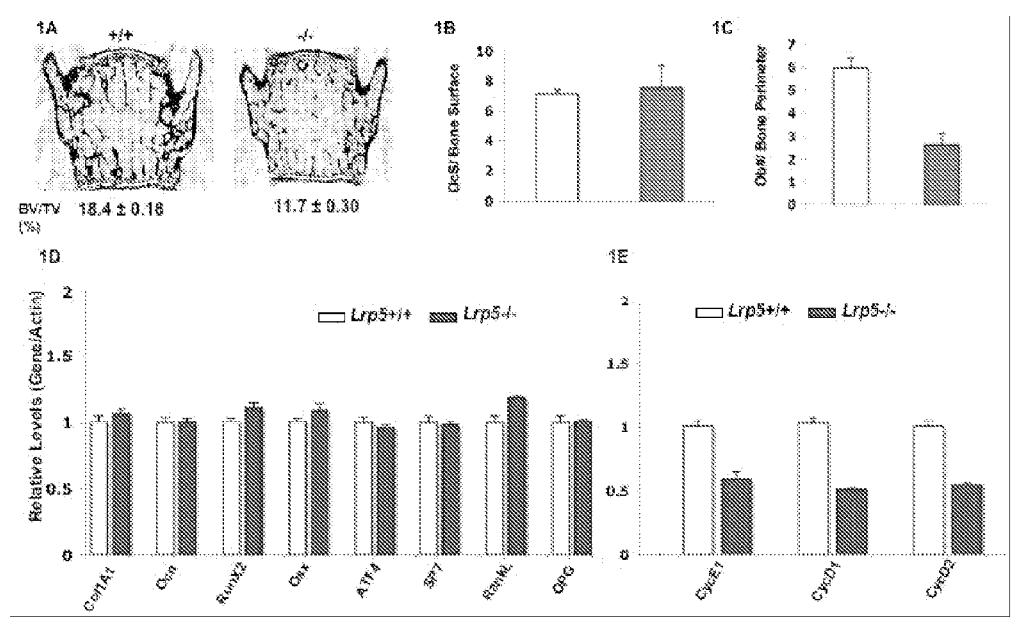
FIG. 1. Lrp5−/− mice have low bone mass (A) with no change in osteoclast surface (B) but decreased osteoblast numbers (C). Real-time PCR analysis of Lrp5−/− molecular signature. Lrp5−/− osteoblasts do not show changes in osteoblast-specific gene expression (D) but have decreased Cyclin genes expression (E).

The term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NH-CONH-alkyl-).

The term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

The term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as the corresponding alkenyl and alkynyl moieties.

The term "alkoxy" means an —O-alkyl group. Examples of alkoxy groups include —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Term "alkylaryl" or "alkyl-aryl" means an alkyl moiety bound to an aryl moiety.

The term "alkylheteroaryl" or "alkyl-heteroaryl" means an alkyl moiety bound to a heteroaryl moiety.

The term "alkylheterocycle" or "alkyl-heterocycle" means an alkyl moiety bound to a heterocycle moiety.

The term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

The term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

The term "arylalkyl" or "aryl-alkyl" means an aryl moiety bound to an alkyl moiety.

The terms "halogen" and "halo" encompass fluorine, chlorine, bromine, and iodine.

The term "heteroalkyl" refers to an alkyl moiety (e.g., linear, branched or cyclic) in which at least one of its carbon atoms has been replaced with a heteroatom (e.g., N, O or S).

The term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

The term "heteroarylalkyl" or "heteroaryl-alkyl" means a heteroaryl moiety bound to an alkyl moiety.

The term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

The term "heterocyclealkyl" or "heterocycle-alkyl" refers to a heterocycle moiety bound to an alkyl moiety.

The term "heterocycloalkyl" refers to a non-aromatic heterocycle.

The term "heterocycloalkylalkyl" or "heterocycloalkyl-alkyl" refers to a heterocycloalkyl moiety bound to an alkyl moiety.

The term "disease or disorder mediated by peripheral serotonin" refers to a disease or disorder having one or more symptoms the severity of which are affected by peripheral serotonin levels.

Diseases associated with low bone density ("low bone mass diseases"), as used herein, refers to any bone disease or state that results in or is characterized by loss of health or integrity to bone due to abnormally low bone mass, and includes, but is not limited to, osteoporosis, osteoporosis pseudoglioma syndrome (OPPG), osteopenia, osteomalacia, renal osteodystrophy, faulty bone formation or resorption, Paget's disease, fractures and broken bones, and bone metastasis. More particularly, bone diseases that can be treated and/or prevented in accordance with the present invention include bone diseases characterized by a decreased bone mass relative to that of corresponding non-diseased bone.

Prevention of bone disease means actively intervening as described herein prior to overt disease onset to prevent the disease or minimize the extent of the disease or slow its course of development.

Treatment of bone disease means actively intervening after onset to slow down, ameliorate symptoms of, minimize the extent of, or reverse the disease or situation in a patient who is known or suspected of having a bone disease, particularly a low bone mass disease. More specifically, treating refers to a method that modulates bone mass to more closely resemble that of corresponding non-diseased bone (that is a corresponding bone of the same type, e.g., long, vertebral, etc.) in a non-diseased state.

Unless otherwise indicated, a "therapeutically effective amount" of a compound is an amount that provides a therapeutic benefit in the treatment or management of a disease or condition, delays or minimizes one or more symptoms associated with the disease or condition, or enhances the therapeutic efficacy of another therapeutic agent. An agent is said to be administered in a "therapeutically effective amount" if the amount administered results in a desired change in the physiology of a recipient mammal (e.g., increases bone mass in a mammal having or at risk of developing a low bone mass disease) compared to pre-treatment levels. That is, drug therapy results in treatment, i.e., modulates bone mass to more closely resemble that of corresponding non-diseased bone (such as a corresponding bone of the same type, e.g., long, vertebral, etc.) in a non-diseased state. For example, a therapeutically effective amount of a compound disclosed herein that is a TPH1 inhibitor includes, but is not limited to, an amount that reduces serum serotonin levels to a level that is at least about 10% less than the level before drug treatment and provides a therapeutic benefit.

A therapeutic agent such as a TPH1 inhibitor significantly reduces serum serotonin if the post-treatment level of serotonin is reduced at least about 10% or more compared to pre-treatment levels. A patient is at risk of developing a low bone mass disease if his or her serum serotonin levels are elevated by about 25% or more compared to serum serotonin levels in normal subjects.

A "patient" is a mammal, preferably a human, but can also be a companion animal such as dogs or cats, or a farm animal such as horses, cattle, pigs, or sheep.

A patient in need of treatment or prevention for a bone disease includes a patient known or suspected of having or being at risk of developing a bone disease. Such a patient in need of treatment could be, e.g., a person known to have osteoporosis. A patient at risk of developing a bone disease could include the elderly, post-menopausal women, patients being treated with glucocorticoids, patients being treated with SSRIs, and patients having bone density outside the normal range. Other persons in need of treatment or prevention by the methods of the present invention include persons who are known to be in need of therapy to decrease serum serotonin levels in order to treat or prevent a bone disease, e.g., osteoporosis. Such persons might include persons who have been identified as having a serum serotonin level that is about 25% or more above that of serum serotonin levels in normal subjects.

A patient in need of treatment or prevention for a bone disease (e.g., a low bone mass disease) by the methods of the present invention does not include a patient being treated with a TPH1 inhibitor, another agent that decreases serum serotonin levels, or a serotonin HT1B antagonist, where the patient is being treated with the TPH1 inhibitor, other agent that decreases serum serotonin levels, or serotonin HT1B antagonist for a purpose other than to treat a bone disease. Thus, a patient in need of treatment or prevention for a bone disease by the methods of the present invention does not include a patient being treated with a TPH1 inhibitor for the purpose of treating chemotherapy-induced emesis, carcinoid syndrome, or gastrointestinal disorders such as irritable bowel syndrome.

A patient in need of treatment or prevention for a bone disease by the methods of the present invention does not include a patient being treated with a TPH1 inhibitor for the purpose of treating gastrointestinal diseases and disorders. Examples of specific diseases and disorders include abdominal pain (e.g., associated with medullary carcinoma of the thyroid), anxiety, carcinoid syndrome, celiac disease, constipation (e.g., constipation having an iatrogenic cause, and idiopathic constipation), Crohn's disease, depression, diabetes, diarrhea (e.g., bile acid diarrhea, enterotoxin-induced secretory diarrhea, diarrhea having an iatrogenic cause, idiopathic diarrhea (e.g., idiopathic secretory diarrhea), and traveler's diarrhea), emesis, functional abdominal pain, functional anorectal disorders, functional bloating, functional dyspepsia, functional gallbladder disorders, irritable bowel syndrome (IBS; including IBD-d, IBS-c and IBS-a), lactose intolerance, MEN types I and II, nausea, Ogilvie's syndrome, Pancreatic Cholera Syndrome, pancreatic insufficiency, pheochromacytoma, scleroderma, somatization disorder, sphincter of Oddi disorders, ulcerative colitis, and Zollinger-Ellison Syndrome. A patient in need of treatment or prevention for a bone disease (e.g., a low bone mass disease) by the methods of the present invention does not include a patient being treated with a TPH1 inhibitor for the purpose of treating these diseases and disorders.

A patient in need of treatment or prevention for a bone disease (e.g., a low bone mass disease) by the methods of the present invention also does not include a patient being treated with a TPH1 inhibitor for the purpose of treating the following diseases and disorders: cardiovascular and pulmonary diseases and disorders, such as acute and chronic hypertension, chronic obstructive pulmonary disease (COPD), pulmonary embolism (e.g., bronchoconstriction and pulmonary hypertension following pulmonary embolism), pulmonary hypertension (e.g., pulmonary hypertension associated with portal hypertension), and radiation pneumonitis (including that giving rise to or contributing to pulmonary hypertension). Others include abdominal migraine, adult respiratory distress syndrome (ARDS), carcinoid crisis, CREST syndrome (calcinosis, Raynaud's phenomenon, esophageal dysfunction, sclerodactyl), telangiectasia), serotonin syndrome, and subarachnoid hemorrhage.

Although not considered "patients in need of treatment or prevention for a bone disease," persons who may benefit from treatment or prevention by the administration of the compounds disclosed herein include persons who are known to be in need of therapy to decrease serotonin production in order to treat or prevent a disease or condition resulting from, or exacerbated by, elevated serotonin levels, e.g., chemotherapy-induced emesis, carcinoid syndrome, or gastrointestinal disorders such as irritable bowel syndrome.

A "TPH1 inhibitor" is a substance that reduces the amount of 5-hydroxytryptophan produced from tryptophan by TPH1 in a suitable assay, as compared to the amount of 5-hydroxytryptophan produced from tryptophan by TPH1 in the assay in the absence of the substance. Preferably, the decrease is at least about 10%. Assays for determining the level of TPH1 inhibition of an agent are described in U.S. Patent Application Publication US 2009/0029993.

A "TPH2 activator" is a substance that increases the amount of 5-hydroxytryptophan produced from tryptophan by TPH2 in a suitable assay, as compared to the amount of 5-hydroxytryptophan produced from tryptophan by TPH2 in the assay in the absence of the substance. Preferably, the increase is at least about 10%.

"Selective serotonin reuptake inhibitors (SSRIs)" refers to a class of antidepressants used in the treatment of depression, anxiety disorders, and some personality disorders. They are also typically effective and used in treating premature ejaculation problems. SSRIs increase the extracellular level of the neurotransmitter serotonin by inhibiting its reuptake into the presynaptic cell, increasing the level of serotonin available to bind to the postsynaptic receptor. They have varying degrees of selectivity for the other monoamine transporters, having little binding affinity for the noradrenaline and dopamine transporters. The first class of psychotropic drugs to be rationally designed, SSRIs are the most widely prescribed antidepressants in many countries. SSRIs include: citalopram (CELEXA®, CIPRAMIL®, EMOCAL®, SEPRAM®, SEROPRAM®); escitalopram oxalate (LEXAPRO®, CIPRALEX®, ESERTIA®); fluoxetine (PROZAC®, FONTEX®, SEROMEX®, SERONIL®, SARAFEM®, FLUCTIN® (EUR), FLUOX® (NZ)); fluvoxamine maleate (LUVOX®, FAVERIN®); paroxetine (PAXIL®, SEROXAT®, AROPAX®, DEROXAT®, REXETIN®, XETANOR®, PAROXAT®); sertraline (ZOLOFT®, LUSTRAL®, SERLAIN®), and dapoxetine (no known trade name).

Lrp5 Regulates Bone Development Through More than One Mechanism

The extreme conservation of gene function between mouse and human when it comes to skeletal biology explains why skeletal biology, and especially the study of bone remodeling and homeostasis, has been profoundly influenced by mouse and human genetic studies. Although gene inactivation experiments in mice or molecular cloning of disease genes in humans were designed initially to identify genes important during embryonic development, results of these studies went further than this initial goal by also shedding new light on the molecular bases of skeletal biology after birth. Among the genes identified either through gene deletion experiments or through human genetic studies that turned out to be important for the maintenance of bone mass in adults, one can cite the vitamin D receptor, Interleukin 6, Estrogen receptor α and LDL receptor related protein 5 (Lrp5) (Gong et al., 2001, Cell 107: 513-523; Boyden et al., 2002, N. Engl. J. Med. 346: 1513-1521; Yoshizawa et al., 1997, Nat. Genet. 16: 391-396; Ohshima et al., 1998, Proc. Natl. Acad. Sci. USA 95:8222822-6; Windahl et al., 2002, Trends Endocrinol. Metab. 13:195-200).

The identification of Lrp5 as a regulator of post-natal bone formation is one of the most vivid examples of how developmental studies can profoundly affect the understanding of physiology because this receptor is expressed during development but its function only becomes apparent post-natally. Indeed, loss-of-function mutations in Lrp5 cause osteoporosis pseudoglioma syndrome (OPPG) in humans, a pediatric disease, and gain-of-function mutations in Lrp5 cause high bone mass, a phenotype most often appearing only in adolescents and persisting into adulthood (Gong et al., 2001, Cell 107: 513-523; Boyden et al., 2002, N. Engl. J. Med. 346: 1513-1521; Johnson et al., 1997, Am. J. Hum. Genet. 60:1326-1332). Likewise, skeletogenesis is normal in Lrp5−/− mice and their low bone mass phenotype only develops post-natally (Kato et al., 2002, J. Cell. Biol. 157: 303-314).

The LDL receptor related protein 5 (LRP5) is required for normal bone mass, and a low bone mass phenotype is caused by Lrp5 inactivation in humans and mice (Gong et al., 2001, Cell 107:513-523; Kato et al., 2002, J. Cell. Biol. 157: 303-314). Lrp5−/− mice have low bone mass with no change in osteoclast surface but decreased osteoblast numbers. Real-time PCR analysis of Lrp5−/− molecular signature shows that Lrp5−/− osteoblasts do not show changes in osteoblast-specific gene expression but have decreased expression of cyclin genes (FIG. 1).

Lrp5 and its closest relative Lrp6 are the vertebrate homologues of the *Drosophila* gene arrow that encodes a surface receptor functioning as a co-receptor for Wingless, the *drosophila* homologue of the Wnt proteins (Wehrli et al., 2000, Nature 407:527-530; Tamai et al., 2000, Nature 407:530-535). In vertebrate cells, Wnt signaling is mainly mediated by β-catenin. Upon binding of a Wnt ligand to its receptor, β-catenin is translocated to the nucleus where it cooperates with Lef/Tcf transcription factors to activate gene expression (Logan et al., 2004, Annu Rev. Cell Dev. Biol. 20:781-810; Mao et al., 2001, Mol. Cell, 7:801-809). According to this canonical model, co-transfection of Lrp5 increases the ability of Wnt proteins to enhance the activity of a Tcf-dependent promoter such as the TopFlash promoter (Gong et al., 2001, Cell 107: 513-523; Boyden et al., 2002, N. Engl. J. Med. 346:1513-1521; Mao et al., 2001, Mol. Cell, 7:801-809). Together, the homology of sequence between arrow and Lrp5 and the ability of Lrp5 to favor Wnt signaling through its canonical pathway have led to a model whereby Wnt signaling would regulate bone mass post natally and during adulthood by regulating osteoblast proliferation and function. There is no reason to question the notion that Lrp5 may be a co-receptor for Wnts and that Wnt signaling is involved in the regulation of bone formation (Glass et al., 2005, Dev. Cell 8:751-764; Holmen et al., 2005, J. Biol. Chem. 280:21162-21168; Day et al., 2005, Dev. Cell, 8:739-750; Hu et al., 2005, Development 132:49-60). Nevertheless, there may be additional mechanisms that explain the bone abnormalities observed in either Lrp5 loss- or gain-of-function models.

Lrp5 Regulates Bone Mass in the Periphery Through Serotonin

TPH1 encodes the first enzyme in the biochemical pathway resulting in serotonin synthesis outside the central nervous system. It is viewed as a cell-specific gene mostly expressed in the enterochromaffin cells of the duodenum (Gershon & Tack, 2007, Gastroenterology, 132:397-414). By contrast, serotonin synthesis in the brain relies on TPH2, which is encoded by a different gene expressed in the central nervous system (CNS).

In an effort to elucidate the molecular mechanisms whereby Lrp5 inactivation affects bone formation, a microarray analysis in WT and Lrp5−/− bones was performed. Tryptophan hydroxylase 1 (TPH1) was identified as the gene most highly over expressed in Lrp5−/− bones having low bone mass disease. This result was surprising since it is the opposite of what would be expected given the role of serotonin in the brain, where it increases bone mass. Remarkably, TPH1 expression was normal in mice lacking β-catenin in osteoblasts only (Glass et al., 2005, Dev. Cell 8:751-764).

Figure 7:
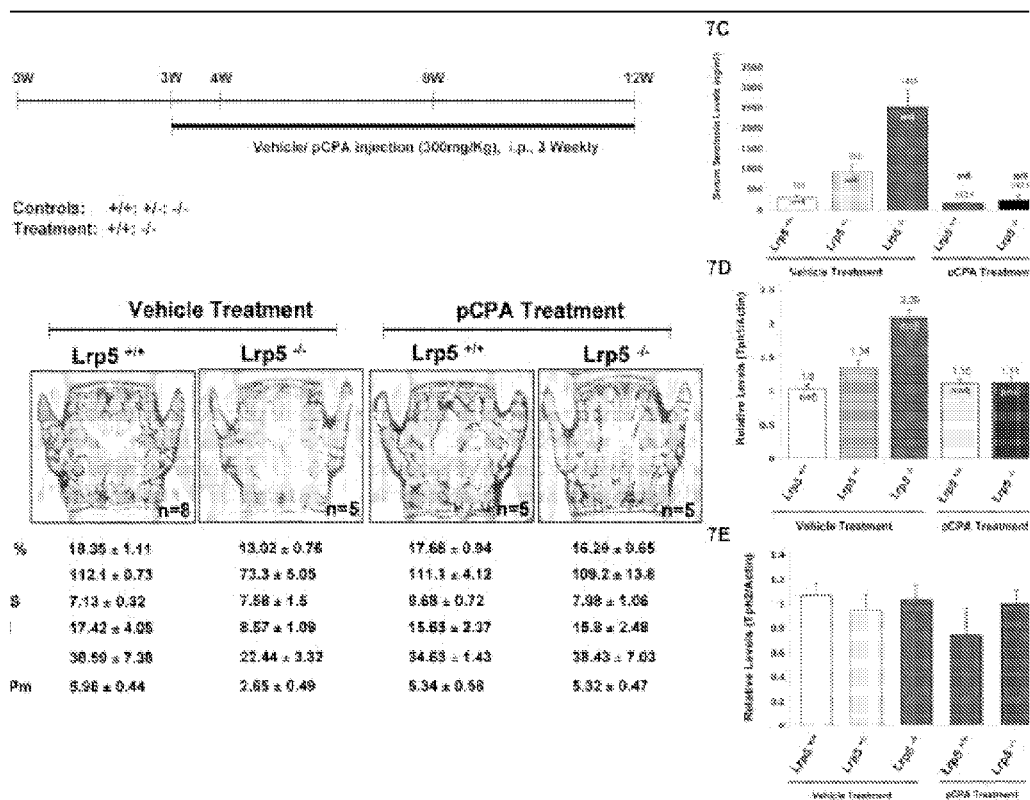
FIG. 7. Tryptophan hydroxylase inhibitor (pCPA) treatment normalizes serum serotonin levels and corrects bone abnormalities observed in Lrp5 −/− mice. Treatment regimen for the pCPA treatment (A), histomorphometric analysis of bone phenotype (B), serum serotonin levels (C), gut Tph1 expression levels (D), brain Tph2 expression upon vehicle and pCPA treatment.

It was shown that TPH1 is overexpressed not only in bone, but also in the duodenum in Lrp5−/− mice, where TPH1 expression is more than 1300-fold higher than in osteoblasts. It was further discovered that serum serotonin levels are normal in newborn Lrp5−/− mice but increase steadily with age as their bone phenotype develops. This is consistent with the fact that the low bone mass phenotype in Lrp5−/− mice is not present at birth but appears later during development. Further discoveries showed that treating Lrp5−/− mice with an inhibitor of serotonin synthesis called pCPA corrects their low bone phenotype (FIG. 7). Finally, it was discovered that TPH1 expression is increased in aging animals, i.e., when bone mass is well-known to decrease. Based on these and additional data described below, it can be conclude that LRP5, through yet unknown mechanisms, is a negative regulator of serotonin synthesis in the duodenum, and that increasing serum serotonin signaling negatively impacts osteoblast proliferation and function.

Serotonin, a Multifaceted Molecule

Serotonin (5-hydroxytryptamine, 5-HT) is a biogenic amine that functions both as a neurotransmitter in the mammalian central nervous system and as a hormone in the periphery, where most of it is produced (Gershon et al., 1990, Neuropsychopharmacology, 3:385-395.). Serotonin is generated through an enzymatic cascade in which L-tryptophan is converted into L-5-hydroxytryptophan by an enzyme called tryptophan hydroxylase (TPH). This intermediate product is then converted to serotonin by an aromatic L-amino acid decarboxylase. There are two TPH encoding genes, TPH1 and TPH2, which are 71% identical in amino acid sequence and about 90% similar in the catalytic domain. While TPH1 controls serotonin synthesis in the periphery, TPH2 is responsible for serotonin synthesis in the brain (Walther et al., 2003, Science 299:76). Given that serotonin cannot cross the blood-brain barrier, these two genes are therefore solely responsible for regulating the level of this molecule in the periphery and in the brain, respectively. As a consequence, designing TPH1 inhibiting compounds that cannot cross the blood brain barrier is one of the ways to achieve selective inhibition of TPH1 in the periphery and decrease serotonin levels in this physiologic compartment.

TPH1 is expressed almost exclusively in cells of the duodenum, and it is responsible for the synthesis of peripheral serotonin, which represents 95% of total serotonin (Gershon & Tack, 2007, 132:397-414). TPH1 expression in any tissues other than duodenum is at least 100-1000 fold lower. Thus, TPH1 can be viewed as a duodenum-specific gene and peripheral serotonin production as a duodenum-specific process.

Besides its role as a neuromediator, and because of its abundance in the general circulation, serotonin has been implicated in a variety of developmental and physiological processes in peripheral tissues, including heart development, gastrointestinal movement, liver regeneration and mammary gland development (Lesurtel et al., 2006, Science, 312:104-107; Matsuda et al., 2004, Dev. Cell, 6:193-203; Nebigil et al., 2000, Proc. Natl. Acad. Sci. USA 97:9508-9513). To carry out its functions, serotonin can bind to at least 14 receptors, most of them being G-protein coupled receptors (GPCRs). One or several serotonin receptors are present in most cell types, including osteoblasts (Westbroek et al., 2001, J. Biol. Chem. 276:28961-28968).

Type 1 Collagen, Osteocalcin, Regulatory Genes Affecting Osteoblast Differentiation and/or Extracellular Matrix Protein Synthesis (Runx2 and Osterix and Atf4) and Osteoclast Differentiation (RankL and Osteoprotegrin) are Normal in Lrp5-Deficient Mice Lrp5−/− mice are indistinguishable by all accounts from WT mice at birth, but afterward progressively develop a significant low bone mass phenotype (Kato et al., 2002, J. Cell. Biol. 157: 303-314). Histological and histomorphometric analyses established that this low bone mass phenotype is due to a decrease in bone formation while bone resorption is unaffected. Importantly, osteoblast differentiation is not affected in the mutant mice while osteoblast proliferation is decreased two fold in the absence of Lrp5. See FIG. 1, which shows that Lrp5−/− mice have low bone mass (A) with no change in osteoclast surface (B) but have decreased osteoblast numbers (C).

Real-Time PCR Analysis of Lrp5−/− Molecular Signature.

To delineate the molecular signature of the disruption of Lrp5 signaling, the expression of multiple genes characterizing either the osteoblast lineage or determining cell proliferation was studied using Lrp5−/− mice (Kato et al., 2002, J. Cell. Biol. 157: 303-314). The expression of genes particularly relevant to bone formation was first analyzed. Expression of type I collagen and Osteocalcin, two genes highly expressed in osteoblasts, is normal in Lrp5−/− bones (data not shown). This finding is important as it establishes that the bone phenotype of the Lrp5−/− mice is not caused by a defect in type I collagen synthesis, the main constituent of the bone extracellular matrix (ECM). Expression of regulatory genes affecting osteoblast differentiation and/or extracellular matrix protein synthesis was also studied. Expression of Runx2 and Osterix and Atf4, the three known osteoblast-specific transcription factors, was unaltered in Lrp5−/− bones (FIG. 1D). Likewise, expression of RankL and Osteoprotegerin (OPG), two regulators of osteoclast differentiation expressed by osteoblasts is unaffected by Lrp5 deletion (FIG. 1D). This latter feature distinguishes Lrp5−/− from β-catenin osteoblast-specific deficient (βcatob−/−) bones (Glass et al., 2005, Dev. Cell 8:751-764; Holmen et al., 2005, J. Biol. Chem. 280:21162-21168).

Given the decrease in osteoblast proliferation characterizing Lrp5−/− bones, the expression of marker genes of cell cycle progression was also studied. Expression of Cyclin D1, D2 and E1, three genes necessary for the transition from the G1 to S phase of the cell cycle, was decreased in the Lrp5−/− bones (FIG. 1E). Based on these results, it appears that at the molecular level the low bone mass phenotype caused by the absence of Lrp5 is purely a cell proliferation defect while expression of type I collagen, the main protein constituent of the bone extracellular matrix (ECM), and of all 3 known osteoblast-specific transcription factors is normal.

Low Bone Phenotype in Lrp5−/− Mice is not Due to Abnormal Wnt Signaling

Figure 2:
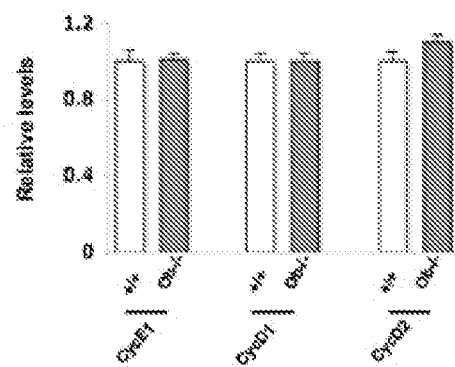
FIG. 2. Real-time PCR analysis of cell cycle marker genes in β-cat$_{ob}$ −/− bones (ob−/−).

Given the sequence homology and convincing experimental arguments suggesting that Lrp5 could be a co-receptor for Wnt and may be part of the Wnt canonical signaling pathway, whether the bone phenotype of Lrp5−/− mice was due to abnormal Wnt signaling was investigated. To that end, mice lacking β-catenin in osteoblasts only were analyzed (Glass et al., 2005, Dev. Cell 8:751-764). It had been shown earlier that mice lacking β-catenin only in osteoblasts developed a low bone mass phenotype and that this phenotype was caused by a totally different mechanism than the one operating in the Lrp5−/− mice. Indeed, β-cat$_{ob}$ −/− mice have a normal number of osteoblasts, an increase of the number of osteoclasts and an increase in elimination of deoxypyridinoline, abnormalities that are secondary to a decrease in OPG expression (Glass et al., 2005, Dev. Cell 8:751-764). In addition, unlike in Lrp5−/− bones, expression of the cell cycle markers Cyclin D1, D2 and E1 normal in the in β-cat$_{ob}$ −/− bones (FIG. 2). Thus, the cellular and molecular bases of the β-cat$_{ob}$ −/− and Lrp5−/− mice bone phenotype appear to be quite different. Although these unexpected results do not rule out that Lrp5 could act as a Wnt co-receptor, there was still a possibility that other mechanisms could explain how the loss of Lrp5 could affect bone formation so specifically. To that end, a microarray analysis looking for genes abnormally expressed in Lrp5−/− compared to WT bones was performed.

TPH1 is Overexpressed in Bone and Duodenum in Lrp5−/− Mice

Figure 3:
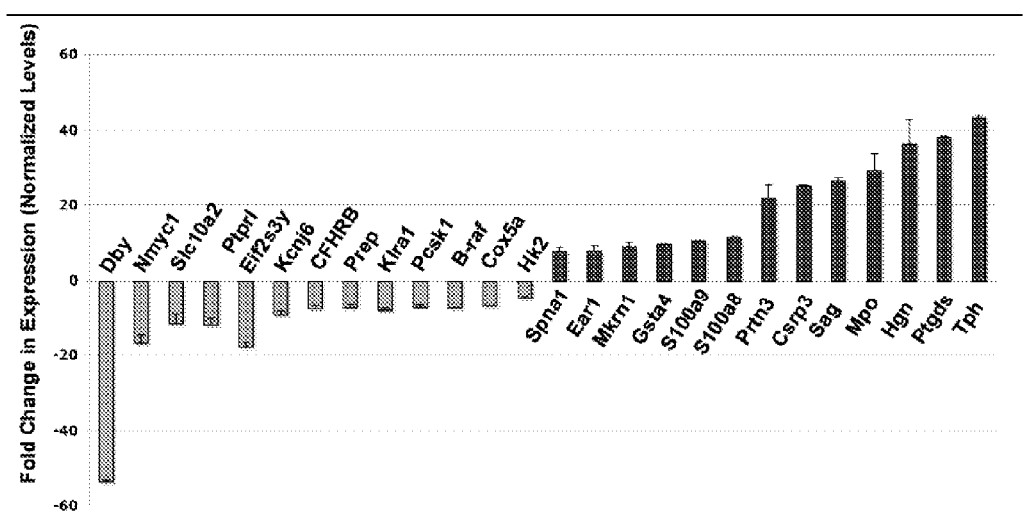
FIG. 3. Microarray analysis of Lrp5−/− bones reveals an increased expression of Tryptophan hydroxylase 1 (Tph1) gene expression compared to wt bones. Gray and black bars indicate a decrease and an increase in gene expression, respectively. Genes including and to the left of Hk2 showed decreased expression while genes including and to the right of Spna1 showed increased expression.

A microarray analysis of Lrp5 −/− bones surprisingly showed that one of the genes most highly over expressed was TPH1 (FIG. 3). It is important to emphasize that TPH1 expression is normal in β-cat$_{ob}$ −/− bones and osteoblasts, further underscoring the molecular differences that exist between these two mutant mouse strains. Given the rather confined pattern of expression of TPH1 in WT mice, where it is restricted to the duodenum, its overexpression in Lrp5 −/− bones was surprising and raised the question whether it was an osteoblast-specific feature.

Figure 4:
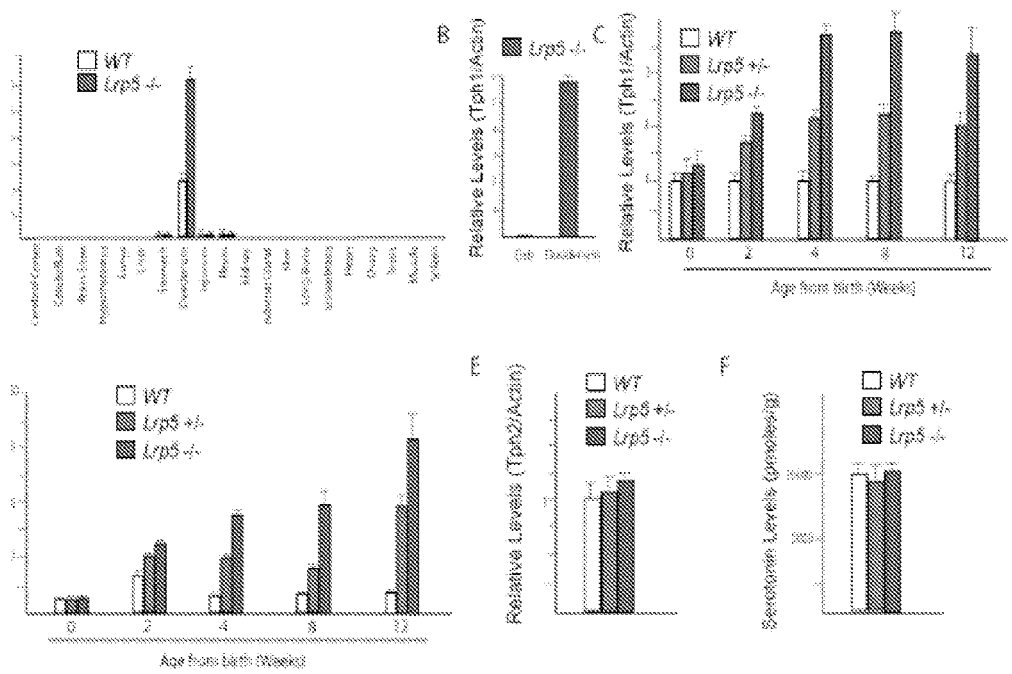
FIG. 4. Tph1 expression is increased in the duodenum of Lrp5−/− mice (A). Tph1 expression is 1000 fold higher in duodenum than in bone in Lrp5−/− mice (B). Tph1 expression in duodenum (C) and serum serotonin levels (D) increase progressively with age in Lrp5 −/− mice. Neither Tph2 expression nor serotonin levels are altered in the brain of Lrp5−/− mice (E and F).
Figure 5:
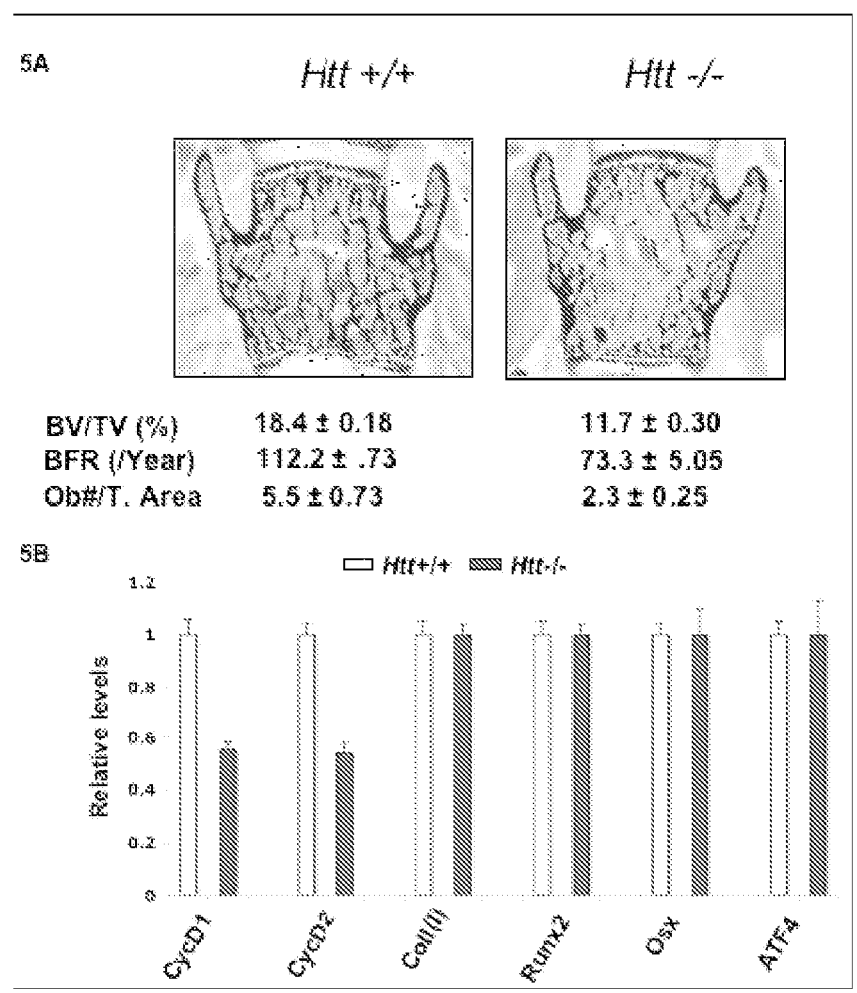
FIG. 5. 5Htt −/− mice have low bone mass and decreased osteoblast numbers (A). Realtime PCR analysis of gene expression in bone revealed a decreased expression of cyclins in 5Htt−/− mice while no changes in the expression of osteoblast differentiation markers or type I collagen genes can be detected (B).
Figure 6:
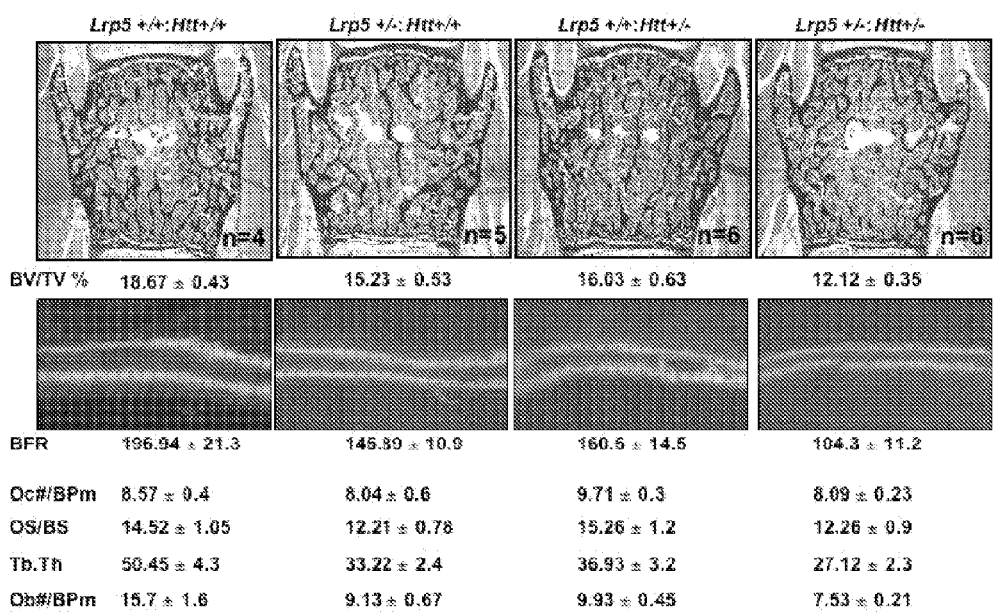
FIG. 6. Histologic and histomorphometric comparison of Lrp5/5Htt (Htt) compound mice. Lrp5+/−;Htt +/− double heterozygous mice have a more severe decrease in bone mass than the Lrp5 +/− or 5Htt +/− single heterozygous mice. This is also true for the decrease in osteoblast numbers.

To answer this question, TPH1 expression in all tissues of WT and Lrp5 −/− mice was analyzed by qPCR. It was found that TPH1 expression was also increased 3 fold in duodenum of Lrp5 −/− compared to WT mice (FIG. 4A). However, TPH1 expression remained more than 1300 fold higher in duodenum than in osteoblasts in Lrp5−/− mice (FIG. 4B). These latter data suggested for the first time that the bone phenotype observed in Lrp5 −/− mice may primarily have a gut origin. The increase in expression of TPH1 was also observed, albeit as expected to a lower level, in Lrp5 +/− mice (FIG. 4C). This is an important observation since heterozygous Lrp5+/− mice also have a low bone mass phenotype. Importantly, in agreement with the absence of a bone phenotype in newborn Lrp5−/− mice, TPH1 expression was not elevated in newborn mice (FIG. 4C). The changes in TPH1 expression were reflected in increased serum serotonin levels in both Lrp5 +/− and Lrp5 −/− mice (FIG. 4D); which were absent at birth but present at 2, 4 and 8 weeks of age. Moreover these changes preceded the appearance of the bone phenotype in Lrp5 −/− mice.

By contrast, the expression of TPH2 in the brain was not affected in Lrp5−/− mice and serotonin content in the brain was similar in WT and Lrp5 −/− mice (FIGS. 4E and 4F). This observation is consistent with the fact that serotonin does not cross the blood brain barrier (Mann et al., 1992, Arch. Gen. Psychiatry, 49:442-446) and indicates that the link between Lrp5 function and serotonin biology has to be with peripheral serotonin.

Expression of the TPH1 gene was decreased compared to wild type (WT) in mice engineered with a mutation causing high bone mass in humans in one allele (Lrp5 +/act duo) or both alleles (Lrp5 act duo) of the mouse Lrp5 gene specifically in cells of the duodenum. RNA was extracted from duodenum of one-month-old mice and expression of the TPH1 gene quantified by real-time PCR (FIG. 11).

TABLE 1

|  | WT | Lrp5 +/ act duo | Lrp5 act duo |
|---|---|---|---|
| Relative Tph1 expression | 1 | 0.77 ± 0.000 | 0.54 ± 0.005 |

Figure 11:
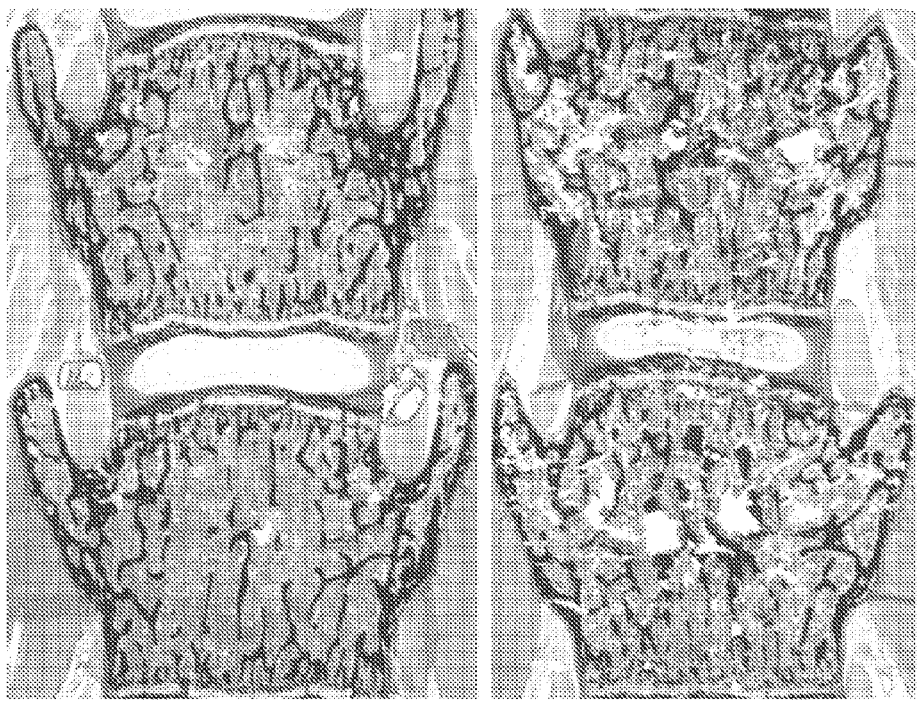
FIG. 11. Mice engineered to express in both alleles of their Lrp5 genes of their duodenal cells a mutation that in humans leads to high bone mass show a higher bone mass than wild-type (WT) mice. Vertebrae were embedded in plastic medium, sectioned at 5 micrometers and stained with the von Kossa/Van gieson reagent. The bone matrix was stained in black.

Mice engineered with a mutation causing high bone mass in human in the Lrp5 gene specifically in cells of the duodenum (Lrp5 act duo) show a higher bone mass than wild type mice (FIG. 11).

Taken together, the results of these analyses indicated that the increase in TPH expression caused by Lrp5 deficiency was restricted to TPH1 (and therefore to peripheral serotonin) and that it occurs both in osteoblasts and duodenal cells although its expression is at least 1300-fold higher in duodenum. This result raises two questions: is the increase in serum serotonin the cause of the Lrp5−/− mice bone phenotype and is this an endocrine effect mediated by the production of serotonin by duodenal cells and/or an autocrine effect related to the local production of serotonin by osteoblasts?

Lrp5−/− and 5Htt−/− Mice have Identical Bone Phenotypes

If the bone phenotype of the Lrp5 −/− mice is secondary to an increase in the level of serum serotonin, then a mouse model characterized by an increase in serum serotonin should have not only the same histological bone phenotype as the Lrp5−/− mice but also the same molecular signature defined previously, i.e., decreased cyclin gene expression and normal type I collagen expression (FIG. 1). This is what was observed.

The Serotonin Synthesis Inhibitor (pCPA) Rescues the Bone Phenotype of Lrp5 −/− Mice Consistent with the conclusion that the increase in serum serotonin level is responsible fully or partly for the bone phenotype of the Lrp5−/− mice is the discovery that pCPA, a serotonin synthesis inhibitor (Eldridge et al., 1981, Ann. Rev. Physiol. 43:121-135), prevented the appearance of the Lrp5−/− bone phenotype by decreasing serotonin production. WT and Lrp5−/− mice were treated with 300 mg/kg pCPA intraperitoneally three times per week, from 3 weeks to 12 weeks of age (FIG. 7A) and the changes in serum serotonin levels, TPH1 expression in gut and TPH2 expression in brain stem were analyzed. Bone histomorphometry was also performed. As shown in FIG. 7B, pCPA treatment corrected the bone abnormalities observed in Lrp5−/− mice without overtly affecting bone mass in WT mice. This rescue of the Lrp5 −/− phenotype was achieved by normalization of the gut TPH1 mRNA and of serum serotonin levels (FIGS. 7C and 7D). Brain TPH2 mRNA levels were not affected in the treated mice, further demonstrating that the phenotype observed in Lrp5−/− bones is directly caused by changes in serum, not brain, serotonin levels.

Serotonin Binds to Specific Serotonin Receptors in Osteoblasts

From the working hypothesis that Lrp5 acts on bone formation through serum serotonin, a third inference was tested:

osteoblasts should express some serotonin receptors, and serotonin treatment of osteoblasts should blunt the expression of Cyclin D1, D2 and E1 without affecting the expression of α(I) collagen, Runx2 or Osteocalcin. To address the first part of this point, the expression of each of the known serotonin receptors was analyzed by qPCR in WT osteoblasts. The expression of three different serotonin receptors in osteoblasts, all belonging to the G-protein coupled receptor superfamily was detected (Noda et al., 2004, Mol. Neurobiol. 29:31-39). HT1B was the most highly expressed receptor. It is coupled to $G_i$-type G proteins and inhibits adenylyl cyclase activity. HT2B is the second most abundant receptor and is coupled to the G proteins that activate a phosphatidyl-inositolcalcium second messenger system. Lastly, HT2A is the third receptor significantly expressed in osteoblasts. Like HT2B, it is coupled to the G proteins that activate a phosphatidylinositol-calcium second messenger system. Remarkably, HT1B, the most highly expressed serotonin receptor in osteoblasts, is also more highly expressed in these cells than in any other cells. Thus, there is at least a partially cell-specific signaling pathway occurring in osteoblasts that could be able to specifically transduce serotonin signaling in these cells. See FIG. 8 which shows real-time PCR analysis of the expression of known serotonin receptors expression in WT osteoblasts (A) and of the expression of cyclins and osteoblast-specific genes in primary osteoblasts treated with serotonin or vehicle (B).

To test whether serotonin regulates the expression of cyclins in osteoblasts, a real-time PCR analysis of cyclin expression in primary osteoblasts treated with serotonin or vehicle was performed. As shown in FIG. 8B, expression of Cyclin D1 and D2 was decreased in the presence of serotonin. In contrast, expression of Runx2, Osteocalcin and Type I collagen was not modified (FIG. 8B). That the molecular signature of serotonin treatment of osteoblasts is similar to the one displayed in absence of Lrp5 further strengthens the hypothesis of a functional link between Lrp5 and serotonin signaling in osteoblasts.

Figure 8:
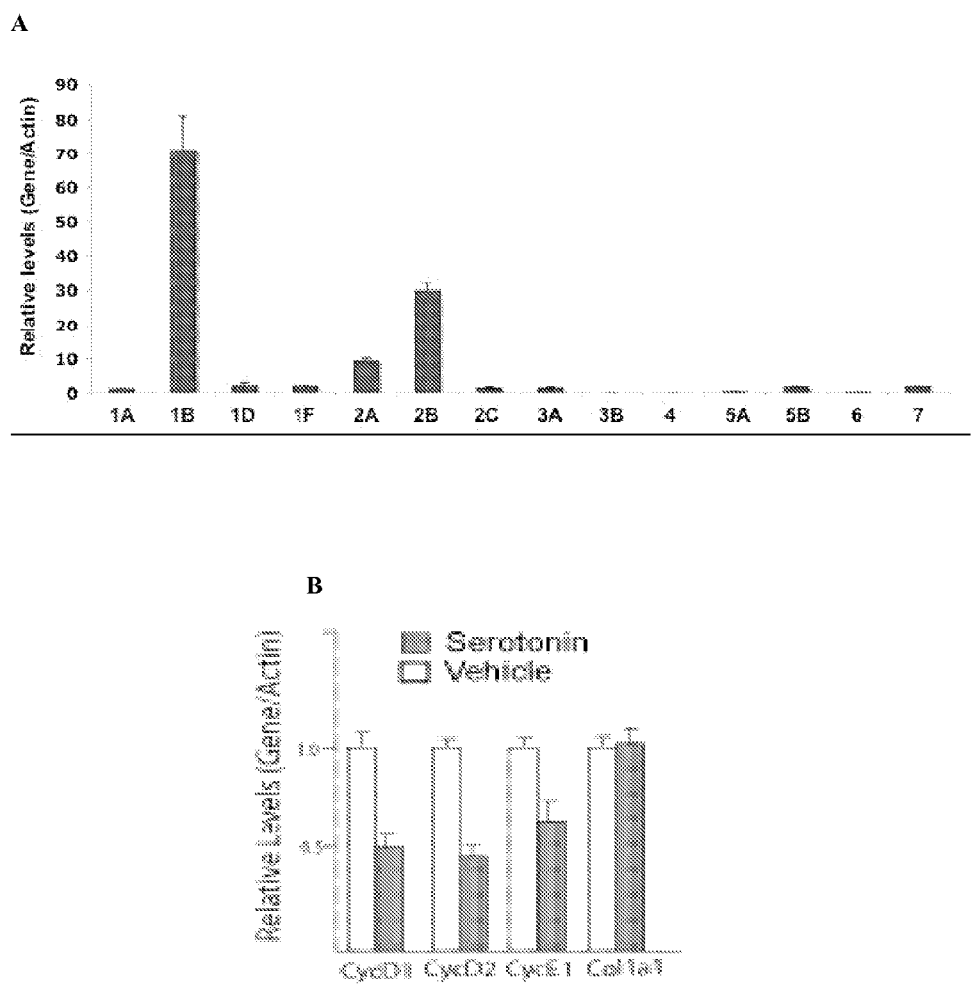
FIG. 8. Real-time PCR analysis of the expression of known serotonin receptors expression in WT osteoblasts (A) and of the expression of cyclins and osteoblast-specific genes in primary osteoblasts treated with serotonin or vehicle (B).
Figure 9:
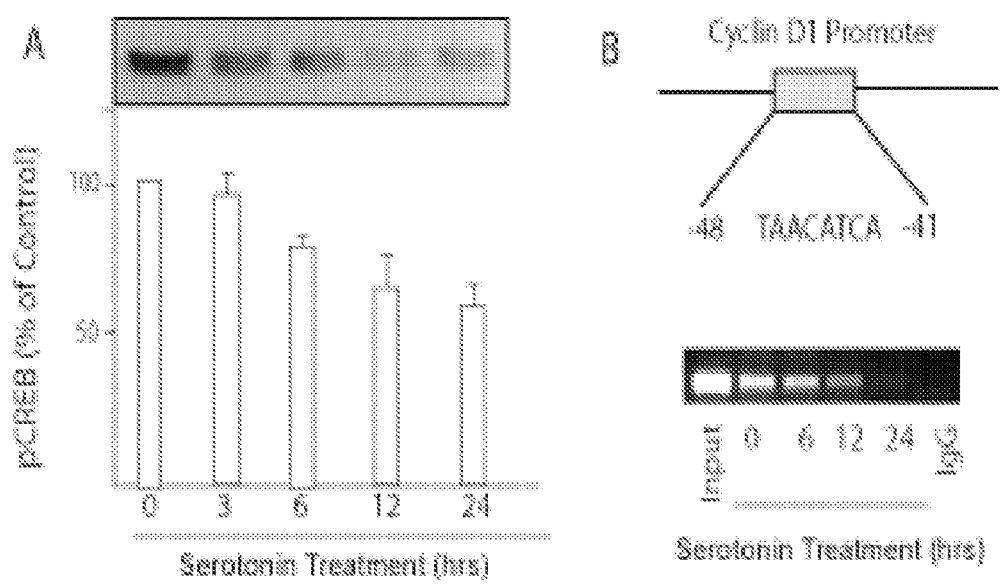
FIG. 9. Western blot analysis of CREB phosphorylation (A) and ChIP analysis of CREB binding to the Cyclin D1 promoter (B) in primary osteoblasts treated with serotonin for the indicated times.

Decreased expression of Cyclin D1 is a major feature of both Lrp5 deficiency and serotonin treatment of osteoblasts (FIGS. 1 and 8). One transcription factor that is known to modulate the expression of cyclin genes and is expressed in osteoblasts is CREB (Fu et al., 2005, Cell 122:803-815). Therefore, whether serotonin could decrease CREB activity in these cells was tested. As shown in FIG. 9A, serotonin treatment significantly decreased CREB phosphorylation in primary osteoblasts. Furthermore, a CREB binding site in the Cyclin D1 mouse promoter was identified and it was shown using ChIP assays that serotonin decreased binding of CREB to this promoter (FIG. 9B). These two observations raise the hypothesis that CREB could be mediating serotonin action on osteoblasts.

TPH1 Expression is Increased in Aging Animals

Figure 10:
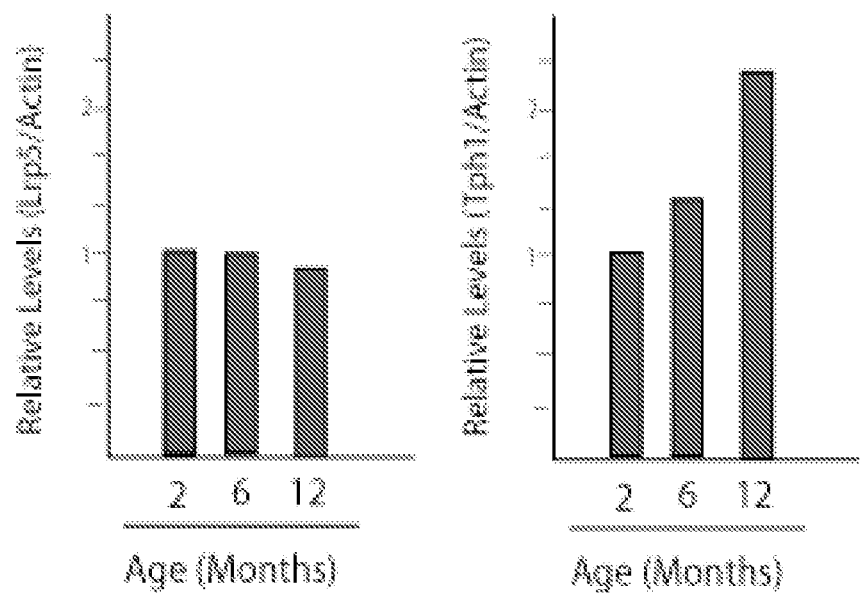
FIG. 10. Real-time PCR analysis of the expression of Tph1 (A) and Lrp5 (B) in duodenum of WT mice at the indicated ages.

It has been shown in *C. elegans* that TPH1 expression increases with age (Murakami et al., 2007 Feb. 28 [Epub ahead of print], Neurobiol Aging). To test if this was also the case in mammals, TPH1 expression in aging mice was analyzed. Using real time PCT, it was shown that, while expression of Lrp5 remained stable with age, expression of TPH1 doubled in 1 year-old compared to 2 month-old mice (FIG. 10). Since serum serotonin acts as a negative regulator of bone formation, such an increase in TPH1 expression with age exacerbates the bone loss associated with aging and therefore is a target for therapeutic intervention for age-related bone loss.

Methods of Diagnosis and Treatment

The results disclosed herein show that elevated serum serotonin decreases bone mass and low serum serotonin increases it. Thus, certain embodiments of the invention are directed to methods for treating or preventing diseases associated with abnormally low bone mass (such as osteoporosis and OPPG) by administering compounds disclosed herein that decrease the level of peripheral serum serotonin. Other embodiments are directed to new pharmaceutical compositions comprising the compounds disclosed herein for treating or preventing low bone mass diseases.

One embodiment of the invention is directed to a method for determining if a patient is at risk of developing a low bone mass disease by determining the patient's level of serum serotonin and then administering a compound disclosed herein that is a TPH1 inhibitor to the patient if the patient is at risk of developing a low bone mass disease. If the patient's level of serum serotonin is significantly higher (e.g., more than about 25% higher) than the level in a normal subject, then the patient is at risk of developing abnormally low bone mass and TPH1 inhibitors that reduce serotonin synthesis, optionally with serotonin receptor antagonists (that target HT1B, HT2A and/or HT2B), can be administered to reduce (and preferably normalize) serum serotonin levels and, optionally, block the effect of serotonin on serotonin receptors, thereby preventing low bone mass from developing or minimizing the extent of bone loss, should such loss develop. Patient monitoring will determine if an abnormal serum serotonin profile is chronic. If it is chronic, then the patient may need to continue treatment over a prolonged period (e.g., for one month, six months, one year, two years, three years, or many years) to normalize serum serotonin levels and/or maintain normal levels of serum serotonin.

When a patient's level of serum serotonin is compared to the level of serum serotonin in a normal subject, it should be understood that "normal subject" refers to a person who is matched to the patient in those characteristics that would be expected to affect serum serotonin levels, e.g., gender, age, general health, medications being taken, etc.

Methods of Treatment and Prevention of Low Bone Mass Diseases

The present invention provides a method of preventing or treating a low bone mass disease in a patient known or suspected to be in need of such prevention or treatment comprising administering to the patient a therapeutically effective amount of a compound disclosed herein that decreases serum serotonin levels. In certain embodiments, the method comprises administering to the patient therapeutically effective amounts of two or more compounds disclosed herein that decrease serum serotonin levels.

In certain embodiments, the compounds disclosed herein reduce serum serotonin to a level that is at least about 10% less than the level before treatment with the compounds disclosed herein. In certain embodiments, the compounds disclosed herein reduce serum serotonin to a level that is about 10% less, about 20% less, about 30% less, about 40% less, about 50% less, about 60% less, about 70% less, about 80% less, or about 90% less, than the level before treatment with the compounds disclosed herein.

Synthesis of the compounds described herein can be carried out by methods similar to those disclosed in U.S. Patent Application Publication 2007/0191370, U.S. Patent Application Publication 2008/0153852, U.S. Patent Application Publication 2009/0005381, and U.S. Patent Application Publication 2009/0029993. Moieties such as A, $X_1$, D, and E can be prepared and linked according to the methods described those patent applications. By choosing suitable starting materials for the remaining portion of the structures disclosed herein, the remaining portion can be incorporated with the A-X-D, A-X-D-E, or other portions in the final structure and thus the compounds disclosed herein can be prepared.

One skilled in the art would be guided by Examples 9-13 herein and could, for example, choose intermediate Compound 18 from Scheme 2 of Example 10

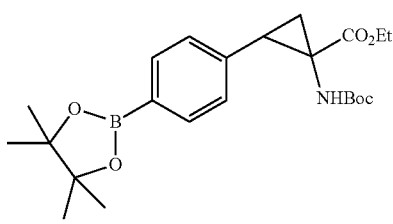

and link intermediate Compound 18 to suitable moieties such as A, $X_1$, D, and E that had been prepared according to the disclosures of the patent application described above. By choosing other intermediates similar to intermediate Compound 18 (e.g., a compound similar to intermediate Compound 18 but having a cyclobutyl group or a cyclopentyl group rather than a cyclopropyl group), one skilled in the art could readily synthesize other α-amino carboxylic acid ester having a 3, 4, or 5-membered ring falling within the generic structures disclosed herein and/or related to the end compound (Compound 20) produced by Scheme 2 of Example 10.

In a like manner, by suitable choices of intermediates and judicious application of the teachings of the prior art and the disclosures herein, one skilled in the art could readily synthesize the compounds disclosed herein falling within the other generic structures disclosed herein and related to the end compounds produced by Scheme 1 in Example 9, Scheme 3 in Example 11, Scheme 4 in Example 12, and Scheme 5 in Example 13.

Synthesis of the compounds within the generic formulas described herein can also be carried out by methods similar to those disclosed in International Patent Publication WO 2007/089335, International Patent Publication WO 2008/073933, International Patent Publication WO 2009/123978, and International Patent publication WO 2010/056992. Moieties such as A, $X_1$, D, and E can be prepared and linked according to the methods described in WO 2007/089335, in particular the methods disclosed at pages 35-41. Further methods that can turned to for guidance are shown on pages 14-17 of WO 2008/073933. By choosing suitable starting materials for the remaining portion of the structures disclosed herein, the remaining portion can be incorporated with the A-$X_1$-D or A-$X_1$-D-E portion in the final structure and thus the compounds of the present invention can be prepared.

The present invention also encompasses the use of certain derivatives of the TPH1 inhibitors disclosed herein. For example, prodrugs of the TPH1 inhibitors could be produced by esterifying the carboxylic or other acid functions of the TPH1 inhibitors with a lower alcohol, e.g., methanol, ethanol, propanol, isopropanol, butanol, etc. The use of prodrugs of the TPH1 inhibitors that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the TPH1 inhibitors are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the TPH1 inhibitors disclosed herein can be found in publications such as *Design of Prodrugs*, Bundgaard, A. Ed., Elsevier, 1985; *Design and Application of Prodrugs, A Textbook of Drug Design and Development*, Krosgaard-Larsen and H. Bundgaard, Ed., 1991, Chapter 5, pages 113-191; and Bundgaard, H., Advanced Drug Delivery Review, 1992, 8, pages 1-38.

In certain embodiments, the compounds disclosed herein inhibit TPH1 without significantly affecting the level of brain-derived serotonin. Methods of obtaining such inhibitors include: (1) screening for compounds that inhibit TPH1 to a much greater extent than TPH2; and (2) screening for compounds that, while they inhibit both TPH1 and TPH2, cannot cross the blood brain barrier and thus are effectively specific for TPH1 when administered to the patient outside the central nervous system. Of course, compounds that both inhibit TPH1 to a much greater extent than TPH2 and cannot cross the blood brain barrier are also suitable. Preferably, compounds that inhibit TPH1 to a much greater extent than TPH2 have an $IC_{50}$ for TPH2 that is at least about 10-fold greater than their $IC_{50}$ for TPH1.

In certain embodiments, the compounds disclosed herein are TPH1 inhibitors that do not significantly affect the level of expression of Type 1 collagen, osteocalcin, Runx2, Osterix, or Atf4 in osteoblasts. In certain embodiments, the compounds disclosed herein are TPH1 inhibitors that decrease the expression of Cyclin D1, D2 and E1 in osteoblasts.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

A chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

If the stereochemistry of a structure or a portion of a structure is not indicated with, for example, bold or dashed lines, the structure or the portion of the structure is to be interpreted as encompassing all stereoisomers of it, unless the chemical name associated with the structure indicates otherwise. Similarly, names of compounds having one or more chiral centers that do not specify the stereochemistry of those centers encompass pure stereoisomers and mixtures thereof. Moreover, any atom shown with unsatisfied valences is assumed to be attached to enough hydrogen atoms to satisfy the valences. When the stereochemistry of a structure or a portion of a structure is indicated with, for example, a bold or dashed line, the use of that structure in the methods describe herein encompasses the use of the indicated stereochemistry substantially free of any of the non-indicated structure. For example, such use includes the use of the indicated structure where the indicated structure is present in an enantiomeric excess of 95%, 96%, 97%, 98%, 99%, or 99.5%.

In certain embodiments of the invention, a therapeutically effective amount of one or more of the compounds described herein is administered in combination with other compounds that are known to increase bone mass to a subject who has or is at risk of developing a low bone mass disease in order to treat or prevent such disease. In certain embodiments, the other compound is a bisphosphonate.

The efficacy of low bone density therapy by administering TPH1 inhibitors can be monitored by measuring bone density or bone mass changes before and over time after treatment to determine drug efficacy. Techniques for measuring bone mass include those techniques well known to those of skill in the art including, but not limited to, skeletal X-rays, which show the lucent level of bone (the lower the lucent level, the higher the bone mass); classical bone histology (e.g., bone volume, number and aspects of trabiculi/trabiculations, numbers of osteoblast relative to controls and/or relative to osteoclasts); and dual energy X-ray absorptiometry (DEXA) (Levis & Altman, 1998, Arthritis and Rheumatism, 41:577-587) which measures bone mass and is commonly used in osteoporosis. BFR means bone formation rate. Any method known in the art can be used to diagnose a person as having, or being at risk of developing, a low bone mass diseases, or to determine the efficacy of therapy using the compounds disclosed herein.

The present invention provides methods of preventing or treating a low bone mass disease in a patient known or suspected to be in need of such prevention or treatment comprising administering to the patient a therapeutically effective amount of a compound disclosed herein that is a TPH1 inhibitor together with a therapeutically effective amount of a serotonin receptor antagonist.

In certain embodiments, the serotonin receptor antagonist is an HT1B, HT2A or HT2B receptor antagonist. In preferred embodiments, the serotonin receptor antagonist is an HT1B antagonist.

The serotonin receptor antagonist may be one of the many known antagonists of peripheral serotonin receptors HT1B, HT2A or HT2B that are present on osteoblasts. Antagonists that are selective for HT1B, HT2A or HT2B receptors are preferred. The efficacy of low bone density therapy by administering a compound disclosed herein that is a TPH1 inhibitor together with HT1B, HT2A or HT2B antagonists can be monitored by measuring bone density changes before and over time after treatment to determine drug efficacy. Diseases associated with low bone mass can be treated with a compound disclosed herein that is a TPH1 inhibitor together with HT1B antagonists such as those listed in Table 2 below.

TABLE 2

| | |
|---|---|
| selective 5-HT1B antagonist GR 55562 | Mlinar and Corradetti, Neurosci., 2003, 18: 1559-1571 |
| elzasonan AZD1134 AR-A2 | U.S. Patent Application Publication 2005/0203130 |
| trazodone hydrochloride (antidepressant) | U.S. Pat. No. 7,198,914 |
| highly selective 5-HT 1B antagonist (SB216641) | U.S. Patent Application Publication 2006/0135415 |
| the selective antagonist at terminal 5-HT$_{1B}$ receptors, N-[3-(2-dimethylamino) ethoxy-4-methoxyphenyl]-2'-methyl-4'-(5-methyl-1,2,4-oxadiazol-3-yl)-(1,1'-biphenyl)-4-carboxamide (SB216641, 0.1-0.8 mg/kg) | Rojas-Corrales et al., Eur. J. Pharmacol., 511: 21-26 |
| GR 127,935 Mixed HT1B/1D antagonist | Naunyn Schmiedebergs Arch. Pharmacol., 1997, 355: 423-430; Wurch, et al., British J. Pharmacol., 1997, 120: 153-159 |
| Cyanopindolol | J. Neurochem., 2000, 75: 2113-2122 |

TABLE 2-continued

| | |
|---|---|
| -GR 125,743 Methiothepin ketanserin | 2'-Methyl-4-(5-methyl-[1,2,4]oxadiazol-3-yl)-biphenyl-4-carboxylic acid [4-methoxy-3-(4-methyl-piperazin-1-yl)-phenyl]-amide (GR 127,935), ketanserin and methiothepin and each behaved as silent, competitive antagonists at rb 5-HT1B receptors British Journal of Pharmacology (1997) 120, 153 ± 159 |
| ICS 205-930 (Sandoz) is a selective antagonist at 5-hydroxytryptamine3 receptors and exerts marked effects on gastrointestinal motility in animalsGut specific | Br J Clin Pharmacol. 1989 Sep. 28(3): 315-322 |
| pindolol a beta-adrenoceptor blocker/5-hydroxy-tryptamine$_{1A/1B}$ receptor antagonist | Pindolol is also a nonselective beta blocker; rapidly and well absorbed from the GI tract |
| AR-A000002—A Novel Selective 5-HT$_{1B}$ Antagonist anxiolytic and antidepressant potential of the selective 5-HT$_{1B}$ antagonist, AR-A000002 ((R)-N-[5-Methyl-8-(4-methylpiperazin-1- yl)-1,2,3,4-tetrahydro-2-naphthyl]-4-morpholinobenzamide). AR-A000002 functions as a 5-HT$_{1B}$ antagonist in vivo | Journal of Pharmacology And Experimental Therapeutics Fast Forward First published on Nov. 25, 2002; |
| cyanopindolol, 5-HT-moduline and methiothepin | Daws, et al., Neuroscience Letters, 1999, 266: 165-168; Daws, et al., J. Neurochem., 2000, 75: 2113-2122 |
| GR 55562, a selective 5-HT1B antagonist selective 5-HT$_{1B}$ receptor antagonist 3-[3-(dimethylamino)propyl]-4-hydroxy-N-[4-(4-pyridinyl)phenyl]benzamide dihydrochloride (GR 55562; K$_B$ ≈ 100 nM) | British Journal of Pharmacology (2003) 138, 71-80 |
| SB224289 | Brain Res. 2004 May 8; 1007(1-2): 86-97 |
| SB 216641 | Roca-Vinardell et al., Anesthesiology, 2003, 98: 741-747 |
| Nonselective 5-HT(1B/D) receptor antagonists such as ketanserin, ritanserin and methiothepin | |

In certain embodiments, the TPH1 inhibitor and the serotonin receptor antagonist are administered together in a single pharmaceutical composition. In other embodiments, the TPH1 inhibitor and the serotonin receptor antagonist are administered in separate pharmaceutical compositions.

In certain embodiments of the methods described herein, the low bone mass disease is osteoporosis, osteoporosis pseudoglioma syndrome (OPPG), osteopenia, osteomalacia, renal osteodystrophy, faulty bone formation, faulty bone resorption, Paget's disease, bone fracture, broken bones, or bone metastasis. In preferred embodiments, the low bone mass disease is osteoporosis.

The amount of therapeutic agent to be used depends on many factors, as discussed herein. However, in humans, for example, the amount ranges from about 1 mg/day to about 2 g/day; preferably from about 15 mg/day to about 500 mg/day; or from about 20 mg/day to about 250 mg/day; or from about 40 mg/day to about 100 mg/day. Other preferred dosages include about 2 mg/day, about 5 mg/day, about 10 mg/day, about 15 mg/day, about 20 mg/day, about 25 mg/day, about 30 mg/day, about 40 mg/day, about 50 mg/day, about 60 mg/day, about 70 mg/day, about 80 mg/day, about 90 mg/day, about 100 mg/day, about 125 mg/day, about 150 mg/day, about 175 mg/day, about 200 mg/day, about 250 mg/day, about 300 mg/day, about 350 mg/day, about 400 mg/day, about 500 mg/day, about 600 mg/day, about 700 mg/day, about 800 mg/day, and about 900 mg/day.

Other amounts may range from about 1 mg/day to about 2 g/day; preferably from about 15 mg/day to about 500 mg/day; or from about 20 mg/day to about 250 mg/day; or from about 40 mg/day to about 100 mg/day. Other preferred dosages include about 2 mg/day, about 5 mg/day, about 10 mg/day, about 15 mg/day, about 20 mg/day, about 25 mg/day, about 30 mg/day, about 40 mg/day, about 50 mg/day, about 60 mg/day, about 70 mg/day, about 80 mg/day, about 90 mg/day, about 100 mg/day, about 125 mg/day, about 150 mg/day, about 175 mg/day, about 200 mg/day, about 250 mg/day, about 300 mg/day, about 350 mg/day, about 400 mg/day, about 500 mg/day, about 600 mg/day, about 700 mg/day, about 800 mg/day, and about 900 mg/day.

Other dose ranges that may be used include from about 50 mg/day to about 15 g/day; from about 50 mg/day to about 10 g/day; from about 50 mg/day to about 5 g/day; from about 50 mg/day to about 1 g/day; from about 50 mg/day to about 900 mg/day; from about 50 mg/day to about 800 mg/day; from about 50 mg/day to about 700 mg/day; from about 50 mg/day to about 600 mg/day; from about 50 mg/day to about 500 mg/day; from about 50 mg/day to about 400 mg/day; from about 50 mg/day to about 300 mg/day; or from about 50 mg/day to about 200 mg/day.

Other dose ranges that may be used include from about 100 mg/day to about 15 g/day; from about 100 mg/day to about 10 g/day; from about 100 mg/day to about 5 g/day; from about 100 mg/day to about 1 g/day; from about 100 mg/day to about 900 mg/day; from about 100 mg/day to about 800 mg/day; from about 100 mg/day to about 700 mg/day; from about 100 mg/day to about 600 mg/day; from about 100 mg/day to about 500 mg/day; from about 100 mg/day to about 400 mg/day; from about 100 mg/day to about 300 mg/day; or from about 100 mg/day to about 200 mg/day.

Other dose ranges that may be used include from about 200 mg/day to about 15 g/day; from about 200 mg/day to about 10 g/day; from about 200 mg/day to about 5 g/day; from about 200 mg/day to about 1 g/day; from about 200 mg/day to about 900 mg/day; from about 200 mg/day to about 800 mg/day; from about 200 mg/day to about 700 mg/day; from about 200 mg/day to about 600 mg/day; from about 200 mg/day to about 500 mg/day; from about 200 mg/day to about 400 mg/day; or from about 200 mg/day to about 300 mg/day.

Other dose ranges that may be used include from about 300 mg/day to about 15 g/day; from about 300 mg/day to about 10 g/day; from about 300 mg/day to about 5 g/day; from about 300 mg/day to about 1 g/day; from about 300 mg/day to about 900 mg/day; from about 300 mg/day to about 800 mg/day; from about 300 mg/day to about 700 mg/day; from about 300 mg/day to about 600 mg/day; from about 300 mg/day to about 500 mg/day; or from about 300 mg/day to about 400 mg/day.

Other dose ranges that may be used include from about 400 mg/day to about 15 g/day; from about 400 mg/day to about 10 g/day; from about 400 mg/day to about 5 g/day; from about 400 mg/day to about 1 g/day; from about 400 mg/day to about 900 mg/day; from about 400 mg/day to about 800 mg/day; from about 400 mg/day to about 700 mg/day; from about 400 mg/day to about 600 mg/day; or from about 400 mg/day to about 500 mg/day.

Other dose ranges that may be used include from about 500 mg/day to about 15 g/day; from about 500 mg/day to about 10 g/day; from about 500 mg/day to about 5 g/day; from about 500 mg/day to about 4 g/day; from about 500 mg/day to about 3 g/day; from about 500 mg/day to about 2 g/day; from about 500 mg/day to about 1 g/day; from about 500 mg/day to about 900 mg/day; from about 500 mg/day to about 800 mg/day; from about 500 mg/day to about 700 mg/day; or from about 500 mg/day to about 600 mg/day.

Other dose ranges that may be used include from about 600 mg/day to about 15 g/day; from about 600 mg/day to about 10 g/day; from about 600 mg/day to about 5 g/day; from about 600 mg/day to about 4 g/day; from about 600 mg/day to about 3 g/day; from about 600 mg/day to about 2 g/day; from about 600 mg/day to about 1 g/day; from about 600 mg/day to about 900 mg/day; from about 600 mg/day to about 800 mg/day; or from about 600 mg/day to about 700 mg/day.

Other dose ranges that may be used include from about 700 mg/day to about 15 g/day; from about 700 mg/day to about 10 g/day; from about 700 mg/day to about 5 g/day; from about 700 mg/day to about 4 g/day; from about 700 mg/day to about 3 g/day; from about 700 mg/day to about 2 g/day; from about 700 mg/day to about 1 g/day; from about 700 mg/day to about 900 mg/day; or from about 700 mg/day to about 800 mg/day.

Other dose ranges that may be used include from about 800 mg/day to about 15 g/day; from about 800 mg/day to about 10 g/day; from about 800 mg/day to about 5 g/day; from about 800 mg/day to about 4 g/day; from about 800 mg/day to about 3 g/day; from about 800 mg/day to about 2 g/day; from about 800 mg/day to about 1 g/day; or from about 800 mg/day to about 900 mg/day.

Other dose ranges that may be used include from about 900 mg/day to about 15 g/day; from about 900 mg/day to about 10 g/day; from about 900 mg/day to about 5 g/day; from about 900 mg/day to about 4 g/day; from about 900 mg/day to about 3 g/day; from about 900 mg/day to about 2 g/day; or from about 900 mg/day to about 1 g/day.

Other dose ranges that may be used include from about 1 g/day to about 15 g/day; from about 1 g/day to about 10 g/day; from about 1 g/day to about 5 g/day; from about 1 g/day to about 4 g/day; from about 1 g/day to about 3 g/day; or from about 1 g/day to about 2 g/day.

Other dosages that may be used include from about 1 g/day, about 2 g/day, about 3 g/day, about 4 g/day, about 5 g/day, about 6 g/day, about 7 g/day, about 8 g/day, about 9 g/day, about 10 g/day, about 11 g/day, about 12 g/day, about 13 g/day, about 14 g/day, or about 15 g/day.

The amount of therapeutic agent disclosed herein to be administered to a patient may range from about 5 mg/kg/day to about 500 mg/kg/day, from about 5 mg/kg/day to about 400 mg/kg/day, from about 5 mg/kg/day to about 300 mg/kg/day, from about 5 mg/kg/day to about 250 mg/kg/day, from about 5 mg/kg/day to about 200 mg/kg/day, from about 5 mg/kg/day to about 150 mg/kg/day, from about 5 mg/kg/day to about 100 mg/kg/day, from about 5 mg/kg/day to about 75 mg/kg/day, from about 5 mg/kg/day to about 50 mg/kg/day, from about 5 mg/kg/day to about 40 mg/kg/day, from about 5 mg/kg/day to about 35 mg/kg/day, from about 5 mg/kg/day to about 30 mg/kg/day, from about 5 mg/kg/day to about 25 mg/kg/day, from about 5 mg/kg/day to about 24 mg/kg/day, from about 5 mg/kg/day to about 23 mg/kg/day, from about 5 mg/kg/day to about 22 mg/kg/day, from about 5 mg/kg/day to about 21 mg/kg/day, from about 5 mg/kg/day to about 20 mg/kg/day, from about 5 mg/kg/day to about 19 mg/kg/day, from about 5 mg/kg/day to about 18 mg/kg/day, from about 5 mg/kg/day to about 17 mg/kg/day, from about 5 mg/kg/day to about 16 mg/kg/day, from about 5 mg/kg/day to about 15 mg/kg/day, from about 5 mg/kg/day to about 14 mg/kg/day, from about 5 mg/kg/day to about 13 mg/kg/day, from about 5 mg/kg/day to about 12 mg/kg/day, from about 5 mg/kg/day to about 11 mg/kg/day, or from about 5 mg/kg/day to about 10 mg/kg/day.

Other dose ranges that may be used include from about 10 mg/kg/day to about 500 mg/kg/day, from about 10 mg/kg/day to about 400 mg/kg/day, from about 10 mg/kg/day to about 300 mg/kg/day, from about 10 mg/kg/day to about 250 mg/kg/day, from about 10 mg/kg/day to about 200 mg/kg/day, from about 10 mg/kg/day to about 150 mg/kg/day, from about 10 mg/kg/day to about 100 mg/kg/day, from about 10 mg/kg/day to about 75 mg/kg/day, from about 10 mg/kg/day to about 50 mg/kg/day, from about 10 mg/kg/day to about 45 mg/kg/day, from about 10 mg/kg/day to about 40 mg/kg/day, from about 10 mg/kg/day to about 35 mg/kg/day, from about 10 mg/kg/day to about 34 mg/kg/day, from about 10 mg/kg/day to about 33 mg/kg/day, from about 10 mg/kg/day to about 32 mg/kg/day, from about 10 mg/kg/day to about 31 mg/kg/day, from about 10 mg/kg/day to about 30 mg/kg/day, from about 10 mg/kg/day to about 29 mg/kg/day, from about 10 mg/kg/day to about 28 mg/kg/day, from about 10 mg/kg/day to about 27 mg/kg/day, from about 10 mg/kg/day to about 26 mg/kg/day, from about 10 mg/kg/day to about 25 mg/kg/day, from about 10 mg/kg/day to about 24 mg/kg/day, from about 10 mg/kg/day to about 23 mg/kg/day, from about 10 mg/kg/day to about 22 mg/kg/day, from about 10 mg/kg/day to about 21 mg/kg/day, from about 10 mg/kg/day to about 20 mg/kg/day, from about 10 mg/kg/day to about 19 mg/kg/day, from about 10 mg/kg/day to about 18 mg/kg/day, from about 10 mg/kg/day to about 17 mg/kg/day, from about 10 mg/kg/day to about 16 mg/kg/day, or from about 10 mg/kg/day to about 15 mg/kg/day.

Other dose ranges that may be used include from about 15 mg/kg/day to about 500 mg/kg/day, from about 15 mg/kg/day to about 400 mg/kg/day, from about 15 mg/kg/day to about 300 mg/kg/day, from about 15 mg/kg/day to about 250 mg/kg/day, from about 15 mg/kg/day to about 200 mg/kg/day, from about 15 mg/kg/day to about 150 mg/kg/day, from about 15 mg/kg/day to about 100 mg/kg/day, from about 15 mg/kg/day to about 75 mg/kg/day, from about 15 mg/kg/day to about 50 mg/kg/day, from about 15 mg/kg/day to about 40 mg/kg/day, from about 15 mg/kg/day to about 30 mg/kg/day, from about 15 mg/kg/day to about 25 mg/kg/day, or from about 15 mg/kg/day to about 20 mg/kg/day.

Other dose ranges that may be used include from about 20 mg/kg/day to about 500 mg/kg/day, from about 20 mg/kg/day to about 400 mg/kg/day, from about 20 mg/kg/day to about 300 mg/kg/day, from about 20 mg/kg/day to about 250 mg/kg/day, from about 20 mg/kg/day to about 200 mg/kg/day, from about 20 mg/kg/day to about 150 mg/kg/day, from about 20 mg/kg/day to about 100 mg/kg/day, from about 20 mg/kg/day to about 75 mg/kg/day, from about 20 mg/kg/day to about 50 mg/kg/day, from about 20 mg/kg/day to about 40 mg/kg/day, from about 20 mg/kg/day to about 30 mg/kg/day, or from about 20 mg/kg/day to about 25 mg/kg/day.

Other dose ranges that may be used include from about 25 mg/kg/day to about 500 mg/kg/day, from about 25 mg/kg/day to about 400 mg/kg/day, from about 25 mg/kg/day to about 300 mg/kg/day, from about 25 mg/kg/day to about 250 mg/kg/day, from about 25 mg/kg/day to about 200 mg/kg/day, from about 25 mg/kg/day to about 150 mg/kg/day, from about 25 mg/kg/day to about 100 mg/kg/day, from about 25 mg/kg/day to about 75 mg/kg/day, from about 25 mg/kg/day to about 50 mg/kg/day, from about 25 mg/kg/day to about 40 mg/kg/day, or from about 25 mg/kg/day to about 30 mg/kg/day.

Other dose ranges that may be used include from about 30 mg/kg/day to about 500 mg/kg/day, from about 30 mg/kg/day to about 400 mg/kg/day, from about 30 mg/kg/day to about 300 mg/kg/day, from about 30 mg/kg/day to about 250 mg/kg/day, from about 30 mg/kg/day to about 200 mg/kg/day, from about 30 mg/kg/day to about 150 mg/kg/day, from about 30 mg/kg/day to about 100 mg/kg/day, from about 30 mg/kg/day to about 75 mg/kg/day, from about 30 mg/kg/day to about 50 mg/kg/day, or from about 30 mg/kg/day to about 40 mg/kg/day.

Other dose ranges that may be used include from about 40 mg/kg/day to about 500 mg/kg/day, from about 40 mg/kg/day to about 400 mg/kg/day, from about 40 mg/kg/day to about 300 mg/kg/day, from about 40 mg/kg/day to about 250 mg/kg/day, from about 40 mg/kg/day to about 200 mg/kg/day, from about 40 mg/kg/day to about 150 mg/kg/day, from about 40 mg/kg/day to about 100 mg/kg/day, from about 40 mg/kg/day to about 75 mg/kg/day, from about 40 mg/kg/day to about 60 mg/kg/day, or from about 40 mg/kg/day to about 50 mg/kg/day.

Other dose ranges that may be used include from about 50 mg/kg/day to about 500 mg/kg/day, from about 50 mg/kg/day to about 400 mg/kg/day, from about 50 mg/kg/day to about 300 mg/kg/day, from about 50 mg/kg/day to about 250 mg/kg/day, from about 50 mg/kg/day to about 200 mg/kg/day, from about 50 mg/kg/day to about 175 mg/kg/day, from about 50 mg/kg/day to about 150 mg/kg/day, from about 50 mg/kg/day to about 125 mg/kg/day, from about 50 mg/kg/day to about 100 mg/kg/day, from about 50 mg/kg/day to about 75 mg/kg/day, or from about 50 mg/kg/day to about 60 mg/kg/day.

Other dose ranges that may be used include from about 60 mg/kg/day to about 500 mg/kg/day, from about 60 mg/kg/day to about 400 mg/kg/day, from about 60 mg/kg/day to about 300 mg/kg/day, from about 60 mg/kg/day to about 250 mg/kg/day, from about 60 mg/kg/day to about 200 mg/kg/day, from about 60 mg/kg/day to about 175 mg/kg/day, from about 60 mg/kg/day to about 150 mg/kg/day, from about 60 mg/kg/day to about 125 mg/kg/day, from about 60 mg/kg/day to about 100 mg/kg/day, or from about 60 mg/kg/day to about 75 mg/kg/day.

Other dose ranges that may be used include from about 70 mg/kg/day to about 500 mg/kg/day, from about 70 mg/kg/day to about 400 mg/kg/day, from about 70 mg/kg/day to about 300 mg/kg/day, from about 70 mg/kg/day to about 250 mg/kg/day, from about 70 mg/kg/day to about 200 mg/kg/day, from about 70 mg/kg/day to about 175 mg/kg/day, from about 70 mg/kg/day to about 150 mg/kg/day, from about 70 mg/kg/day to about 125 mg/kg/day, or from about 70 mg/kg/day to about 100 mg/kg/day.

Other dose ranges that may be used include from about 80 mg/kg/day to about 500 mg/kg/day, from about 80 mg/kg/day to about 400 mg/kg/day, from about 80 mg/kg/day to about 300 mg/kg/day, from about 80 mg/kg/day to about 250 mg/kg/day, from about 80 mg/kg/day to about 200 mg/kg/day, from about 80 mg/kg/day to about 175 mg/kg/day, from about 80 mg/kg/day to about 150 mg/kg/day, from about 80 mg/kg/day to about 125 mg/kg/day, or from about 80 mg/kg/day to about 100 mg/kg/day.

Other dose ranges that may be used include from about 90 mg/kg/day to about 500 mg/kg/day, from about 90 mg/kg/day to about 400 mg/kg/day, from about 90 mg/kg/day to about 300 mg/kg/day, from about 90 mg/kg/day to about 250 mg/kg/day, from about 90 mg/kg/day to about 200 mg/kg/day, from about 90 mg/kg/day to about 175 mg/kg/day, from about 90 mg/kg/day to about 150 mg/kg/day, from about 90 mg/kg/day to about 125 mg/kg/day, or from about 90 mg/kg/day to about 100 mg/kg/day.

Other dose ranges that may be used include from about 100 mg/kg/day to about 500 mg/kg/day, from about 100 mg/kg/day to about 400 mg/kg/day, from about 100 mg/kg/day to about 300 mg/kg/day, from about 100 mg/kg/day to about 250 mg/kg/day, from about 100 mg/kg/day to about 200 mg/kg/day, from about 100 mg/kg/day to about 175 mg/kg/day, from about 100 mg/kg/day to about 150 mg/kg/day, or from about 100 mg/kg/day to about 125 mg/kg/day.

Other dosages that may be used include about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 45 mg/kg/day, about 50 mg/kg/day, about 60 mg/kg/day, about 70 mg/kg/day, about 80 mg/kg/day, about 90 mg/kg/day, about 100 mg/kg/day, about 125 mg/kg/day, about 150 mg/kg/day, about 175 mg/kg/day, about 200 mg/kg/day, about 250 mg/kg/day, or about 350 mg/kg/day.

Routine experimentation will determine the appropriate value for each patient by monitoring the compound's effect on serum serotonin levels, which can be frequently and easily monitored. The agent can be administered once or multiple times per day. Serum serotonin levels can be monitored before and during therapy to determine the appropriate amount of TPH1 inhibitor to administer to lower serum serotonin levels or bring serum serotonin levels to normal and to maintain normal levels over extended periods of time. In a preferred embodiment, a patient is tested to determine if his/her serum serotonin levels are significantly elevated above normal levels (about 25% above) before administering treatment with TPH1 inhibitors and, optionally, HT1B, HT2A or HT2B receptor antagonists. The frequency of administration may vary from a single dose per day to multiple doses per day.

Preferred routes of administration include oral, intravenous and intraperitoneal, but other forms of administration may be chosen as well.

Another embodiment of the present invention is directed to pharmaceutical formulations of compounds disclosed herein that are TPH1 inhibitors combined with SSRIs for administration to a patient undergoing long term SSRI administration, in order to prevent the bone loss that may occur during long term SSRI administration or to maintain or increase normal bone mass.

In certain embodiments, the compounds disclosed herein act selectively on peripheral serotonin or are administered in an amount that decreases serum serotonin without decreasing brain-derived serotonin.

In other embodiments, the compounds disclosed herein, optionally with serotonin receptor antagonists, are formulated and administered together with bisphosphonates such as FOSAMAX® (alendronate sodium), FOSAMAX PLUS D® (alendronate sodium/cholecalciferol), BONIVA® (ibandronate sodium) or other bone building drugs, vitamins or minerals to potentiate their effects on increasing bone mass.

Monitoring the therapeutic efficacy of TPH1 inhibitors is straightforward, as one can administer the inhibitors in an amount and for a duration that reduces peripheral serum serotonin levels, and over time increases bone mass. Both serum serotonin and bone mass can be easily measured. Example 1 provides the details of one immunoassay for monitoring the level of serum serotonin. Example 3 provides further assays for serum serotonin that may be used. Monitoring serum serotonin is simple and can be done frequently during the course of therapy to establish the appropriate dose for each patient. Any method known in the art for assaying serum serotonin can be used. Increased bone mass can be measured as described herein using various means of measuring bone density and markers of bone growth or can be measured by other methods known in the art.

U.S. Provisional Patent Application Ser. No. 60/976,403, filed Sep. 28, 2007, and International Patent Application PCT/US08/77870, filed Sep. 26, 2008 and published Apr. 9, 2009 as WO 2009/045900, incorporated by reference herein in their entireties, disclose that brain-derived serotonin increases bone mass and decreases sympathetic tone. Another embodiment of the present invention for treating or preventing low bone mass diseases is directed to methods for treating or preventing low bone mass by administering agents that decrease sympathetic tone, such as beta blockers, together with a compound disclosed herein that is a TPH 1 inhibitor, either in a single formulation or separately. The use of any agent that decreases sympathetic tone together with a compound disclosed herein that is a TPH 1 inhibitor comes within the scope of the invention. Preferably, the agent that decreases sympathetic tone is a beta-2 receptor antagonist, many of which are described in the art. Among the beta blockers that can be used are three beta-2 specific blockers that can be used to reduce sympathetic tone and increase bone mass, alone or in combination with other therapeutic agents described herein: IPS339, ICI118,551, and Sandoz L1 32-468 (Br. J. Ophthalmol. 1984 April; 68(4): 245-247). Butaxamine is also a beta-2 blocker that may be used in the present invention. Non-selective beta blockers include: metipranolol, nadol (a beta-specific sympatholytic which non-selectively blocks beta-2 adrenergic receptors); oxprenolol (a lipophilic beta blocker which passes the blood-brain barrier more easily than water soluble beta blockers), penbutolol, pindolol (a beta blocker that acts on serotonin 5-HT1A receptors in the brain, resulting in increased postsynaptic serotonin concentrations), and propranolol (known to readily cross the blood-brain barrier, timolol and sotalol. The beta blockers and compounds disclosed herein that are TPH1 inhibitors can be administered together with agents that directly or indirectly increase brain-derived serotonin, including HT2C receptor agonists, agents that increase TPH2 activity or expression, and agents that specifically decrease reuptake of BDS.

Certain other embodiments of the invention are directed to a pharmaceutical composition that includes a TPH1 inhibitor and an HT1B, HT2A or HT2B antagonist, individually or in combination. More than one type of TPH1 inhibitor or HT1B, HT2A or HT2B antagonist can be administered together for treating diseases associated with low bone mass, and certain embodiments include corresponding pharmaceutical compositions comprising these compounds. In other embodiments, the different types of agents are administered separately at one or more times on the same day, or over a period of days, sometimes alternating administration of the various respective agents.

Some embodiments are directed to pharmaceutical compositions for treating or preventing anxiety or depression that include both SSRIs and drugs that reduce the level of serum serotonin (e.g., TPH1 inhibitors and, optionally, HT1B antagonists) in order to prevent patients who take serotonin reuptake inhibitors from developing osteoporosis. These preparations would permit the SSRIs to elevate brain-derived serotonin to treat anxiety without increasing peripheral serotonin, which can cause low bone mass diseases like osteoporosis.

Elevated brain-derived serotonin increases bone mass by acting through HT2C receptors on target neurons in the hypothalamus. Thus, some embodiments of the present invention include administering combination drug therapy using pharmaceuticals that decrease peripheral serotonin and increase brain-derived serotonin. For example, an HT2C agonist may be combined with a TPH1 inhibitor.

In certain embodiments, the present invention provides a method comprising:
(a) identifying a patient in need of therapy for a low bone mass disease;
(b) administering to the patient a therapeutically effective amount of a compound disclosed herein that decreases serum serotonin levels.

In certain embodiments, "identifying" in step (a) above may be done by measuring the patient's level of serum serotonin, e.g., by forming a detectable complex of serum serotonin and a reagent that binds to serum serotonin in order to determine the patient's level of serum serotonin, where an elevated level of serum serotonin identifies the patient as being in need of therapy for hyperlipidemia or atherosclerosis. In certain embodiments, the reagent is an antibody or antibody fragment that binds to serotonin. In certain embodiments, the antibody or antibody fragment that binds to serotonin is labeled (e.g., radioactively, antigenically, fluorescently, with peroxidase etc.) and measuring the patient's level of serum serotonin includes the step of detecting a physical transformation in the label (e.g., radioactive decay of the label) or in a substance acted upon by the label (oxidation of a substrate by a peroxidase label).

In certain embodiments, "identifying" in step (a) above includes transforming serotonin from a bodily sample from the patient into a derivative of serotonin, e.g., N-acylserotonin. In certain embodiments, "identifying" in step (a) above includes subjecting serotonin or a serotonin derivative from a bodily sample from the patient to chromatography where the serotonin is separated from the components of the blood with which it is normally found and interacts with the stationary phase used in the chromatographic process.

In certain embodiments, the patient's level of serum serotonin is determined to be elevated in comparison to a standard level of serum serotonin that has previously been determined to be a normal level. In other embodiments, the patient's level of serum serotonin is determined to be elevated in comparison to a level of serum serotonin measured in a person who is known not to be in need of therapy for a low bone mass disease. In other embodiments, the patient's level of serum serotonin is determined to be elevated in comparison to a level of serum serotonin measured in the patient at a time when the patient was known not to be in need of therapy for a low bone mass disease.

The present invention encompasses the use of a TPH1 inhibitor and, optionally, a serotonin receptor antagonist (e.g., an HT1B antagonist) for the manufacture of a medicament for preventing or treating a bone disease (e.g., a low bone mass disease such as osteoporosis). The present invention encompasses the use of a TPH1 inhibitor and, optionally, a serotonin receptor antagonist (e.g., an HT1B antagonist) for preventing or treating a bone disease (e.g., a low bone mass disease such as osteoporosis).

The compounds disclosed herein that are TPH1 inhibitors may be useful for treating or preventing various diseases or disorders mediated by peripheral serotonin. Particular diseases or disorders include carcinoid syndrome and gastrointestinal diseases and disorders. Examples of specific diseases and disorders include abdominal pain (e.g., associated with medullary carcinoma of the thyroid), anxiety, carcinoid syndrome, celiac disease, constipation (e.g., constipation having an iatrogenic cause, and idiopathic constipation), Crohn's disease, depression, diabetes, diarrhea (e.g., bile acid diarrhea, enterotoxin-induced secretory diarrhea, diarrhea having an iatrogenic cause, idiopathic diarrhea (e.g., idiopathic secretory diarrhea), and traveler's diarrhea), emesis (e.g., chemotherapy-induced emesis), functional abdominal pain, anorectal disorders, bloating, dyspepsia, gallbladder disorders, irritable bowel syndrome (IBS; including IBD-d, IBS-c and IBS-a), lactose intolerance, MEN types I and II, nausea, Ogilvie's syndrome, Pancreatic Cholera Syndrome, pancreatic insufficiency, pheochromacytoma, scleroderma, somatization disorder, sphincter of Oddi disorders, ulcerative colitis, and Zollinger-Ellison Syndrome.

Additional diseases and disorders for which the compounds disclosed herein that are TPH1 inhibitors may be useful include cardiovascular and pulmonary diseases and disorders, such as acute and chronic hypertension, chronic obstructive pulmonary disease (COPD), pulmonary embolism (e.g., bronchoconstriction and pulmonary hypertension following pulmonary embolism), pulmonary hypertension (e.g., pulmonary hypertension associated with portal hypertension), and radiation pneumonitis (including that giving rise to or contributing to pulmonary hypertension). Others include abdominal migraine, adult respiratory distress syndrome (ARDS), carcinoid crisis, CREST syndrome (calcinosis, Raynaud's phenomenon, esophageal dysfunction, sclerodactyl), telangiectasia), serotonin syndrome, and subarachnoid hemorrhage.

Pharmaceutical Compositions

Therapeutic agents such as TPH1 inhibitors, serotonin receptor antagonists, serotonin receptor agonists, SSRIs, and beta blockers described herein may be formulated into pharmaceutical compositions. The therapeutic agents may be present in the pharmaceutical compositions in the form of salts of pharmaceutically acceptable acids or in the form of bases. The therapeutic agents may be present in amorphous form or in crystalline forms, including hydrates and solvates. Preferably, the pharmaceutical compositions comprise a therapeutically effective amount of a TPH1 inhibitor or serotonin receptor antagonist.

Pharmaceutically acceptable derivatives of any of the TPH1 inhibitors, serotonin receptor antagonists, or serotonin receptor agonists described herein come within the scope of the invention. A "pharmaceutically acceptable derivative" of a TPH1 inhibitor, serotonin receptor antagonist, or serotonin receptor agonist means any non-toxic derivative of a TPH1 inhibitor, serotonin receptor antagonist, or serotonin receptor agonist described herein that, upon administration to a recipient, exhibits that same or similar biological activity with respect to reducing serum serotonin expression or modulating serotonin receptor activity as the TPH1 inhibitors, serotonin receptor antagonists, or serotonin receptor agonists described herein.

Pharmaceutically acceptable salts of the compounds described herein for use in treating or preventing diseases associated with abnormally low bone mass, include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} alkyl)_4$ salts. This invention also envisions the quaternization of any basic nitrogen-containing groups of the therapeutic agents disclosed herein. Water or oil-soluble or dispersible products may be obtained by such quaternization.

Unless indicated otherwise, the compounds disclosed herein are also meant to include all stereochemical forms of the compounds disclosed herein (i.e., the R and S configurations for each asymmetric center). Single enantiomers, racemic mixtures, and diastereomers of the compounds disclosed herein are within the scope of the invention. Also within the scope of the invention are steric isomers and positional isomers of the compounds disclosed herein. The compounds disclosed herein are also meant to include compounds which differ only in the presence of one or more isotopically enriched atoms. For example, compounds disclosed herein in which a molecule of hydrogen is replaced by deuterium or tritium, or the replacement of a carbon molecule by $^{13}C$- or $^{14}C$-enriched carbon are within the scope of this invention.

In a preferred embodiment, the compounds disclosed herein are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the compound with which it is formulated. Pharmaceutically acceptable carriers, adjuvants or vehicles that may be used in the compositions of this invention encompass any of the standard pharmaceutically accepted liquid carriers, such as a phosphate-buffered saline solution, water, as well as emulsions such as an oil/water emulsion or a triglyceride emulsion. An example of an acceptable triglyceride emulsion useful in the intravenous and intraperitoneal administration of the compounds is the triglyceride emulsion commercially known as INTRALIPID®. Solid carriers may include excipients such as starch, milk, sugar, certain types of clay, stearic acid, talc, gums, glycols, or other known excipients. Carriers may also include flavor and color additives or other ingredients.

In the practice of the invention, the pharmaceutical compositions of the present invention are preferably administered orally. However, the pharmaceutical compositions may be administered parenterally, by inhalation spray, topically, rectally, nasally, buccally, vaginally or via an implanted reservoir. Preferably, the pharmaceutical compositions are administered orally, intraperitoneally or intravenously. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The pharmaceutical compositions of this invention may also be administered by nasal aerosol or inhalation. Such pharmaceutical compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Should topical administration be desired, it can be accomplished using any method commonly known to those skilled in the art and includes but is not limited to incorporation of the pharmaceutical composition into creams, ointments, or transdermal patches.

Where the pharmaceutical compositions contain both agents that act peripherally like HT1B antagonists or TPH1 inhibitors and agents that act centrally like HT2C agonists, the compositions can be formulated to increase delivery of the centrally acting therapeutic agents to the central nervous system. If a compound having therapeutic utility does not easily cross the blood brain barrier, it can be modified using various methods in medicinal chemistry known in the art that attach various side groups to improve permeability through the blood brain barrier.

Serotonin receptor antagonists (e.g., HT1B receptor antagonists) can be derivatized or otherwise designed to enhance uptake by bone, using medicinal chemistry methods known in the art.

The TPH1 inhibitors and HT1B antagonists can be derivatized by the formation of a reversible linkage with one or more suitable groups to yield "pro-drugs," i.e., chemical derivatives that, after absorption by the host, are converted into the parent compound. Liberation of the parent compound may be by chemical hydrolysis or enzymatic attack. A derivative or pro-drug can have enhanced permeability for the target organ. In the case of TPH1 inhibitors, the target organ is the duodenum where 95% of peripheral serotonin is made. HT1B antagonists could be formulated to have enhanced penetration of bone to reach the osteoblast target. The prodrug has an enhanced permeability according to the present invention if, after administration of the pro-drug or derivative thereof to a living organism, a higher amount of the compound reaches the target organ, resulting in a higher level of effective agent, as compared to administration of the base compound without derivatization.

The amount of the therapeutic agents of the present invention that may be combined with the carrier materials to produce a pharmaceutical composition in a single dosage form will vary depending upon the host treated and the particular mode of administration. It should be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician as well as the severity of the particular disease being treated. Despite their variety, accounting for these factors in order to select an appropriate dosage or treatment regimen would require no more than routine experimentation.

Additional therapeutic agents, which are normally administered to treat bone diseases associated with abnormally high or abnormally low bone mass, may also be present in the pharmaceutical compositions of this invention. As used herein, additional therapeutic agents that are normally administered to treat a particular disease, or condition, are known as "appropriate for the disease, or condition, being treated." Examples of appropriate agents for osteoporosis include FOSAMAX®, other bisphosphonates, FORTEO® (parathyroid hormone) and beta-blockers. Those additional agents may be administered separately from the therapeutic agents of the invention, as part of a multiple dosage regimen. Alternatively, those agents may be part of a single dosage form, mixed together with the therapeutic agents of the invention in a single pharmaceutical composition. If administered as part of a multiple dosage regime, the two active agents may be administered simultaneously, sequentially or within a period of time from one another. The amount of both the therapeutic agent of the invention and the additional therapeutic agent (in those compositions which comprise an additional therapeutic agent as described above) that may be combined with the carrier materials to produce a single dosage form will vary depending upon the host treated and the particular mode of administration as well as on the nature of the therapeutic agent of the invention and the additional therapeutic agent.

Assays for TPH1 Inhibiting Activity

The ability of the compounds disclosed herein to inhibit TPH1 may be assayed by any methods known in the art. In particular, the ability of the compounds disclosed herein to inhibit TPH1 may be assayed by a method comprising:
(a) providing a source of TPH1;
(b) exposing the source of TPH1 to L-tryptophan in the absence of a compound disclosed herein;
(c) measuring the amount of 5-hydroxytryptophan produced by the source of TPH1 in the absence of the compound disclosed herein;
(d) exposing the source of TPH1 to L-tryptophan in the presence of the compound disclosed herein;
(e) measuring the amount of 5-hydroxytryptophan produced by the source of TPH1 in the presence of the compound disclosed herein;
(f) comparing the amount of 5-hydroxytryptophan produced by the source of TPH1 in the presence of the compound disclosed herein to the amount of 5-hydroxytryptophan produced by the source of TPH1 in the absence of the compound disclosed herein, thus determining the ability of the compound disclosed herein to inhibit TPH1.

In certain embodiments, the method described above includes the further step of administering the compound disclosed herein to a patient in need of therapy for a low bone mass disease.

In certain embodiments, the source of TPH1 is an isolated TPH1 enzyme, preferably human. Isolated TPH1 can be produced by in vitro expression of TPH1, e.g., in a coupled in vitro transcription/translation system. Alternatively, the source of TPH1 may be partially or highly purified preparations from cells expressing TPH1. In other embodiments, the source of TPH1 is a whole cell expressing TPH1, preferably human. In some embodiments, the whole cell has been transfected with a expression vector comprising TPH1 so that the cell expresses recombinant TPH1, preferably human. In some embodiments, the source of TPH1 may be the rat mastocytoma cell line RBL-2H3 (ATCC CRL-2256)

The mRNA and amino acid sequence of human TPH1 can be found in GenBank, at accession no. X52836. The genomic sequence can be found at AF057280. These nucleotide sequences can be used in methods well-known in the art to construct suitable expression vectors for expressing TPH1 recombinantly in cells, or in vitro.

Activators of TPH2 may be identified by a method comprising:
(a) providing a source of TPH2;
(b) exposing the source of TPH2 to L-tryptophan in the absence of a candidate compound;
(c) measuring the amount of 5-hydroxytryptophan produced by the source of TPH2 in the absence of the candidate compound;
(d) exposing the source of TPH2 to L-tryptophan in the presence of the candidate compound;
(e) measuring the amount of 5-hydroxytryptophan produced by the source of TPH2 in the presence of the candidate compound;
(f) where, if the amount of 5-hydroxytryptophan produced by the source of TPH2 in the presence of the candidate compound is greater than the amount of 5-hydroxytryptophan produced by the source of TPH2 in the absence of the candidate compound, the candidate compound is a TPH2 activator.

"Greater than" for the purpose of the herein-described methods of identifying therapeutic agents from a collection of candidate compounds refers to an amount that would not be attributed by those of skill in the art to normal variation seen in the method. Preferably, "greater than" is at least about 50%, at least about 75%, at least about 100%, at least about 250%, or at least about 500% more than the amount observed in the absence of the candidate compound.

In certain embodiments, the method described above includes the further step of administering the TPH2 activator identified in step (f) to a patient I need of therapy for a low bone mass disease.

In certain embodiments, the source of TPH2 is an isolated TPH2 enzyme, preferably human. Isolated TPH2 can be produced by in vitro expression of TPH1, e.g., in a coupled in vitro transcription/translation system. Alternatively, the source of TPH2 may be partially or highly purified preparations from cells expressing TPH2. In other embodiments, the source of TPH2 is a whole cell expressing TPH2, preferably human. In some embodiments, the whole cell has been transfected with a expression vector comprising TPH2 so that the cell expresses recombinant TPH2, preferably human.

The mRNA and amino acid sequence of human TPH2 can be found in GenBank, at accession no. AY098914. The genomic sequence can be found at AC090109. These nucleotide sequences can be used in methods well-known in the art to construct suitable expression vectors for expressing TPH2 recombinantly in cells, or in vitro.

Antagonists of a serotonin receptor may be identified by a method comprising:
(a) providing a cell expressing the serotonin receptor;
(b) exposing the cell expressing the serotonin receptor to serotonin or a serotonin analogue in the absence of a candidate compound;
(c) measuring the activation of the serotonin receptor in the absence of the candidate compound;
(d) exposing the cell expressing the serotonin receptor to serotonin or a serotonin analogue in the presence of a candidate compound;
(e) measuring the activation of the serotonin receptor in the presence of the candidate compound;
(f) where, if the amount of activation of the serotonin receptor in the presence of the candidate compound is less than the amount of activation of the serotonin receptor in the absence of the candidate compound, the candidate compound is a serotonin receptor antagonist.

Antagonists of a serotonin receptor may also be identified by a method comprising:
(a) providing a cell expressing the serotonin receptor;
(b) exposing the cell expressing the serotonin receptor to serotonin or a serotonin analogue in the absence of a candidate compound;
(c) measuring the binding of the serotonin or the serotonin analogue to the serotonin receptor in the absence of the candidate compound;
(d) exposing the cell expressing the serotonin receptor to serotonin or a serotonin analogue in the presence of a candidate compound;
(e) measuring the binding of the serotonin or the serotonin analogue to the serotonin receptor in the presence of the candidate compound;
(f) where, if the binding of the serotonin or the serotonin analogue to the serotonin receptor in the presence of the candidate compound is less than the binding of the serotonin or the serotonin analogue to the serotonin receptor in the absence of the candidate compound, the candidate compound is a serotonin receptor antagonist.

By "serotonin analogue" is meant a substance that binds to a serotonin receptor with binding characteristics similar to those of serotonin and/or activates a serotonin receptor in a manner similar to that of serotonin.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

EXAMPLES

Example 1

Animals

One month old C57Bl/6 inbred male mice, weighing 15-16 g were used in the experiments. Animals were housed under 12 h light/12 h dark conditions in a room with controlled temperature (22° C.) and humidity (60%). Mice had ad libitum access to food and water, and were used after a minimum of 4 days of acclimatization to the housing conditions. All experiments were conducted following Columbia University Guidelines for the Animal Use and Care of laboratory mice.

Experimental Protocol

Before the experiments, animals were separated into individual cages one day prior to the experiment. Compounds were fed orally (gavage) to the mouse, calculated according to the weight of the mouse, twice a day at 1700 h and at 1100 h. Oral feeding was selected over intravenous or intraperitoneal infusion of the compound for better inhibition of Tryptophan hydroxylase-1 (TPH1) present in the gut vs TPH2 that synthesizes serotonin and is present in the brain, TPH2. This route created two potential barriers for the compound to reach the brain. First, the intestinal blood barrier that may have poor permeability and hence may not allow all the amount given orally to be absorbed in the circulation. The second barrier is the blood-brain barrier that shows poor permeability to a large number of compounds. Control animals received the same volume of vehicle. Blood was collected through heart puncture on isofluorane-anaesthesized animals and allowed to clot for 5 minutes on ice. The serum was separated, snap chilled in liquid nitrogen and frozen at −80° C. till analyzed. Brainstems from all the animals were collected and processed for brain serotonin measurement through HPLC. Mice were observed for any physical or behavioral abnormality during the course of investigation.

Serotonin Measurements in Serum

The Serotonin ELISA kit obtained from the Fitzgerald company was used to measure derivatized serotonin from serum. Derivatization is part of the sample preparation. Serotonin present in the serum was first quantitatively acylated into N-Acylserotonin using the acylation reagent. The principle of the assay is based on competitive ELISA, wherein serotonin that is bound to the solid phase of the plate and the N-acylserotonin compete for the fixed number of antiserum binding sites. When the reaction is in equilibrium, free antigen and free antigen-antiserum complexes are removed by washing.

The antibody bound to the solid phase serotonin is then detected using antirabbit/peroxidase. The substrate TMB/Peroxidase reaction is read at 450 nm. The amount of antibody bound to the solid phase serotonin is inversely proportional to the concentration of serotonin in the sample.

Drugs Used in the Study para-chlorophenylalanine (pCPA) obtained from Sigma Aldrich Corp. was used. pCPA was dissolved in a twice molar solution of $NaHCO_3$ in water and given to mice orally at a dose of 250 mg/kg and 500 mg/kg.

The structure of pCPA is:

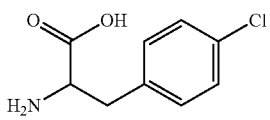

Results

Example 2

Measurement of Serum Serotonin

Two possible methods of measuring serum serotonin levels are as follows:

(1) Initial steps are performed at room temperature using polypropylene tubes and pipettes. Establishing free flow by venipuncture, blood is collected from an antecubital vein with a 19-gauge, thin-walled butterfly needle into EDTA-containing vacuum tubes. The tubes are centrifuged (Sorvall GLC-2B) at 800 rpm (100×g) for 15 minutes at room temperature. The upper layer of platelet-rich plasma (PRP), about 0.3 cm from the interface layer (buffy coat), is removed with a plastic pipette and transferred to a new polypropylene test tube. The tube containing the platelet-poor plasma (PRP) is iced for 10 min before being centrifuged at 11,000 rpm (14,500×g) in a Sorvall SS-34 rotor for 6 min at 4° C. to yield the platelet pellet and platelet poor plasma (PPP). The supernate containing PPP is removed and placed into a new polypropylene test tube in a volume of 500 microliters in Eppendorf tubes. The platelet-rich pellets are resuspended in 1 ml saline. Mixing or vortexing, before transfer to an Eppendorf tube, is sometimes required to maintain a homogenous suspension without clumps. The aliquoted plasma supernate (PPP) and the resuspended pellet (PRP) are kept at −20. For the serotonin assay, the samples are resuspended in saline. The 'hormonal' element of serotonin that is of most interest is the circulating level in PPP but the PRP fraction will also be measured. The method is an ELISA obtained from Fitzgerald Industries International (Concord, Mass.). It measures the derivatized serotonin from serum or plasma samples or urine samples. Derivatization is part of the sample preparation. Serotonin present in the biological fluids (e.g., serum) is first quantitatively acylated using the acylation reagent into N-acylserotonin. The assay is based on the competitive ELISA principle wherein serotonin that is bound to the solid phase of the plate and the N-acylserotonin competes for the fixed number of antiserum binding sites. When the reaction is in equilibrium, free antigen and free antigen-antiserum complexes are removed by washing. The antibody bound to the solid phase serotonin is then detected by the anti-rabbit/peroxidase. The substrate TMB/Peroxidase reaction is read at 450 nm. The amount of antibody bound to the solid phase serotonin is inversely proportional to the concentration of serotonin in the sample. Although the ELISA assay is useful, we will have the opportunity to apply an even more precise assay namely HPLC coupled with electrochemical detection.

(2) Another method relies on HPLC coupled with electrochemical detection. Samples obtained in the manner described above are precipitated with 1N $HClO_4$ (1:1), diluted and aliquoted into HPLC vials containing 32.5 µl of 0.02 M acetic acid. The fractions are injected via a Gilson 223 XL autoinjector onto the column. 20 µl of the microdialysis sample are injected onto a 100×2 mm C18 Hypersil 3 µm column and separated with a mobile phase consisting of 4.1 g/l sodium acetate, 500 mg/l $Na_2$-EDTA, 50 mg/l heptane sulfonic acid, 4.5% methanol v/v, and 30 µl/l of triethylamine, pH 4.75 at a flow rate of 0.4 ml/min using a Shimadzu LC-10 AD pump. Serotonin is detected amperometrically at a glassy carbon electrode at 500 mV vs Ag/AgCl. The detection limit, 0.5 fmol serotonin per 20 µl sample or 10 pM, is well within the circulating concentrations of serotonin. Since serotonin measured in PPP is not bound to any appreciable degree by plasma proteins, these measurements can be regarded as equivalent to free serotonin levels.

Example 3

Generation of Mutant Animals and Animal Treatments

Generation of Lrp5−/− (Kato et al., 2002, J. Cell Biol. 157:303-314) β-cateninfloxed/floxed (Glass et al., 2005, Dev. Cell 8:751-764), α1(I)collagen-cre transgenic (Dacquin et al., 2002, Dev. Dyn. 224:245-251) and Htt−/− (Ansorge et al., 2008, J. Neurosci. 28:199-207) mice were as described previously. Lrp5+/−;Htt+/− double heterozygous mice were generated by crossing Lrp5+/− and Htt+/− mice. Three week-old Wt or Lrp5−/− mice were administered pCPA on alternate days for 9 weeks by i.p. All animal protocols were approved by the Animal Care Committees of Columbia University.

Example 4

Morphometric Measurements

Static histomorphometry measurements were performed as previously described in accordance with standard nomenclature, using the Osteomeasure Analysis System (Osteometrics, Inc) (Ducy et al., 2000, Cell 100:197-207). Four to 9 animals were assigned per group.

Example 5

Cell Cultures

Calvaria osteoblasts were extracted by triple collagenase/trypsine digestion from 4 day-old CD1 pups and differentiated with ascorbic acid as previously described (Ducy et al., 2000, Cell 100:197-207).

Example 6

Gene Expression Studies

Osteoblasts were treated in serum-free medium with vehicle or Serotonin (50 to 100 µM, Sigma) for 24 hr. Total RNA were extracted with Trizol (Invitrogen). cDNA were generated using the ABI Reverse transcriptase system and random hexanucleotide primers. Real-time PCR was performed using superarray primers on a Stratagene real time PCR cycler and Actin expression was used as endogenous control. Chromatin immunoprecipitation assays (ChIP) were performed by standard procedures using primary osteoblasts. Microarray analysis was performed as described previously (Glass et al., 2005, Dev. Cell 8:751-764).

Example 7

Biochemical Studies

Osteoblasts were treated in serum-free medium with vehicle or Serotonin (50 to 100 µM, Sigma) for 24 hr. Lysates from primary osteoblasts or crushed frozen bones were prepared in RIPA buffer in the presence of protease and phosphatase inhibitors. Twenty to 60 µg of proteins were separated by SDS-PAGE in reducing conditions and transferred on nitrocellulose membrane using standard protocols. Membranes were incubated with primary antibodies including total or anti-Phospho CREB (Cell Signaling Technology).

Example 8

Hormone Measurements

Serotonin serum levels were quantified using immunoassay kits from Fitzgerald (Serotonin) and serotonin levels in the different regions of the brain were quantified by HPLC method as described previously (Mann et al., 1992, Arch. Gen. Psychiatry 49:442-446).

Example 9

Synthesis of Representative TPH1 Inhibitors that are Sulfonic Acids or Sulfonamides

Scheme 1

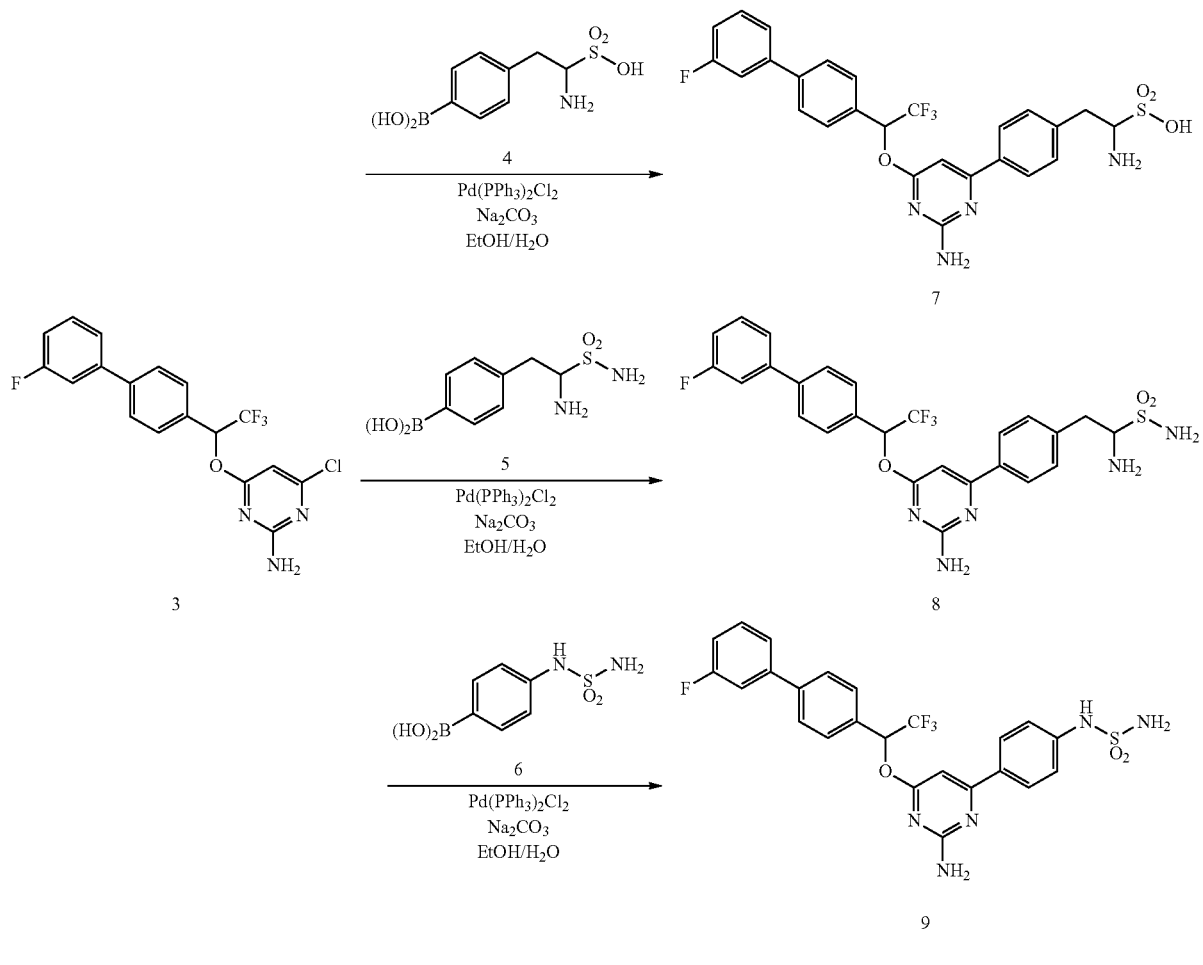

Example 10

Synthesis of representative TPH1 inhibitors that are α-amino carboxylic acids or α-amino carboxylic acid esters having a 3-5 membered ring (Scheme 2)

Knoevenagel condensation of 12 with diethyl malonate gave 13, which was reacted with dimethylsulfoxonium methylide, affording the cyploroane derivative 14. Treatment of 14 with 1 equiv of NaOH gave the monoester 15, which was converted to 16 by Curtius rearrangement. Coupling of 16 with compound 17 provides 18, which reacted with 3 to give 19 by Suzuki coupling. Deprotection of 19 gave compound 20.

Scheme 2

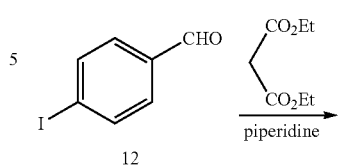

-continued

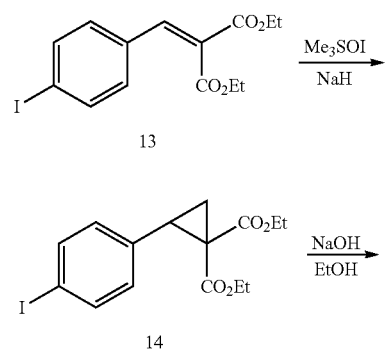

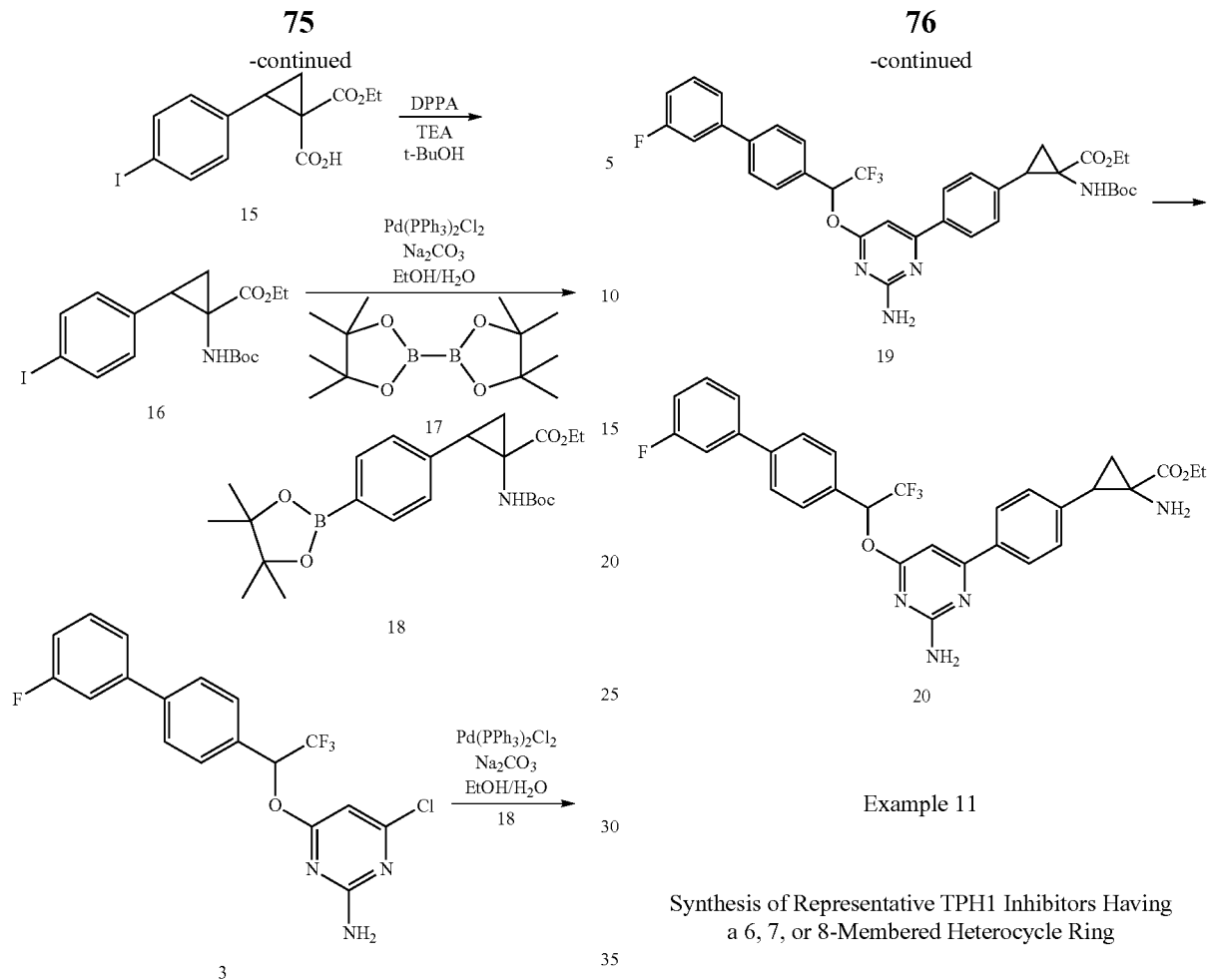
Example 11
Synthesis of Representative TPH1 Inhibitors Having a 6, 7, or 8-Membered Heterocycle Ring
Scheme 3
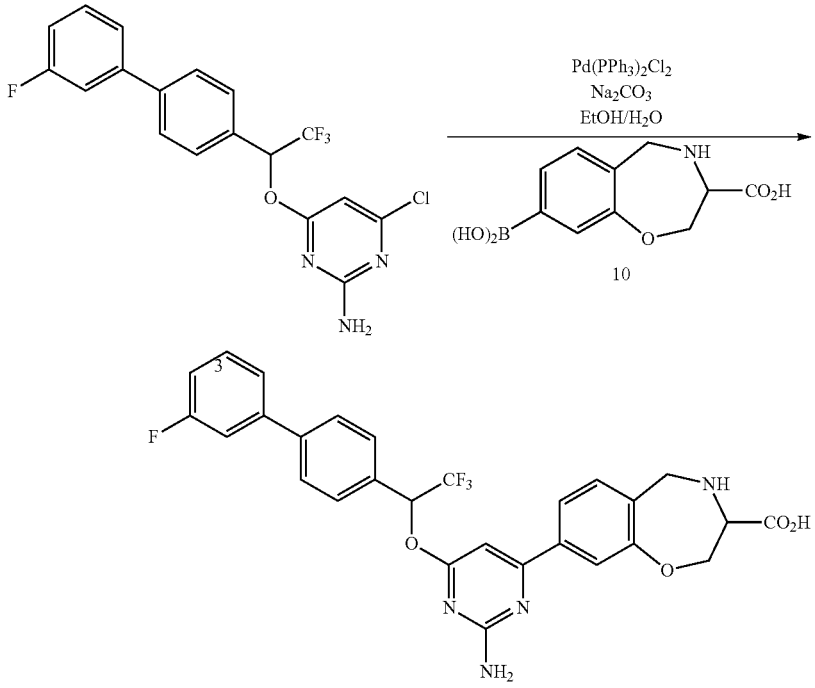

Example 12
Synthesis of Representative TPH1 Inhibitors that are β-Amino Carboxylic Acids or β-Amino Carboxylic Acid Esters
Scheme 4
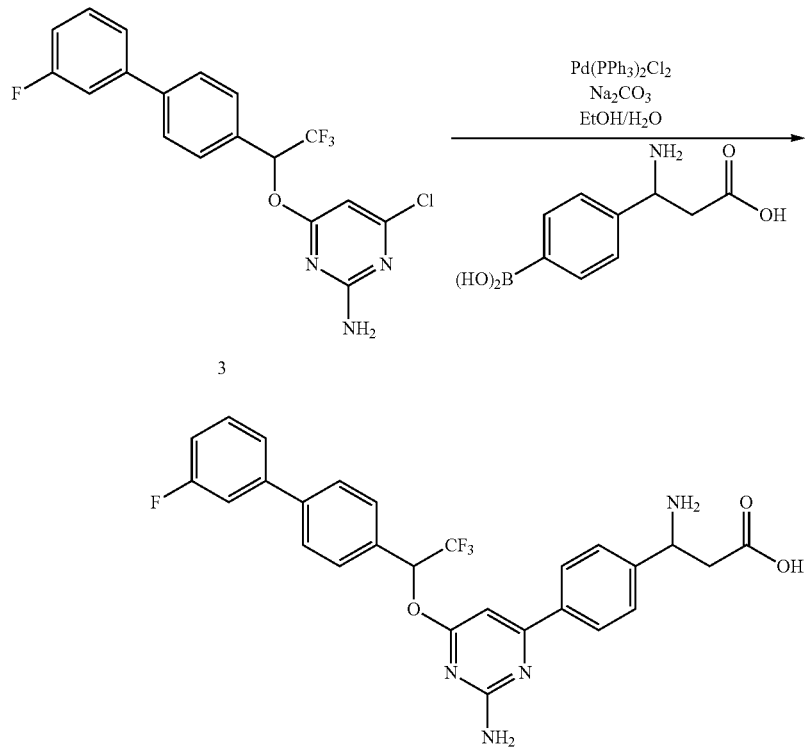
Example 13
Synthesis of Representative TPH1 Inhibitors that are Boronic Acids or Boronic Acid Esters
Scheme 5
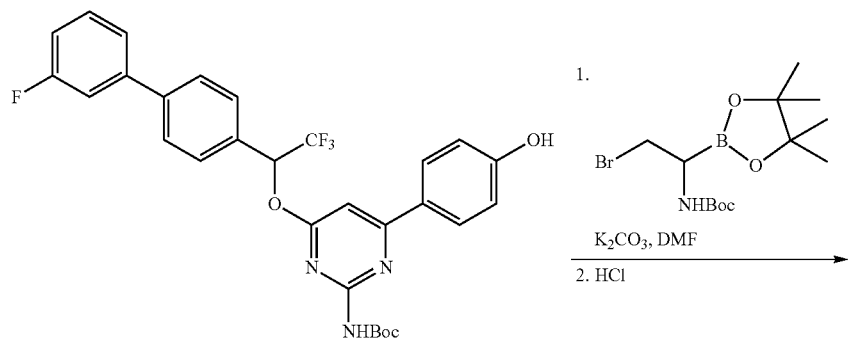

-continued

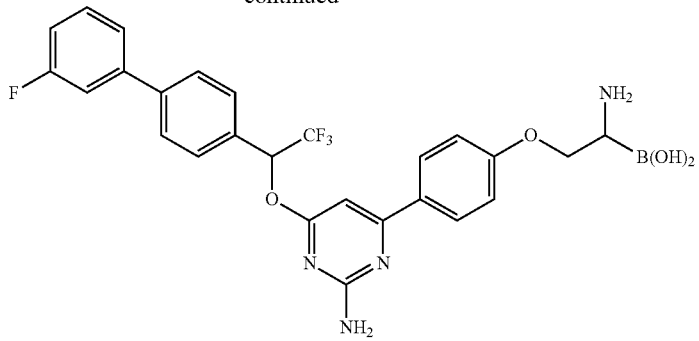

2

LITERATURE CITED

1. Gong, Y., et al., *LDL Receptor-Related Protein 5 (LRP5) Affects Bone Accrual and Eye Development.* Cell, 2001. 107(4): p. 513-23.
2. Kato, M., M. S. Patel, R. Levasseur, I. Lobov, B. H. Chang, D. A. Glass, 2nd, C. Hartmann, L. Li, T. H. Hwang, C. F. Brayton, R. A. Lang, G. Karsenty, and L. Chan, *Cbfa1-independent decrease in osteoblast proliferation, osteopenia, and persistent embryonic eye vascularization in mice deficient in Lrp5, a Wnt coreceptor.* J Cell Biol, 2002. 157(2): p. 303-14.
3. Logan, C. Y. and R. Nusse, *The Wnt signaling pathway in development and disease.* Annu Rev Cell Dev Biol, 2004. 20: p. 781-810.
4. Boyden, L. M., J. Mao, J. Belsky, L. Mitzner, A. Farhi, M. A. Mitnick, D. Wu, K. Insogna, and R. P. Lifton, *High bone density due to a mutation in LDL-receptor-related protein 5.* N Engl J Med, 2002. 346(20): p. 1513-21.
5. Glass, D. A., 2nd, et al., *Canonical Wnt signaling in differentiated osteoblasts controls osteoclast differentiation.* Dev Cell, 2005. 8(5): p. 751-764.
6. Holmen, S. L., C. R. Zylstra, A. Mukherjee, R. E. Sigler, M. C. Faugere, M. L. Bouxsein, L. Deng, T. L. Clemens, and B. O. Williams, *Essential role of beta-catenin in postnatal bone acquisition.* J Biol Chem, 2005. 280(22): p. 21162-8.
7. Gershon, M. D. and J. Tack, *The serotonin signaling system: from basic understanding to drug development for functional GI disorders.* Gastroenterology, 2007. 132(1): p. 397-414.
8. Diem, S. J., T. L. Blackwell, K. L. Stone, K. Yaffe, E. M. Haney, M. M. Bliziotes, and K. E. Ensrud, *Use of antidepressants and rates of hip bone loss in older women: the study of osteoporotic fractures.* Arch Intern Med, 2007. 167(12): p. 1240-5.
9. Haney, E. M., B. K. Chan, S. J. Diem, K. E. Ensrud, J. A. Cauley, E. Barrett-Connor, E. Orwoll, and M. M. Bliziotes, *Association of low bone mineral density with selective serotonin reuptake inhibitor use by older men.* Arch Intern Med, 2007. 167(12): p. 1246-51.
10. Schneeweiss, S, and P. S. Wang, *Association between SSRI use and hip fractures and the effect of residual confounding bias in claims database studies.* J Clin Psychopharmacol, 2004. 24(6): p. 632-8.
11. Richards, J. B., A. Papaioannou, J. D. Adachi, L. Joseph, H. E. Whitson, J. C. Prior, and D. Goltzman, *Effect of selective serotonin reuptake inhibitors on the risk of fracture.* Arch Intern Med, 2007. 167(2): p. 188-94.
12. Zhang, Y., R. Proenca, M. Maffei, M. Barone, L. Leopold, and J. M. Friedman, *Positional cloning of the mouse obese gene and its human homologue.* Nature, 1994. 372: p. 425-432.
13. Ducy, P., M. Amling, S. Takeda, M. Priemel, A. F. Schilling, F. T. Beil, J. Shen, C. Vinson, J. M. Rueger, and G. Karsenty, *Leptin inhibits bone formation through a hypothalamic relay: a central control of bone mass.* Cell, 2000. 100(2): p. 197-207.
14. Elefteriou, F., J. D. Ahn, S. Takeda, M. Starbuck, X. Yang, X. Liu, H. Kondo, W. G. Richards, T. W. Bannon, M. Noda, K. Clement, C. Vaisse, and G. Karsenty, *Leptin regulation of bone resorption by the sympathetic nervous system and CART.* Nature, 2005. 434(7032): p. 514-20.
15. Kuro-o, M., Y. Matsumura, H. Aizawa, H. Kawaguchi, T. Suga, T. Utsugi, Y. Ohyama, M. Kurabayashi, T. Kaname, E. Kume, H. Iwasaki, A. Iida, T. Shiraki-Iida, S, Nishikawa, R. Nagai, and Y. I. Nabeshima, *Mutation of the mouse klotho gene leads to a syndrome resembling ageing.* Nature, 1997. 390(6655): p. 45-51.
16. Donehower, L. A., M. Harvey, B. L. Slagle, M. J. McArthur, C. A. Montgomery, Jr., J. S. Butel, and A. Bradley, *Mice deficient for p53 are developmentally normal but susceptible to spontaneous tumours.* Nature, 1992. 356 (6366): p. 215-21.
17. Dutnall, R. N. and L. Pillus, *Deciphering NAD-dependent deacetylases.* Cell, 2001. 105(2): p. 161-4.
18. Yoshizawa, T., Y. Handa, Y. Uematsu, S. Takeda, K. Sekine, Y. Yoshihara, T. Kawakami, K. Arioka, H. Sato, Y. Uchiyama, S. Masushige, A. Fukamizu, T. Matsumoto, and S. Kato, *Mice lacking the vitamin D receptor exhibit impaired bone formation, uterine hypoplasia and growth retardation after weaning.* Nat Genet, 1997. 16(4): p. 391-6.
19. Ohshima, S., Y. Saeki, T. Mima, M. Sasai, K. Nishioka, S, Nomura, M. Kopf, Y. Katada, T. Tanaka, M. Suemura, and T. Kishimoto, *Interleukin 6 plays a key role in the development of antigen-induced arthritis.* Proc Natl Acad Sci U serotonin A, 1998. 95(14): p. 8222-6.
20. Windahl, S. H., G. Andersson, and J. A. Gustafsson, *Elucidation of estrogen receptor function in bone with the use of mouse models.* Trends Endocrinol Metab, 2002. 13(5): p. 195-200.
21. Johnson, M. L., G. Gong, W. Kimberling, S. M. Recker, D. B. Kimmel, and R. R. Recker, *Linkage of a gene causing high bone mass to human chromosome 11(11q12-13).* Am J Hum Genet, 1997. 60: p. 1326-1332.
22. Wehrli, M., S. T. Dougan, K. Caldwell, L. O'Keefe, S. Schwartz, and D. Vaizel-Ohayon, *Arrow encodes an LDL-* receptor-related protein essential for Wingless signalling. Nature, 2000. 407: p. 527-530.
23. Tamai, K., M. Semenov, Y. Kato, R. Spokony, C. Liu, Y. Katsuyama, F. Hess, J. P. Saint-Jeannet, and X. He, *LDL-receptor-related proteins in Wnt signal transduction.* Nature, 2000. 407: p. 530-535.
24. Mao, J., J. Y. Wang, L. Bo, W. Pan, G. H. Farr, III, C. Flynn, H. Yuan, S. Takada, D. Kimelman, L. Lin, and D. Wu, *Low-density lipoprotein receptor-related protein-5 binds to axin and regulates the canonical Wnt Signaling Pathway.* Mol Cell, 2001. 7: p. 801-809.
25. Day, T. F., X. Guo, L. Garrett-Beal, and Y. Yang, *Wnt/beta-catenin signaling in mesenchymal progenitors controls osteoblast and chondrocyte differentiation during vertebrate skeletogenesis.* Dev Cell, 2005. 8(5): p. 739-50.
26. Hu, H., M. J. Hilton, X. Tu, K. Yu, D. M. Ornitz, and F. Long, *Sequential roles of Hedgehog and Wnt signaling in osteoblast development.* Development, 2005. 132(1): p. 49-60.
27. Kikuchi, A., H. Yamamoto, and S. Kishida, *Multiplicity of the interactions of Wnt proteins and their receptors.* Cell Signal, 2007. 19(4): p. 659-71.
28. Chien, K. R. and G. Karsenty, *Longevity and lineages: toward the integrative biology of degenerative diseases in heart, muscle, and bone.* Cell, 2005. 120(4): p. 533-44.
29. Yoshida, Y., S. Tanaka, H. Umemori, O. Minowa, M. Usui, N. Ikematsu, E. Hosoda, T. Imamura, J. Kuno, T. Yamashita, K. Miyazono, M. Noda, T. Noda, and T. Yamamoto, *Negative regulation of BMP/Smad signaling by Tob in osteoblasts.* Cell, 2000. 103(7): p. 1085-97.
30. Tsuji, K., A. Bandyopadhyay, B. D. Harfe, K. Cox, S. Kakar, L. Gerstenfeld, T. Einhorn, C. J. Tabin, and V. Rosen, *BMP2 activity, although dispensable for bone formation, is required for the initiation of fracture healing.* Nat Genet, 2006. 38(12): p. 1424-9.
31. Zhao, G., M. C. Monier-Faugere, M. C. Langub, Z. Geng, T. Nakayama, J. W. Pike, S. D. Chernausek, C. J. Rosen, L. R. Donahue, H. H. Malluche, J. A. Fagin, and T. L. Clemens, *Targeted overexpression of insulin-like growth factor I to osteoblasts of transgenic mice: increased trabecular bone volume without increased osteoblast proliferation.* Endocrinology, 2000. 141(7): p. 2674-82.
32. Takeda, S., F. Elefteriou, R. Levasseur, X. Liu, L. Zhao, K. L. Parker, D. Armstrong, P. Ducy, and G. Karsenty, *Leptin regulates bone formation via the sympathetic nervous system.* Cell, 2002. 111(3): p. 305-17.
33. Abe, E., R. C. Marians, W. Yu, X. B. Wu, T. Ando, Y. Li, J. Iqbal, L. Eldeiry, G. Rajendren, H. C. Blair, T. F. Davies, and M. Zaidi, *TSH is a negative regulator of skeletal remodeling.* Cell, 2003. 115(2): p. 151-62.
34. Gershon, M. D., P. R. Wade, A. L. Kirchgessner, and H. Tamir, *5-HT receptor subtypes outside the central nervous system. Roles in the physiology of the gut.* Neuropsychopharmacology, 1990. 3(5-6): p. 385-95.
35. Walther, D. J., J. U. Peter, S. Bashammakh, H. Hortnagl, M. Voits, H. Fink, and M. Bader, *Synthesis of serotonin by a second tryptophan hydroxylase isoform.* Science, 2003. 299(5603): p. 76.
36. Murakami, H., K. Bessinger, J. Hellmann, and S. Murakami, *Manipulation of serotonin signal suppresses early phase of behavioral aging in Caenorhabditis elegans.* Neurobiol Aging, 2007 Feb. 28 [Epub ahead of print].
37. Sze, J. Y., M. Victor, C. Loer, Y. Shi, and G. Ruvkun, *Food and metabolic signalling defects in a Caenorhabditis elegans serotonin-synthesis mutant.* Nature, 2000. 403(6769): p. 560-4.
38. Lesurtel, M., R. Graf, B. Aleil, D. J. Walther, Y. Tian, W. Jochum, C. Gachet, M. Bader, and P. A. Clavien, *Platelet-derived serotonin mediates liver regeneration.* Science, 2006. 312(5770): p. 104-7.
39. Matsuda, M., T. Imaoka, A. J. Vomachka, G. A. Gudelsky, Z. Hou, M. Mistry, J. P. Bailey, K. M. Nieport, D. J Walther, M. Bader, and N. D. Horseman, *Serotonin regulates mammary gland development via an autocrine-paracrine loop.* Dev Cell, 2004. 6(2): p. 193-203.
40. Nebigil, C. G., D. S. Choi, A. Dierich, P. Hickel, M. Le Meur, N. Messaddeq, J. M. Launay, and L. Maroteaux, *Serotonin 2B receptor is required for heart development.* Proc Natl Acad Sci U serotonin A, 2000. 97(17): p. 9508-13.
41. Westbroek, I., A. van der Plas, K. E. de Rooij, J. Klein-Nulend, and P. J. Nijweide, *Expression of serotonin receptors in bone.* J Biol Chem, 2001. 276(31): p. 28961-8.
42. Hanley, H. G., S. M. Stahl, and D. X. Freedman, *Hyperserotonemia and amine metabolites in autistic and retarded children.* Arch Gen Psychiatry, 1977. 34(5): p. 521-31.
43. Hediger, M. L., L. J. England, C. A. Molloy, K. F. Yu, P. Manning-Courtney, and J. L. Mills, *Reduced Bone Cortical Thickness in Boys with Autism or Autism Spectrum Disorder.* J Autism Dev Disord, 2007.
44. Warden, S. J., A. G. Robling, M. S. Sanders, M. M. Bliziotes, and C. H. Turner, *Inhibition of the serotonin (5-hydroxytryptamine) transporter reduces bone accrual during growth.* Endocrinology, 2005. 146(2): p. 685-93.
45. Mann, J. J., P. A. McBride, R. P. Brown, M. Linnoila, A. C. Leon, M. DeMeo, T. Mieczkowski, J. E. Myers, and M. Stanley, *Relationship between central and peripheral serotonin indexes in depressed and suicidal psychiatric inpatients.* Arch Gen Psychiatry, 1992. 49(6): p. 442-6.
46. Blakely, R. D., L. J. Defelice, and A. Galli, *Biogenic amine neurotransmitter transporters: just when you thought you knew them.* Physiology (Bethesda), 2005. 20: p. 225-31.
47. Eldridge, F. L. and D. E. Millhorn, *Central regulation of respiration by endogenous neurotransmitters and neuromodulators.* Annu Rev Physiol, 1981. 43: p. 121-35.
48. Noda, M., H. Higashida, S. Aoki, and K. Wada, *Multiple signal transduction pathways mediated by 5-HT receptors.* Mol Neurobiol, 2004. 29(1): p. 31-9.
49. Fu, L., M. S. Patel, A. Bradley, E. F. Wagner, and G. Karsenty, *The molecular clock mediates leptin regulated bone formation.* Cell, 2005. 122(5): p. 803-15.
50. Saudou, F., D. A. Amara, A. Dierich, M. LeMeur, S. Ramboz, L. Segu, M. C. Buhot, and R. Hen, *Enhanced aggressive behavior in mice lacking 5-HT1B receptor.* Science, 1994. 265(5180): p. 1875-8.
51. Weisstaub, N. V., M. Zhou, A. Lira, E. Lambe, J. Gonzalez-Maeso, J. P. Hornung, E. Sibille, M. Underwood, S. Itohara, W. T. Dauer, M. S. Ansorge, E. Morelli, J. J. Mann, M. Toth, G. Aghajanian, S. C. Sealfon, R. Hen, and J. A. Gingrich, *Cortical 5-HT2A receptor signaling modulates anxiety-like behaviors in mice.* Science, 2006. 313(5786): p. 536-40.
52. Yang, X., K. Matsuda, P. Bialek, S. Jacquot, H. C. Masuoka, T. Schinke, L. Li, S. Brancorsini, P. Sassone-Corsi, T. M. Townes, A. Hanauer, and G. Karsenty, *ATF4 is a substrate of RSK2 and an essential regulator of osteoblast biology; implication for Coffin-Lowry Syndrome.* Cell, 2004. 117(3): p. 387-98.

What is claimed is:

1. A compound selected from the group consisting of:

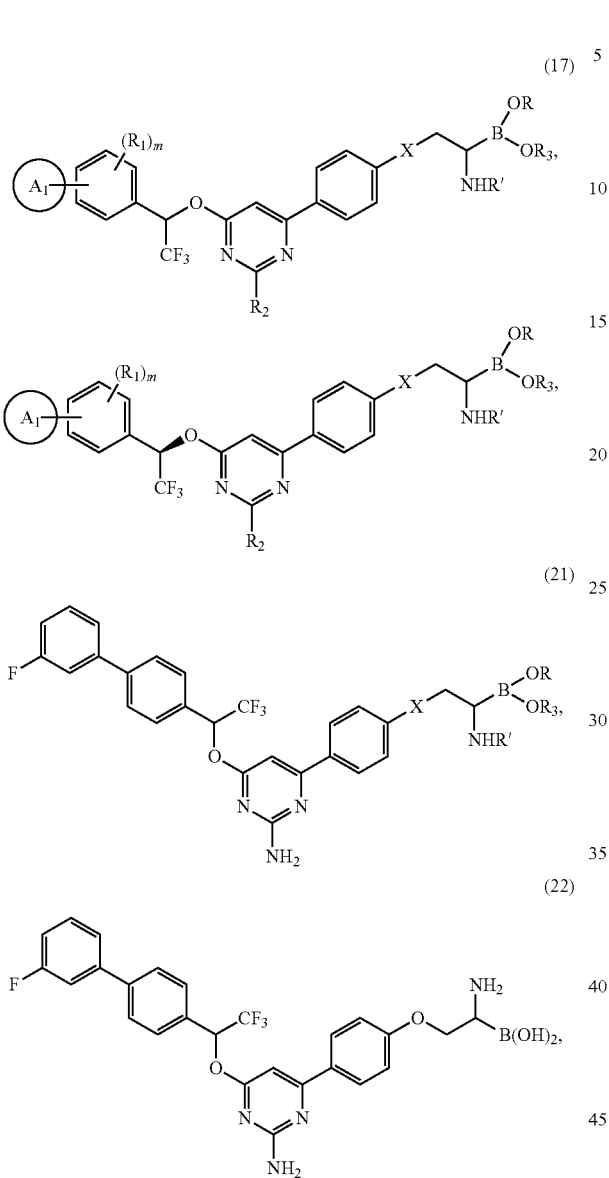

where:
A₁ is optionally substituted heterocycle;
R is hydrogen or lower alkyl;
R' is hydrogen or lower alkyl;
each $R_1$ is independently halogen, hydrogen, C(O)$R_A$, O$R_A$, N$R_B R_C$, S(O₂)$R_A$, or optionally substituted alkyl, alkyl-aryl or alkyl-heterocycle;
$R_2$ is halogen, hydrogen, C(O)$R_A$, O$R_A$, N$R_B R_C$, S(O₂)$R_A$, or optionally substituted alkyl, alkyl-aryl or alkyl-heterocycle;
$R_3$ is hydrogen or lower alkyl;
each $R_A$ is independently hydrogen or optionally substituted alkyl, alkyl-aryl or alkyl-heterocycle;
each $R_B$ is independently hydrogen or optionally substituted alkyl, alkyl-aryl or alkyl-heterocycle;
each $R_C$ is independently hydrogen or optionally substituted alkyl, alkyl-aryl or alkyl-heterocycle;
X is —CH₂—, N, S, O, or is absent; and
m is 1-4.

* * * * *